(12) United States Patent
Siegel

(10) Patent No.: US 8,216,581 B2
(45) Date of Patent: Jul. 10, 2012

(54) COMPOSITIONS, METHODS AND KITS RELATING TO ANTI-PLATELET AUTOANTIBODIES AND INHIBITORS THEREOF

(75) Inventor: Donald L. Siegel, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 915 days.

(21) Appl. No.: 11/021,715

(22) Filed: Dec. 23, 2004

(65) Prior Publication Data

US 2005/0208596 A1 Sep. 22, 2005

Related U.S. Application Data

(63) Continuation of application No. PCT/US03/21304, filed on Jul. 3, 2003.

(60) Provisional application No. 60/394,352, filed on Jul. 3, 2002, provisional application No. 60/411,694, filed on Sep. 18, 2002.

(51) Int. Cl.
*A61K 39/395* (2006.01)
*C07K 16/28* (2006.01)
*C07K 16/18* (2006.01)

(52) U.S. Cl. .............. 424/152.1; 424/133.1; 424/142.1; 424/143.1; 424/172.1; 424/800; 424/801; 424/809; 530/387.3; 530/388.2; 530/388.22; 530/388.7; 530/388.15; 530/866; 530/867

(58) Field of Classification Search .................. None
See application file for complete search history.

(56) References Cited

U.S. PATENT DOCUMENTS 5,976,532 A 11/1999 Coller et al.

FOREIGN PATENT DOCUMENTS

| EP | 206532 | 12/1986 |
|---|---|---|
| WO | WO 89/11538 | 11/1989 |
| WO | WO 00/26667 | 5/2000 |

OTHER PUBLICATIONS

Roark et al., Blood, 100:1388-1398, 2002.*
Beglova et al, "Cysteine-Rich Module Structure Reveals a Fulcrum for Integrin Rearrangement Upon Activation," *Nature Structural Biology*, vol. 9(4), pp. 282-287, 2002.
Boucher et al., "Restricted Use of Cationic Germline $V_H$ Gene Segments in Human Rh(D) Red Cell Antibodies," *Blood*, vol. 89(9), pp. 3277-3286, 1997.
Chang et al., "Isolation of an IgG Anti-B From a Human Fab-Phage Display Library," *Transfusion*, vol. 41, pp. 6-12, 2001.
Crowley et al., "The Incidence of a New Human Cross-Reactive Idiotype Linked to Subgroup $V_H$III Heavy Chains," *Molecular Immunology*, vol. 27(1), pp. 87-94, 1990.
He et al., "Spectrum of Ig Classes, Specificities, and Titers of Serum Antiglycoproteins in Chronic Idiopathic Thrombocytopenic Purpura," *Blood*, vol. 83(4), pp. 1024-1032, 1994.
Jendreyko et al., "Genetic Origin of IgG Antibodies Cloned by Phage Display and Anti-idiotypic Panning from Autoimmune Thrombocytopenia," *European Journal of Immunology*, vol. 28, pp. 4236-4247, 1998.
Kiefel et al., "Autoantibodies Against Platelet Glycoprotein Ib/IX: A Frequent finding in Autoimmune Thrombocytopenic Purpura," *British Journal of Haematology*, vol. 79(2), pp. 256-262, 1991.
Kunicki et al, "Nucleotide Sequence of the Human Autoantibody 2E7 Specific for the Platelet Integrin IIb Heavy Chain," *Journal of Autoimmunity*, vol. 4, pp. 433-446, 1991.
Kunicki et al., "Human Monoclonal Autoantibody 2E7 is Specific for a Peptide Sequence of Platelet Glycoprotein IIb. Localization of the Epitope to $IIb_{231-238}$ with an Immunodominant $Trp_{235}$," *Journal of Autoimmunity*, vol. 4, pp. 415-431., 1991.
McMillan et al., "Platelet-Associated and Plasma Anti-Glycoprotein Autoantibodies in Chronic ITP," *Blood*, vol. 70(4), pp. 1040-1045, 1987.
Morrison et al., "Chimeric Human Antibody Molecules: Mouse Antigen-Bonding Domains with Human Constant Region Domains," *Proceedings of the National Academy of Sciences*, USA, vol. 81, pp. 6851-6855, 1984.
Shlomchik et al., "The Role of Clonal Selection and Somatic Mutation in Autoimmunity," *Nature*, vol. 328, pp. 805-811, 1987.
Shlomchik et al.,"Anti-DNA Antibodies from Autoimmune Mice Arise by Clonal Expansion and Somatic Mutation," *Journal of Experimental Medicine*, vol. 171, pp. 265-292, 1990.
Shokri et al., "Expression of $V_H$III-Associated Cross-Reactive Idiotype on Human B Lymphocytes," *The Journal of Immunology*, vol. 146, pp. 936-940, 1991.
Siegel et al., "Expression and Characterization of Recombinant Anti-Rh(D) Antibodies on Filamentous Phage: A Model System for Isolating Human Red Blood Cell Antibodies by Repertoire Cloning," *Blood*, vol. 83(8), pp. 2334-2344, 1994.
Siegel et al., "Isolation of Cell Surface-Specific Human Monoclonal Antibodies Using Phage Display and Magnetically-Activated Cell Sorting: Application in Immunohematology," *Journal of Immunological Methods*, vol. 206, pp. 73-85, 1997.
Siegel, "Research and Clinical Applications of Antibody Phage Display in Transfusion Medicine," *Transfusion Medicine Reviews*, vol. 15(1), pp. 35-52, 2001.
Takagi et al., "Global Conformational Rearrangements in Integrin Extracellular domains in Outside-In and Inside-Out Signaling," *Cell*, vol. 110, pp. 599-611, 2002.
Tsai et al., "Antibodies to Von Willebrand Factor-Cleaving Protease in Acute Thrombotic Thrombocytopenic Purpura," *The New England Journal of Medicine*, vol. 339(22), pp. 1585-1594, 1998.
Van Leeuwen et al., "Specificity of Autoantibodies in Autoimmune Thrombocytopenia," *Blood*, vol. 59(1), pp. 23-26, 1982.
Griffin, et al., "A human monoclonal antibody specific for the leucine-33 (P1A1, HPA-1a) form of platelet glycoprotein IIIa from a V gene phage display library." 1995, Blood, 86(12): 4430-6.

(Continued)

*Primary Examiner* — Ronald Schwadron
(74) *Attorney, Agent, or Firm* — Riverside Law LLP

(57) ABSTRACT

The present invention relates to novel methods of identifying and producing an anti-platelet autoantibody. More preferably, the invention relates to identification and production of a human monoclonal anti-platelet autoantibody. Moreover, the invention relates to methods for treating or alleviating a disease, disorder or condition mediated by an anti-platelet autoantibody specifically binding with a platelet, or a component thereof, such as, but not limited to, idiopathic thrombocytopenic purpura, among others. Preferably, the antibody is an unglycosylated H44L4 Fab.

2 Claims, 52 Drawing Sheets

OTHER PUBLICATIONS

Jacobin, et al., "Human IgG monoclonal anti-alpha(IIb)beta(3)-binding fragments derived from immunized donors using phage display." 2002, J Immunol, 168(4): 2035-45.

Kunicki, et al, "A human monoclonal autoantibody specific for human platelet glycoprotein IIb (integrin alpha IIb) heavy chain." 1990, Human Antibodies and Hybrodomas, 1(2): 83-95.

Nugent, et al., "A human monoclonal autoantibody recognizes a neoantigen on glycoprotein IIIa expressed on stored and activated platelets." 1987, Blood, 70(1): 16-22.

Taylor et al., "7E3 F(ab')2, a monoclonal antibody to the platelet GPIIb/IIIa receptor, protects against microangiopathic hemolytic anemia and microvascular thrombotic renal failure in baboons treated with C4b binding protein and a sublethal infusion of *Escherichia coli*." 1997 Blood 89: 4078-4084.

Watkins, et al., "Platelet alphaIIbbeta3 recombinant autoantibodies from the B-cell repertoire of a post-transfusion purpura patient." 2002, Brit J. Haematol, 116(3): 677-685.

Fischer et al., "Platelet-reactive IgG antibodies cloned by phage display and panning with IVIG from three patients with autoimmune thrombocytopenia." 1999 Brit J Haematol 105:626-640.

* cited by examiner

FIG. 2A

Platelet Autoantibody Heavy Chains

FIG. 2B
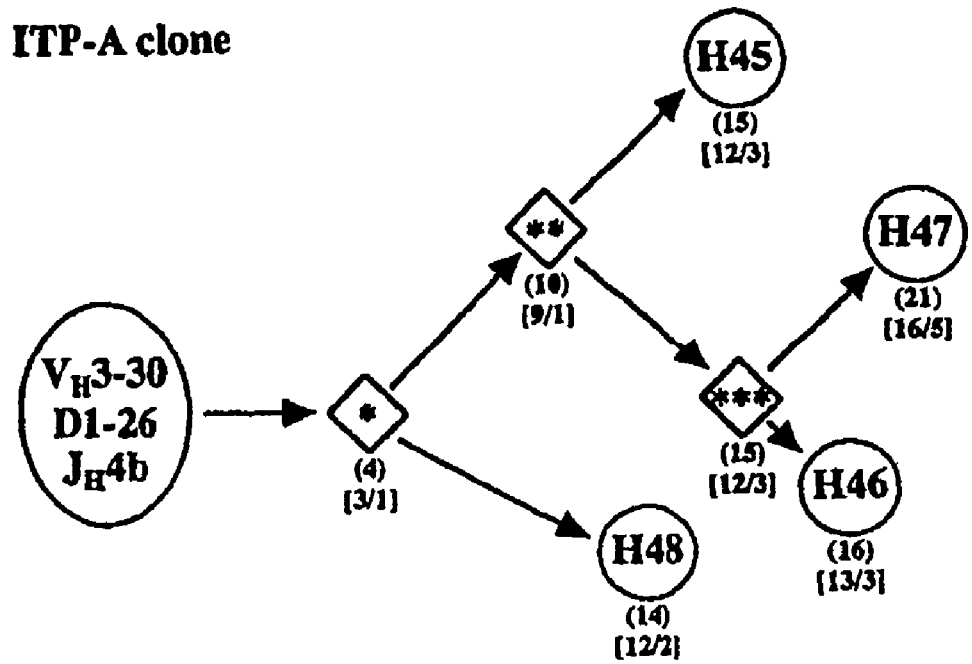
ITP-A clone
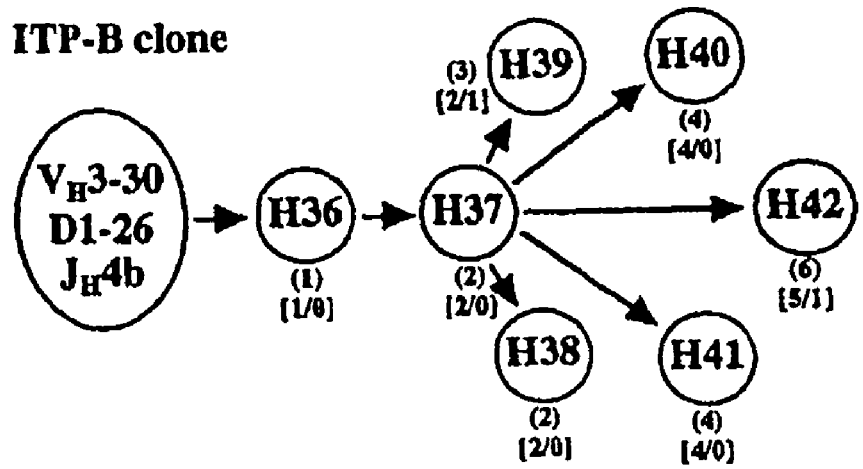
ITP-B clone

FIG. 2C

Platelet Autoantibody λ light chains

| PATIENT | $V_\lambda$ | $J_\lambda$ | FR1 | CDR1 | FR2 | CDR2 | FR3 | CDR3 | FR4 | # nucleotide differences from germline Vλ |
|---|---|---|---|---|---|---|---|---|---|---|
| | | | 1234567891234567890123 | 456789 01abc234 | 5678901234567890123 | 456 01abcd23456 | 7890123456 7ab89012345678 9012345abcde£67 | 8901234567 | | |
| ITP-B | 2a2 | JL2/JL3a | QSALTQPASVSGSPGQSITISC | TGTSSDVGGYNYVS | WYQQHPGKAPKLMIY | EV---SNRPS | GVSNRFSGSKSG--NTASLTISGLQAEDEADYYC | SSYTSSSTL++++VV | FGGGTKLTVL | |
| | L92 | JL3b | >>>>>>>> | | I. D----T... | ..K | | .R..P----- | .V... | 8 |
| ITP-B | 31 | JL3b | SSELTQDPAVSVALGQTVRITC | QGDSLR---SYYAS | WYQQKPGQAPVLVIY | GK----NNRPS | GIPDRFSGSSSG---NTASLITGAQAEDEADYYC | NSRDSSGNH+++WV | PGGGTKLTVL | |
| | L104 | | >>>>>>>>>... | -...... | ..Y.. | | | | | 1 |
| ITP-B | 4b | JL2/JL1a | QVLTQSPSASASLGASVKLTC | TLSSG--HSSVAIA | WHQQQPEKGPRYLMK | LNSDGSHSKGD | GIPDRFSGSSSG---AERYLTISSLQSEDEADYYC | QTWGTGI+++++VV | FGGGTKLTVL | |
| | L106 | | >>>>>>>P.. | | ..N.. | .V. | | .S.D..E------ | | 9 |
| ITP-B | 7b* | JL3b | QAVVTQEPSLTVSPGGTVTLTC | GSSTGAVTSGHYPY | NFQQKPGQAPRTLIY | DT---SNKHS | WTPARPSGSLLG--GKAALTLSGAQPEDEAEYYC | LLSYSGAR+++WV | PGGGTKLTVL | |
| | L122 | | >>>>>>>... | D........ | ..L... | ---H... | .G.. | S...AV--- | | 9 |

| FAMILY | GERMLINE GENE | L4 | MEAN FLUORESCENCE |
|---|---|---|---|
| Vκ1 | O2/O12 | L125 | |
| | | L126 | 2 |
| | | L127 | 7 |
| | | L128 | 3 |
| | | L129 | 5 |
| | A17 | L130 | 5 |
| | A27 | L131 | 4 |
| | | L132 | 2 |
| | | L133 | 7 |
| | | L134 | 4 |
| | B3 | L135 | 3 |
| | | L136 | 3 |
| | | L137 | 3 |
| Vλ1 | 1a | L138 | 2 |
| | 1g | L139 | 3 |
| Vλ2 | 2c | L140 | 9 |
| | 2a2 | L141 | 6 |
| | 2b2 | L142 | 2 |
| Vλ3 | 3I | | |
| Vλ4 | 4b | L143 | 2 |
| Vλ6 | 6a | L144 | 2 |
| | | L145 | 2 |

```
                                                   L1                                    L2                                                         L3
                          FR1                     CDR1              FR2                  CDR2                         FR3                           CDR3              FR4              PLATELET
                                                                                                                                                                                      REACTIVE?
              ....|....1....|....2....|....3.....|....4....|....5.....|....6....|....7....|....8....|....9....|....10
Vκ1    Jκ     12345678901234567890123 456789 01abcdef234 56789012345678 0123456 789012345678901234567890123456789012345678 9012345e67 8901234567
O12/O2 JK4    DIQMTQSPSSLSASVGDRVTITC RASQSISS------YLN WYQQKPGKAPKLLIY AASSLQS GVPSRFSGSGSGTDFTLTISSLQPEDFATYYC QQSYSTP+LT FGGGTKVEIK
CRYSTAL(L4) JK4   >>>>>.F............S.   ......T.TM-----.I.   ..............  G...P.  .........................P.........A........ ..........M. .......... YES
L125   JK1    >>>>>>................   ......T.TM-----.I.   ...............R ......  ......T.......................... .......T..+ .......... YES
L126   JK1    >>>>>>>...............   ...D-----..       ..R.............  .S T.T.  .........................V........ ...S.RP+..   .Q.........  NO
L127   JK1    >>>>>>>>..............   .....T.T.---.F.      .............. G.T.    .........................Y........E ...T.QP+..   .Q.........  NO
L128   JK2    >>>>>>>>>.............   .....T.----.   .N............        ......  .........................Y........E ...R.YI+..   .Q.........  NO
```

P4-12: GATCTGCGGCTGAATAGTCTTATTGTGCCGTGGAGT

P124-2: TTTCCGCTTATGAGTCTGATTAATCCGTGGCGTACG

P3-4: TGTCCTAGTCTGGCGCATCGTTGGTGC

P124-11: TTGCCGTTTAATACTTTGATTGTTCCTGGGCGGACT

P123-11: CTTCCGTTTGATACGATTATTAAGCCCTGGCCTGTG

P123-8: TTTCTGCCGATTTCTACGCTGATTACTCCGTCTGGT

P4-7: TTTCCTCTGAATACGATTATTCATAGTGCGGTTTAT

P124-1: ATTGATGTGTGGTGGCTTAGTACGTAGGGTGTTCCG

P123-10: TGGTCTTTGCATACTCTTGGTCTGCCTTTTGTTTTT

P74-9: TGTACGTGGCTGCCTTATCCGTATTGC

P73-10: TGTACTCATTGGTGGCGTCCGGCTTGC

P73-6: TGTGAGACTTGGTGGCGGCTTTCGTGC

P74-5: TGTGTTACGTCGAAGCCGCATACGTGC

P124-8: AAGCATAGTATGCCGATTAATGCTATTCTTCCTCCT

P73-7: TGTCAGCATAAGCTGCCTTCTAATTGC

P4-2a: TGTATTGTTCCTTGGTTTTTTCATTGC

P74-4: TGTGTGGTGCCGTGGTTTTTTCATTGC

P73-2: TGTATTGTGGAGCATTTTTTTCATTGC

P73-11: TGTCTGGTTCCGTGGATGTTTCATTGC

P74-3: TGTCTGATTCCGTGGATGTTTAATTGC

P74-1a: TGTGTGGTTCAGTGGATGTTTCAGTGC

P74-8: TGTGTTGTGTCGTGGATGTTTCAGTGC

P73-9: TGTATTATTCCGTTTATGTTTCAGTGC

FIG. 9B

CAGGTGCAGCTGGTGCAGTCTGGGGCTGAGGTGAAGAAGCCTGGGGCCTCAG
TGAGGGTCTCCTGTAAGGCTTNTGGATACAAGTTCACCGGCTCCTATATACAC
TGGGTGCGACAGGCCCCTGGACAAGGGCTTGAGTGGATGGGCCGGATCAACC
CTAACAATGGTGTCACGAACTATGCGCAGATCTTTCAGGACAGGGTCACCAT
GACCAGGGACACGTCCATCACCACGGCCTACATGGAGTTGAGCAGCCTGAGA
TCGGACGACACGGCCGTATATTACTGTGCGAGAGATATGATAGTCGACACTTT
CGCGGTCGGTTGTGACTCCTGGGGCCAGGGAACCCCGGTCACCGTCTCCTCA

FIG. 16A

CAGGTGCAGCTGGTGCAGTCAGGGGCTGAGGTGAAGAAGCCTGGGGCCTCAG
TGAAGGTTTCCTGCAAGGCATCTGGATACAGCTTCAGCAATTACTATATGCAC
TGGGTGCGACAGGCCCCTGGAGAAGGGCTTGAGTGGATGGGAATAATCAACC
CTAAAGGTGGTACCACAAGCTACGCACAGAAGTTCCAGGGCAGAGTCACGAT
TGCCGCGGACAAGTTCACGAACTCGGCCTACATGGAGCCGAGCAGCCTGAGA
TATGAGGACACGGCCGTGTATTTTTGTGCGAGAGCTAAGTTTTCATGGTCGCC
TGATATCTGGGGCCAAGGGACAGTGGTCACCGTCTCTTCA

FIG. 16B

GAGGTGCAGCTGGTGGAGTCTGGGGGAGGCCTGGTCAAGCCTGGGGGGTCCC
TGAGACTCTCCTGTGCAGCCTCTGGATTCACCTTCAGTAGCTATAGCATGAAC
TGGGTCCGCCAGGCTCCAGGGAAGGGGCTGGAGTGGGTCTCATCCATTAGTA
GTAGTAGTAGTTACATATACTACGCAGACTCAGTGAAGGGCCGATTCACCAT
CTCCAGAGACAACGCCAAGAACTCACTGTATCTGCAAATGAACAGCCTGAGA
GCCGAGGACACGGCTGTGTATTACTGTCGAGAGACCACCCTAATTACTATG
ATAGTAGTGGTCTCTTTGACTACTGGGGCCAGGGAACCCTGGTCACCGTCTCC
TCA

FIG. 16C

CAGGTGCAGCTGGTGGAGTCTGGGGGAGGCGTGGTCCAGCCTGGGAGGTCCC
TGAGACTCTCCTGTGCAGCCTCTGGATTCACCTTCAGTAGCTATGCTATGCAC
TGGGTCCGCCAGGCTCCAGGCAAGGGGCTGGAGTGGGTGGCAGTTATATCAT
ATGATGGAAGTAATAAATACTACGCAGACTCCGTGAAGGGCCGATTCACCAT
CTCCAGAGACAATTCCAAGAACACGCTGTATCTGCAAATGAACAGCCTGAGA
CCTGAGGACACGGCTGTGTATTACTGTGCGAGAGGTGGGGTAGCAGCTTTTG
ACTACTGGGGCCAGGGAACCCTGGTCACCGTCTCCTCA

FIG. 16D

CAGGTGCAGCTGGTGGAGTCTGGGGGAGGCGTGGTCCAGCCTGGGAGGTCCC
TGAGACTCTCCTGTGCAGCCTCTGGATTCACCTTCAGTAACTATGCTATGCAC
TGGGTCCGCCAGGCTCCAGGCAAGGGGCTGGAGTGGGTGGCAGTTATATCAT
ATGATGGAAGTAATAAATACTACGCAGACTCCGTGAAGGGCCGATTCACCAT
CTCCAGAGACAATTCCAAGAACACGCTGTATCTGCAAATGAACAGCCTGAGA
CCTGAGGACACGGCTGTGTATTACTGTGCGAGAGGTGGGGTAGCAGCTTTTG
ACTACTGGGGCCAGGGAACCCTGGTCACCGTCTCCTCA

FIG. 16E

CAGGTGCAGCTGGTGGAGTCTGGGGGAGGCGTGGTCCAGCCTGGGAGGTCCC
TGAGACTCTCCTGTGCAGCCTCTGGATTCACCTTCAGTAACTATGCTATGCAC
TGGGTCCGCCAGGCTCCAGGCAAGGGGCTGGAGTGGGTGGCAGTTATATCAT
ATGATGGAAGTAATAAATACTACGCAGACTCCGTGAAGGGCCGATTCACCAT
CTCCAGAGACAATTCCAAGAACACGCTGTATCTGCAAATGAACAGCCTGAGA
CCTGAGGACACGGCTGTGTATTACTGTGCGAGAGGTGGGGTAGGAGCTTTTG
ACTACTGGGGCCAGGGAACCCTGGTCACCGTCTCCTCA

FIG. 16F

CAGGTGCAGCTGGTGGAGTCTGGGGGAGGCGTGGTCCAGCCTGGGAGGTCCC
TGAGACTCTCCTGTGCAGCCTCTGGATTCACCTTCAGTAACTATGCTATGCAC
TGGGTCCGCCAGGCTCCAGGCAAGGGGCTGGAGTGGGTGGCAGTTATATCAT
ATGATGGAAGTAATAAATACTACGCAGACTCCGTGAAGGGCCGATTCACCAT
CTCCAGAGACAATTCCAAGAACACGCTGTATCTGCAAATGAACAGTCTGAGA
CCTGAGGACACGGCTGTGTATTACTGTGCGAGAGGTGGGGTAGCAGCTTTTG
ACTACTGGGGCCAGGGAACCCTGGTCACCGTCTCCTCA

FIG. 16G

CAGGTGCAGCTGGTGGAGTCTGGGGGAGGCGTGGTCCAGCCTGGGAGGTCCC
TGAGACTCTCCTGTGCAGCCTCTACATTCACCTTCAGTAACTATGCTATGCAC
TGGGTCCGCCAGGCTCCAGGCAAGGGGCTGGAGTGGGTGGCAGTTATATCAT
ATGATGGAAGTAATAAATACTACGCAGACTCCGTGAAGGGCCGATTCACCAT
CTCCAGAGACAATTCCAAGAACACGCTGTATCTGCAAATGAACAGCCTGAGA
CCTGAGGACACGGCTGTGTATTACTGTGCGAGAGGTGGGGTAGCGGCTTTTG
ACTACTGGGGCCAGGGAACCCTGGTCACCGTCTCCTCA

FIG. 16H

CAGGTGCAGCTGGTGGAGTCTGGGGGAGGCGTGGTCCAGCCTGGGAGGTCCC
TGAGACTCTCCTGTGCAGCCTCTGGATCCACCTTCAGTTACTATGCTATGCAC
TGGGTCCGCCAGGCTCCAGGCAAGGGGCTGGAGTGGGTGGCAGTTATATCAT
ATGATGGAAGTAATAAATACTACGCAGACTCCGTGAAGGGCCGATTCACCAT
CTCCAGAGACAATTCCAAGAACACGCTGTATCTGCAAATGAACAGCCTGAGA
CCTGAGGACACGGCTGTGTATTACTGTGCGAGAGGTGGGGTAGCAGCTTTTG
ACTACTGGGGTCAGGGAACCCTGGTCACCGTCTCCTCA

FIG. 16I

CAGGTGCAGCTGGTGGAGTCTGGGGGAGCCATGGTCCAGCCTGGGAGGTCCC
TGAGACTCTCCTGTGCGGCCTCTGGATTCCCCTTCAGTAACTATGCTATGCAC
TGGGTCCGCCAGGCTCCAGGCAAGGGGCTGGAGTGGGTGGCAGTTATATCAT
ATGATGGAAGTAATAAATACTACGCAGACTCCGTGAAGGGCCGATTCACCAT
CTCCAGAGACAATTCCAAGAACACGCTGTATCTGCAAATGAACAGCCTGAGA
CCTGAGGACACGGCTGTGTATTACTGTGCGAGAGGTGGGGTAGCAGCTTTTG
ACTACTGGGGCCAGGGAACCCTGGTCACCGTCTCCTCA

FIG. 16J

CAGGTGCAGCTGGTGGAGTCTGGGGGAGGCGTGGTCCAGCCTGGGAGGTCCC
TGAGACTCTCCTGTGCAGCCTCTGGATTCACCTTCAGTTACTATGCTATGGTCT
GGGTCCGCCAGGCTCCAGGCAAGGGGCTAGAGTGGGTGGCAGTTATATCAAA
TGATGGTAGGAATAAATACTACGCAGACTCCGTGAAGGGCCGATTCACCATC
TCCAGAGACAACGCCAAGAACACGCTCTATTTGCAAATGAACAGTCTGAGAG
TCGAGGACACGGCTGTGTATTACTGTCAAGGTTGGGCTACTGGGGCCCGGG
AACCCTGGTCACCGTCTCCTCA

FIG. 16K

CAGGTGCAGCTGGTGGAGTCTGGGGGAGGCGTGGTCCAGCCTGGAAGGTCCC
TGAGACTCTCCTGTGCAGCCTCTGGATTCACCTTCAGTAACTTTAATATGCAC
TGGGTCCGCCAGGCTCCAGGCAAGGGGCTGGAGTGGGTGGCACTTATATCAT
ATGATGGAAGTAGTAAATACTATACAGACTCCGTGAAGGGCCGATTCACCAT
CTCCAGAGACAATTCCAAGAACACGCTGTATCTGCAAATGAACAGCCTGAGA
CCTGAGGACACGGCTGTATATTACTGTATGGTAGTGGGAGCCTTTGACTACTG
GGGCCAGGGAACCCTGGTCACCGTCTCCTCA

FIG. 16L

CAGGTGCAGCTGGTGGAGTCTGGGGGAGGCGTGGTCCAGCCTGGGAGGTCCC
TGAGACTCTCCTGTGCAGCCTCTGGATTCACCTTCAGTAACTTTAATATGCAC
TGGGTCCGCCAGGCTCCAGGCAAGGGGCTGGAGTGGGTGGCACTAATATCAT
ATGATGGAAGTAATAAAAATTATGCAGACTCCGTGAAGGGCCGATTCACCAT
CTCCAGAGACAACTCCAAGAACACGCTGTTTCTGCAAATGAACAGCCTGAGA
GCTGAGGACACGGCTGTGTATTATTGTATGGTAGTGGGAGCCTTTGACTACTG
GGGCCAGGGTACCCTGGTCACCGTCTCCTCA

FIG. 16M

CAGGTGCAGCTGGTGGAGTCTGGGGGAGGCGTGGTCCAGCCTGGGAGGTCCC
TGAGACTCTCCTGTGCAACCTCTGGATTCACCTTCAGTAACTTTAATATGCAC
TGGGTCCGCCAGGCTCCAGGCAAGGGGCTGGAGTGGGTGGCACTAATATCAT
ATGATGGAAGTAATAAAAACTATGCAAACTCCGTGAAGGGCCGATTCACCAT
CTCCAGAGACAACTCCAAGAACACGCTGTTTCTGCAAATGAACAGCCTGAGA
GTTGAAGACACGGCTGTATATTATTGTATGGTAGTGGGAGCCTTTGACTACTG
GGGCCAGGGTACCCTGGTCACCGTCTCCTCA

FIG. 16N

CAGGTGCAGCTGGTGGAGTCTGGGGGAGGCGTGGTCCAGCCTGGGAGGTCCC
TGAGACTCTCCTGTGCAGCCTCTGGATTCACCATCAGTAATTATCACATACAC
TGGGTCCGCCAGGCTCCAGGCAAGGGGCTGGAGTGGGTGGCATTTATATCAT
ATGATGGAAGTAATAAATACTATGCAGACTCCGTGAAGGGCCGATTCACCAT
CTCCAGAGACAATTCCAAGAACACGTTGTTTCTGCAAATGAACAGCCTGACA
ACTGAGGACACGGCTGTGTATTACTGTGCGATAGTGGGACCCTTTGACTACCG
GGGCCAGGGAACCCTGGTCACCGTCTCTTCA

FIG. 16O

CAGGTGCAGCTGCAGGAGTCGGGCCCAGGACTGGTGAAGCCTTCGGAGACCC
TGTCCCTCACCTGCACTGTCTCTGGTGGCTCCATCAGTAGTTACTACTGGAGC
TGGATCCGGCAGCCCCCAGGGAAGGGACTGGAGTACATTGGGTATATCTATT
ACAGTGGGAGCACCGACTACAACCCCTCCCTCAAGAGTCGAGTCACCATATC
AGTAGACACGTCCGAGAACCAGTTCTCCCTGAAGCTGAGCTCTGTGACCGCC
GCAGACACGGCCGTCTATTACTGTGCGAGAAGCCCACCTGTTATTCGGCCCGC
TATGGACGTCTGGGGCCAAGGGACCACGGTCACCGTCTCCTCA

FIG. 16P

GACATCCAGATGACCCAGTCTCCATCCTCCCTGTCTGTATCTGTAGGAGACAG
AGTCACCATCACTTGCCGGGCAAGTCAGACCATTACTATGTATTTAAATTGGT
ATCAGCAGAAACCAGGGAAAGCCCCTAAGCTCCTGATCTATGCTGGATCCAG
TTTGCCAAGTGGAGTCCCACCAAGGTTCAGTGGCAGTGGATCTGGGACAGAT
TTCACACTCACCATCAGCAGTCTGCAACCTGAAGATTTTGCAACTTACTACTG
TCAACAGAGTTACAGTACCCTCACTTTCGGCGGAGGGACCAAGGTGGAGATG
AAA

FIG. 17A

GACATCCAGATGACCCAGTCTCCATCCTCCCTGTCTGCATCTGTAGGAGACAG
AGTCACCATCACTTGCCGGGCGAGTCAGGGCATTAGCAGTTATTTAGCCTGGT
ATCAGCAGAAACCAGGGAAAGTTCCTAAACTCCTGATCTATGCTGCATCCACT
TTGCAATCAGGGGTCCCATCTCGGTTCAGTGGCAGTGGATCTGGGACAGATTT
CACTCTCACCATCAGCAGCCTGCAGCCTGAAGATGTTGCAACTTATTACTGTC
AAAAGTATAACAGTGCCCCCCTCACTTTCGGCGGAGGGACCAAGGTGGAGAT
CAAA

FIG. 17B

GACATCCAGTTGACCCAGTCTCCAACCTTCCTGTCTGCATCTGTAGGGGACAG
AGTCACCATCACTTGCCGGGCCAGTCAGGGCATTAGTCGTTATTTAGCCTGGT
ATCAGCAAAAACCAGGGAAAGCCCCTAAGCTCCTGATCTATGCTGCATCCAC
TTTGCAAAGTGGGGTCCCATCAAGGTTCAGCGGCAGTGGATCTGGGACAGAC
TTCACTCTCACATTCAGCAGCCTGCAGCCTGAAGATTTTGCAACTTATTACTG
TCAACAGCTTAATAGTTACCCGTTCACTTTCGGCGGAGGGACCACGGTGGAG
ATCAAA

FIG. 17C

GATATTGTGATGACTCAGTCTCCACTCTCCCTGCCCGTCACCCCTGGAGAGCC
GGCCTCCATCTCCTGCAGGTCTAGTCAGAGCCTCCTGTATAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGGTACACACTGGCCTTGGACGTTCGGCCAAG
GGACCAAGGTGGAAATCAAA

FIG. 17D

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAACTCCGAGCACTTTTGGCCAGGG
GACCAAGCTGGAGATCAAA

FIG. 17E

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAACTCCCTACACTTTTGGCCAGGG
GACCAAGCTGGAGATCAAA

FIG. 17F

GATATTGTGATGACTCAGTCTCCACTCTCCCTGCCCGTCACCCCTGGAGAGCC
GGCCTCCATCTCCTGCAGGTCTAGTCAGAGCCTCCTGCATAGGAATGGATACA
ACTATTTGGATTGGTACCTGCAGAGGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTGCAGACTCCGTACACTTTCGGCCAGGG
GACCAAGCTGCAGATCAAA

FIG. 17G

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTAGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCGGGCACAGATTTTACACTGAACATCAGCAGAGTGGAGGCTGACGATGTT
GGGGTTTATTACTGCATGCAGGCTCTACAAACCCCGTACACTTTTGGCCAGGG
GACCAAGCTTGAGATCAAA

FIG. 17H

GATATTGTGATGACTCAGTCTCCACCCTCCCTGCCCGTCACCCCTGGAGAGCC
GGCCTCCATCTCCTGCAGGTCTAGTCAGAGCCTCCTGCATACTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGACAATCAGTAGAGTGGAGGCTGAGGATGTT
GGGGTTTTTTACTGCATGCAAGCTCTAGAACCTCCGTACACTTTTGGCCAGGG
GACCAAGCTGGAGATCAAA

FIG. 17I

GATATTGTGATGACTCAGTCTCCACTCTCGCTGTCCGTCAGTCCTGGAGAGCC
GGCCTCCATCTCCTGCAGGTCTAGTCAGAGCCTCCTAGATTCTAATGGACACA
ACTTTTTGGATTGGTACCTGCAGAAGCCAGGGCAGTCTCCACAACTCCTAATA
TTTGTGGGTCTTATCGGGCCTTGGGTGTCCTGACAGGTTCACTGGCAGTGG
GACAGGCACAGATTTTACACTGAAAATCAGCAGAGTGGAGCCTGAGGATGTT
GGGGTTTACTACTGCATGCAAGGTCTGCAAGCTCCTATCACTTTTGGCCAGGG
GACCAAGCTGGACATCAAA

FIG. 17J

GATATTGTGATGACTCAGTCTCCACTCTCCCTGCCCGTCACCCCTGGAGAGCC
GGCCTCCATCTCCTGCAGGTCTAGTCAGAGCCTCCTGCATCGTAATGGACACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGCGTTTATTACTGCATGCAAGCTCTACAAACTCCTTTCACTTTCGGCCCTGG
GACCAAAGTGGATATCAAA

FIG. 17K

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTGATGGATACA
ACTATTTGGATTGGTACCTGCAGAAGCCAGGGCAGTCTCCACATCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAACGCCATTCACTTTCGGCCCTGG
GACCAAAGTGGATATCAAA

FIG. 17L

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAAGTCCTCCCACTTTCGGCGGAGG
GACCAAGGTGGAGATCAAA

FIG. 17M

GATATTGTGATGACTCAGTCTCCAGTCTCCCTGGCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAGCTCCTGATC
TATTTGGGTTCTACTCGGGCCTCCGGGGTCCCTGACAGGTTCAGTGGCAGTGG
ATCAGGCACAGATTTTACACTGAAAATCAACAGAGTGGAGGCTGAGGATGTT
GGGGTATATTACTGCATGCAAGCTCTACAATCTCCTTTCACTTTCGGCGGAGG
GACCAAGGTGGAGATCAAA

FIG. 17N

GATATTGTGATGACTCAGTCTCCAGTCTCCCTGGCCGTCACCCCTGGAGAGCC
GGCCTCCATCTCCTGCAGGTCTAGTCAGAGCCTCCTGCATAGTAATGGATACA
ACTATCTGGATTGGTACCTGCAGAAGCCAGGGCAGTCTCCACAGCTCCTGATC
TATTTGGGTTCTACTCGGGCCTCCGGGGTCCCTGACAGGTTCAGTGGCAGTGG
ATCAGGCACAGATTTTACACTGAAAATCAACAGAGTGGAGGCTGAGGATGTT
GGGGTGTATTACTGCATGCAAGCTCTACAATCTCCTTTCACTTTCGGCGGAGG
GACCAAGGTGCAGATCAAA

FIG. 17O

GATATTGTGATGACTCAGTCTCCACTCTCCCTGCCCGTCACCCCTGGAGAGCC
GGCCTCCATCTCCTGCAGGTCTAGTCAGAGCCTCCTGCACAGTAATGGAAACA
ATTATTTGGATTGGTACCTGCAGAAGCCAGGGCAGTCTCCACAGCTCCTGATC
TACTTGGCTTCTAATCGGGCCTCCGGGGTCCCTGACAGGTTCAGTGGCAGTGG
ATCAGGCACGGATTTTACACTGAAAATCAGCAGAGTGGAGCCTGAGGATGTT
GGACTTTATTACTGCATGCAAGCTCTACAAACTCCGCTCACTTTCGGCGGAGG
GAGCAAGGTGGAGATCAAA

FIG. 17P

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGT
ATCAGGCACAGATTTTACACTGAAAATCAGCAGAGTGGAGGCTGAGGATGTT
GGGGTTTATTACTGCATGCAAGCTCTACAAACTCCGATCACCTTCGGCCAAGG
GACACGACTGGAGATTAAA

FIG. 17Q

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAGGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAACTCCTCCCACCTTCGGCCAAGG
GACACGACTGGAGATTAAA

FIG. 17R

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGGAAATCAGCAGAGTGGAGGCTGAGGATGTT
GGGGTTTATTACTGCATGCAAGCTCTACAAACTCCTCCGGTCACCTTCGGCCA
AGGGACACGACTGGAGATTAAA

FIG. 17S

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAACTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAACTCGTCCGGTCACCTTCGGCCA
AGGGACACGACTGGAGATTAAA

FIG. 17T

GATATTGTGATGACTCAGTCTCCACTCTCCCTGCCCGTCACCCCTGGAGAGCC
GGCCTCCATCTCCTGCAGGTCTAGTCAGAGCCTCCTGCATACTAATGGATACA
ACTATTTGGATTGGTACCTGCAGAAGCCAGGGCAGTCTCCACAGCTCCTGATC
TATTTGGGTTCTCATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAACTCCGATCACCTTCGGCCAAGG
GACACGACTGGAAATTAAA

FIG. 17U

GATATTGTGATGACTCAGTCTCCACTCTCCCTGCCCGTCACCCCTGGAGAGCC
GGCCTCCATCTCCTGCAGGTCTGGTCAGAGCCTCCTGCATAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCGCAGATTTTACACTGAAAATCAGCAGAGTGGAGGCTGAGGATGTT
GGGGTTTATTACTGCATGCAAGCTCTACAAACTCCGATCACCTTCGGCCAAGG
GACACGACTGGAGATTGAA

FIG. 17V

GATATTGTGATGACTCAGTCTCCACTCTCCCTGCCCGTCACCCCTGGAGAGCC
GGCCTCCATCTCCTGCAGGTCCAGTCAGAGCCTCCTCCATACTAATGGATACA
ACTATTTGGATTGGTATGTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAGCTCTACAAACTTTGATCACCTTCGGCCAAGG
GACACGACTGGAGATTAAA

FIG. 17W

GATATTGTGATGACTCAGTCTCCACTCTCCCTGCCCGTCACCCCTGGAGAGCC
GGCCTCCATCTCCTGCAGGTCTAGTCAGAGCCTCCTGCACAGTAATGGATACA
ACTATTTGGATTGGTACCTGCAGAAGCCAGGGCAGTCTCCACAGCTCCTGATC
TATTTGGGTTCTAATCGGGCCTCCGGGGTCCCTGACAGGTTCAGTGGCAGTGG
ATCAGGCACAGATTTTACACTGAAGATCAGCAGAGTGGAGGCTGAAGATATT
GGGGTTTATTACTGCATGCAAGCGCAAGACTCTCCGGTCACCTTCGGCCAAGG
GACACGGCTAGACATTAAC

FIG. 17X

GATATTGTGATGACTCAGTCTCCACTCTCCCTGCCCGTCACCCCTGGAGAGCC
GGCCTCCATCTCCTGTAGGTCTAATCAGAGCGTCCTGCATAGTAATGGACGGC
ACTATTTGGATTGGTATTTGCAGAAGCCAGGGCAGTCTCCACAGCTCCTGATC
TACATGGTTTTTAATCGGGCCTCCGGGGTCCCTGACAGGTTCAGTGGCAGTGG
ATCAGGCACAGATTTTACACTGAAAATCAGCAGAGTGGAGTCTGAGGATGTA
GGGGTTTATTACTGCATGCAAGCTCAACAAACTCCGGTCACCTTCGGCCAAGG
GACACGACTGGACATTAAG

FIG. 17Y

GAAATTGTGTTGACACAGTCTCCAGGCACCCTGTCTTTGTCTCCAGGGGAAAG
AGCCACCCTCTCCTGCAGGGCCAGTCAGAGTGTTGGCAGCAGCTACTTAGCCT
GGTACCAGCAGAAACCTGGCCAGGCTCCCAGGCTCCTCATCTATGGTGTATCC
AGCAGGGCCACTGGCATCCCAGACAGGTTCAGTGGCAGTGGGTCTGGGACAG
ACTTCACTCTCACCATCAGCAGGCTGGAGCCTGAAGATTTTGCAGTGTATTAC
TGTCAGCAGTATGGTGGCTCACCTCTCACTTTCGGCGGAGGGACCACGGTGG
AGATCAAA

FIG. 17Z

GAAATTGTGTTGACGCAGTCTCCAGGCACCCTGTCTTTGTCTCCAGGGGAAAG
AGCCACCCTCTCCTGCAGGGCCAGTCAGAGTGTTGGCAACAACTACTTAGCCT
GGTACCAGCAGAGACCTGGCCGGGCTCCCAGGCTCGTCATGTATGATCCATC
CAGCAGGGCCACTGGCATCCCAGACAGGTTCAGTGGCAGTGGGTCTGGGACA
GACTTCACTCTCACCATCAGCAGACTGGAGCCTGAAGATTTTGCGGTTTATTA
CTGTCAGCAGTATGGTAACTCACCTCCCACTTTCGGCGGAGGGACCAAGGTG
GAGATCAAA

FIG. 17AA

GAAATTGTGTTGACGCAGTCTCCAGACACCCTGTCTTTGTCTCCAGGGGACAG
GGCCACCCTCTCCTGCAGGGCCAGTCAGAGTGTTAGTAACTACTTAGCCTGGT
ACCAGCAGAAAGCTGGCCGGGCTCCCAGTCTCCTCATCTATGGGACATCCAG
GAGGGCCACTGACATCCCAGACAGGTTCAGTGGCAGTGGGTCTGGGACAGAC
TTCACTCTCACCATCAGCAGACTGGAACCTGAAGATTCTGCAGTATATTACTG
TCAGCAGTATGGTAGCGCATCGCTCACTTTCGGCGGAGGGACCAAGGTAGAG
ATCAAA

FIG. 17BB

GAAATTGTGTTGACACAGTCTCCAGCCACCCTGTCTGTGTCTCCAGGGGAAAG
AGCCACCCTCTCCTGCAGGGCCAGTCAGAGTGTTAGCAGCTACTTAGCCTGGT
ACCAACAGAAACCTGGCCAGGCTCCCAGGCTCCTCATCTATGATGCATCCAA
CAGGGCCACTGGCATCCCAGCCAGGTTCAGTGGCAGTGGGTCTGGGACAGAC
TTCACTCTCACCATCAGCAGCCTAGAGCCTGAAGATTTTGCAGTTTATTACTG
TCAGCAGCGTAGCAACTGGCCTCTGACGTTCGGCCAAGGGACCAAGGTGGAA
ATCAAA

FIG. 17CC

GAAATTGTGTTGACACAGTCTCCAGCCACCCTGTCTTTGTCTCCAGGGGAAAG
AGCCACCCTCTCCTGCAGGGCCAGTCAGAGTGTTAGCAGCTACTTAGCCTGGT
ACCAACAGAAACCTGGCCAGGCTCCCAGGCTCCTCATCTATGATGCATCCAA
CAGGGCCACTGGCATCCCAGCCAGGTTCAGTGGCAGTGGGTCTGGGACAGAC
TTCACTCTCACCATCAGCAGCCTAGAGCCTGAAGATTTTGCAGTTTATTACTG
TCAGCAGCGTAGCAACTGGCCCACTTTCGGCGGAGGGACCAAGGTGGAGATC
AAA

FIG. 17DD

GAAATTGTGTTGACACAGTCTCCAGCCACCCTGTCGTTGTCTCCAGGGGAAAG
AGCCACCCTCTCCTGCAGGGCCAGTCAGAGTGTTAGGAGCTTCTTAGCCTGGT
ACCAACAGAAGCCTGGCCAGGCTCCCAGGCTCCTCATTTATGATACATCCAA
GAGGCCCACTGGCATCCCAGACAGGTTCAGTGGCAGTGGGTCTGGGACAGAC
TTCACTCTCACCATCAGCAGCCTAGAACCTGAAGATTTTGCAGTGTATTACTG
TCAGCAGCGTAGCAGCTGGCCGCTCACTTTCGGCGGAGGGACCACGGTGGAG
ATCAAA

FIG. 17EE

GAAATTGTGTTGACACAGTCTCCAGCCACCCTGTCTTTGTCTCCAGGGGAAAG
AGCCACCCTCTCCTGCAGGGCCAGTCAGAGTGTTAGCAGCTACTTAGCCTGGT
ACCAACAGAAACCTGGCCAGGCTCCCAGGCTCCTCATCTATGATGCATCCAA
CAGGGCCACTGGCATCCCAGCCAGGTTCAGTGGCAGTGGGTCTGGGACAGAC
TTCACTCTCACCATCAGCAGCCTAGAGCCTGAAGATTTTGCAGTTTATTACTG
TCAGCAGCGTAGCAACTGGCCTCCGATCACCTTCGGCCAAGGGACACGACTG
GAGATTAAA

FIG. 17FF

GACATCCAGATGACCCAGTCTCCATCCTTCCTGTCTGCATCTGTAGGAGACAG
AGTCACCATCTCTTGCCGGGCAAGTCAGAGCATTGACAGCTATATAAATTGGT
ATCAGCAGAAACCAGGGAAAGCCCCTAAGCTCCTGATCTATGCTGCATCCAG
TTTGCAACGTGGGGTCCCATCAAGGTTCAGTGGCAGTGGATCTGGGACAGAT
TTCACTCTCACCATCAGCAGTCTACAACCTGAAGATTTTGCAACTTACTACTG
TCAACAGACTTACAGCACCCTCACTTTCGGCGGAGGGACCAAGGTGGAGATC
AAA

FIG. 17GG

CAGTCTGCCCTGACTCAGCCTGCCTCCGTGTCTGGGTCTCCTGGACAGTCGAT
CACCATCTCCTGCACTGGAACCAGCAGTGACGTTGGTGGTTATAAGTATGTCT
CCTGGTACCAACAGCACCCAGGCAAAGCCCCCAAACTCATAATTTATGATGT
CACCAATCGGCCCTCAGGGGTTTCTAAGCGCTTCTCTGGCTCCAAGTCTGGCA
ACACGGCCTCCCTGACCATCTCTGGGCTCCAGGCTGAGGACGAGGCTGATTAT
TACTGCAGTTCATATACAAGCAGGAGCACTCCCGTCTTCGGCGGAGGGACCA
AGGTGACCGTCCTA

FIG. 18A

TCTTCTGAGCTGACTCAGGACCCTGCTGTGTCTGTGGCCTTGGGACAGACAGT
CAGGATCACATGCCAAGGAGACAGCCTCAGAAGCTATTATGCAAGCTGGTAC
CAGCAGAAGCCAGGACAGGCCCCTGTACTTGTCATCTATGGTAAAAACTACC
GGCCCTCAGGGATCCCAGACCGATTCTCTGGCTCCAGCTCAGGAAACACAGC
TTCCTTGACCATCACTGGGGCTCAGGCGGAAGATGAGGCTGACTATTACTGTA
ACTCCCGGGACAGCAGTGGTAACCATTGGGTGTTCGGCGGAGGGACCAAGCT
GACCGTCCTA

FIG. 18B

CAGCTTGTGCTGACTCAATCGCCCCCTGCCTCTGCCTCCCTGGGAGCCTCGGT
CAAGCTCACCTGCACTCTGAGCAGTGGGCACAGCAGTTACGCCATCGCATGG
CATCAGCAACAGCCAGAGAAGGGCCCTCGGTACTTGATGAACCTTAATAGTG
ATGGCAGCCACAGCAAGGGGGACGGGGTCCCTGATCGCTTCTCAGGCTCCAG
CTCTGGGGCTGAGCGCTACCTCACCATCTCCAGCCTCCAGTCTGAGGATGAGG
CTGACTATTACTGTCAGTCTTGGGACACTGGCGAGGTGTTCGGCGGGGGGAC
CAAGTTGACCGTCCTG

FIG. 18C

CAGGCTGTGGTGACTCAGGAGCCCTCACTGACTGTGTCCCCAGGAGGGACAG
TCACTCTCACCTGTGACTCCAGCACTGGAGCTGTCACCAGTGGTCATTATCCC
TACTGGCTCCAGCAGAAGCCTGGCCAAGCCCCCAGGACACTCATTTATGATA
CACATAACAAACACTCCTGGACACCTGGCCGGTTCTCAGGCTCCCTCCTTGGG
GGCAAAGCTGCCCTGACCCTTTCGGGTGCGCAGCCTGAGGATGAGGCTGAGT
ATTACTGCTCGCTCTCGTATAGTGCTGTTTGGGTGTTCGGCGGAGGGACCAAG
CTGACCGTCCTA

FIG. 18D

QVQLVQSGAEVKKPGASVRVSCKAXGYKFTGSYIHWVRQAPGQGLEWMGRINP
NNGVTNYAQIFQDRVTMTRDTSITTAYMELSSLRSDDTAVYYCARDMIVDTFAV
GCDSWGQGTPVTVSS

FIG. 19A

QVQLVQSGAEVKKPGASVKVSCKASGYSFSNYYMHWVRQAPGEGLEWMGIINP
KGGTTSYAQKFQGRVTIAADKFTNSAYMEPSSLRYEDTAVYFCARAKFSWSPDI
WGQGTVVTVSS

FIG. 19B

EVQLVESGGGLVKPGGSLRLSCAASGFTFSSYSMNWVRQAPGKGLEWVSSISSSS
SYIYYADSVKGRFTISRDNAKNSLYLQMNSLRAEDTAVYYCARDHPNYYDSSGL
FDYWGQGTLVTVSS

FIG. 19C

QVQLVESGGGVVQPGRSLRLSCAASGFTFSSYAMHWVRQAPGKGLEWVAVISY
DGSNKYYADSVKGRFTISRDNSKNTLYLQMNSLRPEDTAVYYCARGGVAAFDY
WGQGTLVTVSS

FIG. 19D

QVQLVESGGGVVQPGRSLRLSCAASGFTFSNYAMHWVRQAPGKGLEWVAVISY
DGSNKYYADSVKGRFTISRDNSKNTLYLQMNSLRPEDTAVYYCARGGVAAFDY
WGQGTLVTVSS

FIG. 19E

QVQLVESGGGVVQPGRSLRLSCAASGFTFSNYAMHWVRQAPGKGLEWVAVISY
DGSNKYYADSVKGRFTISRDNSKNTLYLQMNSLRPEDTAVYYCARGGVGAFDY
WGQGTLVTVSS

FIG. 19F

QVQLVESGGGVVQPGRSLRLSCAASGFTFSNYAMHWVRQAPGKGLEWVAVISY
DGSNKYYADSVKGRFTISRDNSKNTLYLQMNSLRPEDTAVYYCARGGVAAFDY
WGQGTLVTVSS

FIG. 19G

QVQLVESGGGVVQPGRSLRLSCAASTFTFSNYAMHWVRQAPGKGLEWVAVISY
DGSNKYYADSVKGRFTISRDNSKNTLYLQMNSLRPEDTAVYYCARGGVAAFDY
WGQGTLVTVSS

FIG. 19H

QVQLVESGGGVVQPGRSLRLSCAASGSTFSYYAMHWVRQAPGKGLEWVAVISY
DGSNKYYADSVKGRFTISRDNSKNTLYLQMNSLRPEDTAVYYCARGGVAAFDY
WGQGTLVTVSS

FIG. 19I

QVQLVESGGAMVQPGRSLRLSCAASGFPFSNYAMHWVRQAPGKGLEWVAVISY
DGSNKYYADSVKGRFTISRDNSKNTLYLQMNSLRPEDTAVYYCARGGVAAFDY
WGQGTLVTVSS

FIG. 19J

QVQLVESGGGVVQPGRSLRLSCAASGFTFSYYAMVWVRQAPGKGLEWVAVISN
DGRNKYYADSVKGRFTISRDNAKNTLYLQMNSLRVEDTAVYYCARLGYWGPGT
LVTVSS

FIG. 19K

QVQLVESGGGVVQPGRSLRLSCAASGFTFSNFNMHWVRQAPGKGLEWVALISY
DGSSKYYTDSVKGRFTISRDNSKNTLYLQMNSLRPEDTAVYYCMVVGAFDYWG
QGTLVTVSS

FIG. 19L

QVQLVESGGGVVQPGRSLRLSCAASGFTFSNFNMHWVRQAPGKGLEWVALISY
DGSNKNYADSVKGRFTISRDNSKNTLFLQMNSLRAEDTAVYYCMVVGAFDYWG
QGTLVTVSS

FIG. 19M

QVQLVESGGGVVQPGRSLRLSCATSGFTFSNFNMHWVRQAPGKGLEWVALISY
DGSNKNYANSVKGRFTISRDNSKNTLFLQMNSLRVEDTAVYYCMVVGAFDYWG
QGTLVTVSS

FIG. 19N

QVQLVESGGGVVQPGRSLRLSCAASGFTISNYHIHWVRQAPGKGLEWVAFISYD
GSNKYYADSVKGRFTISRDNSKNTLFLQMNSLTTEDTAVYYCAIVGPFDYRGQG
TLVTVSS

FIG. 19O

QVQLQESGPGLVKPSETLSLTCTVSGGSISSYYWSWIRQPPGKGLEYIGYIYYSGS
TDYNPSLKSRVTISVDTSENQFSLKLSSVTAADTAVYYCARSPPVIRPAMDVWGQ
GTTVTVSS

FIG. 19P

DIQMTQSPSSLSVSVGDRVTITCRASQTITMYLNWYQQKPGKAPKLLIYAGSSLPS
GVPPRFSGSGSGTDFTLTISSLQPEDFATYYCQQSYSTLTFGGGTKVEMK

FIG. 20A

DIQMTQSPSSLSASVGDRVTITCRASQGISSYLAWYQQKPGKVPKLLIYAASTLQS
GVPSRFSGSGSGTDFTLTISSLQPEDVATYYCQKYNSAPLTFGGGTKVEIK

FIG. 20B

DIQLTQSPTFLSASVGDRVTITCRASQGISRYLAWYQQKPGKAPKLLIYAASTLQS
GVPSRFSGSGSGTDFTLTFSSLQPEDFATYYCQQLNSYPFTFGGGTTVEIK

FIG. 20C

DIVMTQSPLSLPVTPGEPASISCRSSQSLLYSNGYNYLDWYLQKPGQSPQLLIYLG
SNRASGVPDRFSGSGSGTDFTLKISRVEAEDVGVYYCMQGTHWPWTFGQGTKV
EIK

FIG. 20D

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQTPSTFGQGTKLEI
K

FIG. 20E

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQTPYTFGQGTKLEI
K

FIG. 20F

DIVMTQSPLSLPVTPGEPASISCRSSQSLLHRNGYNYLDWYLQRPGQSPQLLIYLG
SNRASGVPDRFSGSGSGTDFTLKISRVEAEDVGVYYCMQALQTPYTFGQGTKLQI
K

FIG. 20G

DIVMTQSPLSLPVTPGEPASISCRSSQSLLHSNGYNYLDWYLQKPGQSPQLLIYLG
SNRASGVPDRFSGSGSGTDFTLNISRVEADDVGVYYCMQALQTPYTFGQGTKLEI
K

FIG. 20H

DIVMTQSPPSLPVTPGEPASISCRSSQSLLHTNGYNYLDWYLQKPGQSPQLLIYLG
SNRASGVPDRFSGSGSGTDFTLTISRVEAEDVGVFYCMQALEPPYTFGQGTKLEIK

FIG. 20I

DIVMTQSPLSLSVSPGEPASISCRSSQSLLDSNGHNFLDWYLQKPGQSPQLLIFVGS
YRALGVPDRFTGSGTGTDFTLKISRVEPEDVGVYYCMQGLQAPITFGQGTKLDIK

FIG. 20J

DIVMTQSPLSLPVTPGEPASISCRSSQSLLHRNGHNYLDWYLQKPGQSPQLLIYLG
SNRASGVPDRFSGSGSGTDFTLKISRVEAEDVGVYYCMQALQTPFTFGPGTKVDI
K

FIG. 20K

DIVMTQSPLSLPVTPGEPASISCRSSQSLLHSDGYNYLDWYLQKPGQSPHLLIYLG
SNRASGVPDRFSGSGSGTDFTLKISRVEAEDVGVYYCMQALQTPFTFGPGTKVDI
K

FIG. 20L

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQSPPTFGGGTKVEI
K

FIG. 20M

DIVMTQSPVSLAVTPGEPASISCRSSQSLLHSNGYNYLDWYLQKPGQSPQLLIYLG
STRASGVPDRFSGSGSGTDFTLKINRVEAEDVGVYYCMQALQSPFTFGGGTKVEI
K

FIG. 20N

DIVMTQSPVSLAVTPGEPASISCRSSQSLLHSNGYNYLDWYLQKPGQSPQLLIYLG
STRASGVPDRFSGSGSGTDFTLKINRVEAEDVGVYYCMQALQSPFTFGGGTKVQI
K

FIG. 20O

DIVMTQSPLSLPVTPGEPASISCRSSQSLLHSNGNNYLDWYLQKPGQSPQLLIYLA
SNRASGVPDRFSGSGSGTDFTLKISRVEPEDVGLYYCMQALQTPLTFGGGSKVEI
K

FIG. 20P

DIVMTQSPLSLPVTPGEPASISCRSSQSLLHSNGYNYLDWYLQKPGQSPQLLIYLG
SNRASGVPDRFSGSVSGTDFTLKISRVEAEDVGVYYCMQALQTPITFGQGTRLEIK

FIG. 20Q

DIVMTQSPLSLPVTPGEPASISCRSSQSLLHSNGYNYLDWYLQRPGQSPQLLIYLG
SNRASGVPDRFSGSGSGTDFTLKISRVEAEDVGVYYCMQALQTPPTFGQGTRLEI
K

FIG. 20R

DIVMTQSPLSLPVTPGEPASISCRSSQSLLHSNGYNYLDWYLQKPGQSPQLLIYLG
SNRASGVPDRFSGSGSGTDFTLEISRVEAEDVGVYYCMQALQTPPVTFGQGTRLE
IK

FIG. 20S

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQTRPVTFGQGTRLE
IK

FIG. 20T

DIVMTQSPLSLPVTPGEPASISCRSSQSLLHTNGYNYLDWYLQKPGQSPQLLIYLG
SHRASGVPDRFSGSGSGTDFTLKISRVEAEDVGVYYCMQALQTPITFGQGTRLEIK

FIG. 20U

DIVMTQSPLSLPVTPGEPASISCRSGQSLLHSNGYNYLDWYLQKPGQSPQLLIYLG
SNRASGVPDRFSGSGSGADFTLKISRVEAEDVGVYYCMQALQTPITFGQGTRLEIE

FIG. 20V

DIVMTQSPLSLPVTPGEPASISCRSSQSLLHTNGYNYLDWYVQKPGQSPQLLIYLG
SNRASGVPDRFSGSGSGTDFTLKISRVEAEDVGVYYCMQALQTLITFGQGTRLEI
K

FIG. 20W

DIVMTQSPLSLPVTPGEPASISCRSSQSLLHSNGYNYLDWYLQKPGQSPQLLIYLG
SNRASGVPDRFSGSGSGTDFTLKISRVEAEDIGVYYCMQAQDSPVTFGQGTRLDI
N

FIG. 20X

DIVMTQSPLSLPVTPGEPASISCRSNQSVLHSNGRHYLDWYLQKPGQSPQLLIYM
VFNRASGVPDRFSGSGSGTDFTLKISRVESEDVGVYYCMQAQQTPVTFGQGTRL
DIK

FIG. 20Y

EIVLTQSPGTLSLSPGERATLSCRASQSVGSSYLAWYQQKPGQAPRLLIYGVSSRA
TGIPDRFSGSGSGTDFTLTISRLEPEDFAVYYCQQYGGSPLTFGGGTTVEIK

FIG. 20Z

EIVLTQSPGTLSLSPGERATLSCRASQSVGNNYLAWYQQRPGRAPRLVMYDPSSR
ATGIPDRFSGSGSGTDFTLTISRLEPEDFAVYYCQQYGNSPPTFGGGTKVEIK

FIG. 20AA

EIVLTQSPDTLSLSPGDRATLSCRASQSVSNYLAWYQQKAGRAPSLLIYGTSRRAT
DIPDRFSGSGSGTDFTLTISRLEPEDSAVYYCQQYGSASLTFGGGTKVEIK

FIG. 20BB

EIVLTQSPATLSVSPGERATLSCRASQSVSSYLAWYQQKPGQAPRLLIYDASNRAT
GIPARFSGSGSGTDFTLTISSLEPEDFAVYYCQQRSNWPLTFGQGTKVEIK

FIG. 20CC

EIVLTQSPATLSLSPGERATLSCRASQSVSSYLAWYQQKPGQAPRLLIYDASNRAT
GIPARFSGSGSGTDFTLTISSLEPEDFAVYYCQQRSNWPTFGGGTKVEIK

FIG. 20DD

EIVLTQSPATLSLSPGERATLSCRASQSVRSFLAWYQQKPGQAPRLLIYDTSKRPT
GIPDRFSGSGSGTDFTLTISSLEPEDFAVYYCQQRSSWPLTFGGGTTVEIK

FIG. 20EE

EIVLTQSPATLSLSPGERATLSCRASQSVSSYLAWYQQKPGQAPRLLIYDASNRAT
GIPARFSGSGSGTDFTLTISSLEPEDFAVYYCQQRSNWPPITFGQGTRLEIK

FIG. 20FF

DIQMTQSPSFLSASVGDRVTISCRASQSIDSYINWYQQKPGKAPKLLIYAASSLQR
GVPSRFSGSGSGTDFTLTISSLQPEDFATYYCQQTYSTLTFGGGTKVEIK

FIG. 20GG

QSALTQPASVSGSPGQSITISCTGTSSDVGGYKYVSWYQQHPGKAPKLIIYDVTNR
PSGVSKRFSGSKSGNTASLTISGLQAEDEADYYCSSYTSRSTPVFGGGTKVTVL

FIG. 21A

SSELTQDPAVSVALGQTVRITCQGDSLRSYYASWYQQKPGQAPVLVIYGKNYRP
SGIPDRFSGSSSGNTASLTITGAQAEDEADYYCNSRDSSGNHWVFGGGTKLTVL

FIG. 21B

QLVLTQSPPASASLGASVKLTCTLSSGHSSYAIAWHQQQPEKGPRYLMNLNSDGS
HSKGDGVPDRFSGSSSGAERYLTISSLQSEDEADYYCQSWDTGEVFGGGTKLTVL

FIG. 21C

QAVVTQEPSLTVSPGGTVTLTCDSSTGAVTSGHYPYWLQQKPGQAPRTLIYDTH
NKHSWTPGRFSGSLLGGKAALTLSGAQPEDEAEYYCSLSYSAVWVFGGGTKLTV
L

FIG. 21D

COMPOSITIONS, METHODS AND KITS RELATING TO ANTI-PLATELET AUTOANTIBODIES AND INHIBITORS THEREOF

CROSS-REFERENCE TO RELATED APPLICATIONS

The present application is a continuation of International Patent Application No. PCT/US03/21304, filed Jul. 3, 2003, which is entitled to priority under 35 U.S.C. §119(e), to U.S. Provisional Application No. 60/394,352, filed on Jul. 3, 2002, and U.S. Provisional Application No. 60/411,694, filed on Sep. 18, 2002, all of which applications are hereby incorporated by reference in their entirety herein.

BACKGROUND OF THE INVENTION

Idiopathic thrombocytopenic purpura (ITP) is a common immunohematologic disorder caused by platelet-reactive autoantibodies as described in Bussel et al. (2000, In Hematology: Basic Principle and Practice, pp. 2096-2114, Churchill Livingstone, Philadelphia, Pa.). Briefly, in ITP, the clearance of antibody-coated platelets by tissue macrophages is accelerated, and in some cases, the antibodies also impair platelet production. Childhood-type ITP is self-limiting in about 80% of cases and may be associated with a previous viral infection. Adult-onset ITP is a chronic illness in more than 70% of cases and may occur in association with other disorders, including systemic lupus erythematosus (SLE), lymphoproliferative diseases, common variable immunodeficiency (CVID) disease, and human immunodeficiency virus (HIV) infection.

The decision to treat patients with ITP takes into account the patient's age and disease severity and the anticipated natural history of the disorder. Therapy is initially directed toward impeding the clearance of antibody-coated platelets by using glucocorticoids, splenectomy, anti-blood group D [(anti-Rh(D)] immunoglobulin (Ig), intravenous γ-globulin (IVIG), and other treatments. Immunosuppressive therapy is nonspecific, often toxic, and typically reserved for patients with refractory disease.

Numerous studies have been performed to characterize the pathogenic autoantibodies responsible for platelet destruction and thereby provide a reliable way to diagnose ITP, understand its pathogenesis, and predict responsiveness to therapy. IgG antibodies that react with platelet glycoprotein (GP) IIb/IIIa and GPIb/IX have been identified in some patient serum samples and platelet eluates. See, e.g., van Leeuwen et al. (1982, Blood, 59:23-62), McMillian et al. (1987, Blood 70:1040-1045), Kiefel et al. (1991, Brit. J. Haematol. 79:256-262), and He et al. (1994, Blood 83:1024-1032). However, other platelet antigens also appear to be targeted as described in, e.g., He et al. (1994, Blood 83:1024-1032), Bierling et al. (1994, Brit. J. Haematol. 87:631-633), Hou et al. (1995, Eur. J. Haematol. 55:307-314), Pfueller et al. (1990, Brit. J. Haematol. 74:336-341), Sugiyama et al. (1987, Blood 69:1712-1720), Tomiyama et al. (1992, Blood 79:161-168), Deckmyn et al. (1994, Blood 84:1968-1974), Honda et al. (1990, Brit. J. Haematol. 75:245-249) and Varon et al. (1990, Clin. Immunol. Immunopathol. 54:454-468). In many cases, the antibody specificity cannot be determined or even detected as described in, e.g., Bussel et al. (2000, In Hematology: Basic Principle and Practice, pp. 2096-2114, Churchill Livingstone, Philadelphia, Pa.).

Furthermore, there is no formal proof that any single subset of antibodies, such as, for example, those directed at GPIIb/IIIa, are responsible for platelet destruction. Consequently, previously, the clinical utility of measuring serum or platelet-elutable Ig is unknown and does not have a definitive role in the diagnosis or treatment of ITP or in distinguishing between the adult-onset and childhood-onset forms of the disease as in George et al. (1996, Blood 88:3-40). As a result, the diagnosis of ITP remains one of exclusion and the usefulness of available platelet-antibody tests to confirm or exclude the diagnosis independent of other criteria has not been established (see, e.g., Bussel et al. (2000, In Hematology: Basic Principle and Practice, pp. 2096-2114, Churchill Livingstone, Philadelphia, Pa.).

These prior art limitations illustrate the difficulty involved in characterizing a pathologic autoimmune response by analyzing polyclonal serum. To understand clonality, genetic origin, somatic mutation, and the molecular basis of pathogenicity, repertoires of IgG anti-platelet autoantibodies, e.g., those produced in vitro from the B cells of affected patients, must be studied. Conventional B-cell immortalization approaches for cloning human monoclonal antibodies result in low transformation frequencies and have a propensity for generating IgM-producing clones, thus causing a sampling bias as in Winter et al. (1991, Nature 349:293-299) and Burton et al. (1994, Adv. Immunol. 57:191-280). Consequently, all but one, as in Olee et al. (1997, Brit. J. Haematol. 96:836-845) of the reported human anti-platelet autoantibodies isolated from patients with ITP have been of the IgM class and no more than 2 or 3 unique antibodies have been isolated from a given patient as in Deckmyn et al. (1994, Blood 84:1968-1974), Honda et al. (1990, Brit. J. Haematol. 75:245-249), Nugent et al. (1987, Blood 70:16-22), Hiraiwa et al. (1990, Autoimmunity 8:107-113); and Kunicki et al. (1991, Autoimmunity 4:433-446). Since ITP is an autoimmune disease mediated by platelet autoantibodies of the IgG class, which autoantibodies possess Fc domains and which, unlike antibodies of the IgM class, can interact with receptors on splenic macrophages leading to platelet consumption, the disease relevance of the IgM monoclonals isolated using conventional cell cloning techniques is unclear. Furthermore, the single reported IgG platelet autoantibody derived using cell cloning technique (Olee, above) was found to bind to keyhole limpet hemocyanin as well as to platelet GPIIb/IIIa and demonstrated a three-fold better specificity for tetanus toxoid, thus calling into question the actual specificity of that one purportedly "auto" antibody. As a result, it has been difficult to assess the genetic diversity and other biochemical and immunological properties among ITP-associated autoantibodies within an individual patient, among patients, and in different clinical settings using conventional approaches.

In sum, there are no effective methods of diagnosis or specific treatment modalities for ITP, a disease which causes significant human morbidity and mortality. Despite these long-felt needs, prior obstacles to identifying which, if any, antibodies are potential diagnostic and/or therapeutic targets relating to this disease have prevented development of useful diagnostics and therapeutics for ITP. The present invention meets these needs.

Additionally, platelet aggregation is an essential event in the formation of blood clots. Under normal circumstances, blood clots serve to prevent the escape of blood cells from the vascular system. However, during certain disease states, clots can restrict or totally occlude blood flow resulting in cellular necrosis. For example, platelet aggregation and subsequent thrombosis at the site of an atherosclerotic plaque is an important causative factor in the genesis of conditions such as angina, acute myocardial infarction, and reocclusion following successful thrombolysis and angioplasty.

Heart attack patients are typically treated with thrombolytic agents such as tissue plasminogen activator or streptokinase, which dissolve the fibrin component of clots. A major complication associated with fibrinolysis is reocclusion based on platelet aggregation which can result in further heart damage. Since GPIIb/IIIa receptors are known to be responsible for platelet aggregation, reagents which block the activity of these receptors are expected to reduce or prevent reocclusion following thrombolytic therapy and to accelerate the rate of thrombolysis. Such reagents are also expected to be useful in therapy of other vaso-occlusive and thromboembolic disorders.

One prior art approach to blocking platelet aggregation involves monoclonal antibodies specific for GPIIb/IIIa receptors. A murine monoclonal antibody, designated 7E3, that inhibits platelet aggregation and appears useful in the treatment of human thrombotic diseases is described in published European Patent Application Nos. 205,207 and 206,532, as well as U.S. Pat. No. 5,976,532, to Coller et al. However, it is well-known in the art that murine antibodies have characteristics which severely limit their use in human therapy due to their immunogenicity when administered to a human. Additionally, the need for readministration of such therapeutic modalities in thromboembolic disorders increases the likelihood of these types of immune reactions.

In order to overcome the limitations of administering a mouse antibody to humans, chimeric antibodies consisting of non-human binding regions joined to human constant regions have been produced (e.g., 1984, Proc. Natl. Acad. Sci. USA 81:6851; and PCT Application No. PCT/GB85 00392). However, the technical difficulties associated with such chimeric antibodies (e.g., loss of binding specificity and or avidity, as well as continued immunogenicity when administered to humans) have severely limited their therapeutic applicability in human patients.

Thus, the prior art limitation in production of human anti-platelet autoantibodies, combined with the obstacles in producing murine/human chimeric antibodies to platelet antigens, have prevented the production of human anti-platelet autoantibodies to treat disorders and diseases relating to platelet function, including clotting, despite the long-felt acute need for such therapies. The present invention meets these needs.

BRIEF SUMMARY OF THE INVENTION

The invention includes a method of identifying an anti-platelet autoantibody in a mammal. The method comprises producing an antibody phage display library from B-lymphocytes obtained from the mammal, screening the library to detect a phage that specifically binds with a platelet component, wherein the screening comprises panning the phage on intact platelets using competitive cell-surface panning, thereby identifying the anti-platelet autoantibody in the mammal.

In one aspect, the mammal is a human.

In another aspect, the mammal is afflicted with idiopathic thrombocytopenic purpura.

In yet another aspect, the platelet component is selected from the group consisting of GPIa/IIa, GPIIb/IIIa, and GPIb/IX.

The invention includes an autoantibody identified by this method.

The invention also includes a human monoclonal anti-platelet autoantibody.

In one aspect, the autoantibody is an IgG antibody.

In another aspect, the autoantibody specifically binds with GPIIb/IIIa.

In a further aspect, the autoantibody specifically binds with GPIIb/IIa but does not require the N-terminal portion of $\alpha_{IIb}$ for binding.

In yet a further aspect, the N-terminal portion comprises from about amino acid residue number 1 to about amino acid residue number 446 of the $\alpha_{IIb}$ (GenBank Accession No. P08514; SEQ ID NO:153).

In another aspect, the autoantibody requires a binding portion of GPIIb/IIIa comprising from about amino acid residue number 447 to about amino acid residue number 1009 of $\alpha_{IIb}$ (GenBank Accession No. P08514; SEQ ID NO: 153).

The invention includes an anti-platelet autoantibody wherein the autoantibody is selected from the group consisting of H44L4 [SEQ ID NO:64 (H44) and SEQ ID NO:70 (L4)], H46L16 [SEQ ID NO:66 (H46) and SEQ ID NO:71 (L16)], H48L24 [SEQ ID NO:68 (H48) and SEQ ID NO:72 (L24)], H36L35 [SEQ ID NO:57 (H36) and SEQ ID NO:74 (L35)], H40L36 [SEQ ID NO:61 (H40) and SEQ ID NO:75 (L36)], H83L34 [SEQ ID NO:69 (H83) and SEQ ID NO:73 (L34)], H39L37 [SEQ ID NO:60 (H39) and SEQ ID NO:76 (L37)], H42L38 [SEQ ID NO:63 (H42) and SEQ ID NO:77 (L38)], H38L39 [SEQ ID NO:59 (H38) and SEQ ID NO:78 (L39)], H37L40 [SEQ ID NO:58 (H37) and SEQ ID NO:79 (L40)], H37L41 [SEQ ID NO:58 (H37) and SEQ ID NO:80 (L41)], H40L42 [SEQ ID NO:61 (H40) and SEQ ID NO:81 (142)], H39L43 [SEQ ID NO:60 (H39) and SEQ ID NO:82 (L43)], H37L44 [SEQ ID NO:58 (H37) and SEQ ID NO:83 (L44)], H39L44 [SEQ ID NO:60 (H39) and SEQ ID NO:83 (L44)], H37L45 [SEQ ID NO:58 (H37) and SEQ ID NO:84 (L45)], H39L46 [SEQ ID NO:60 (H139) and SEQ ID NO:85 (L46)], H37L47 [SEQ ID NO:58 (H37) and SEQ ID NO:86 (L47)], H37L48 [SEQ ID NO:58 (H137) and SEQ ID NO:87 (L48)], H38L49 [SEQ ID NO:59 (1138) and SEQ ID NO:88 (L49)], H37L50 [SEQ ID NO:58 (H37) and SEQ ID NO:89 (L50)], H41L51 [SEQ ID NO:62 (H41) and SEQ ID NO:90 (L51)], H40L52 [SEQ ID NO:61 (H40) and SEQ ID NO:91 (L52)], H40L53 [SEQ ID NO:61 (H40) and SEQ ID NO:92 (L53)], H38L54 [SEQ ID NO:59 (H38) and SEQ ID NO:93 (L54)], H38L55 [SEQ ID NO:59 (H38) and SEQ ID NO:94 (L55)], H45L61 [SEQ ID NO:84 (L45) and SEQ ID NO:95 (L61)], H47L63 [SEQ ID NO:67 (H47) and SEQ ID NO:96 (L63)], H47L64 [SEQ ID NO:67 (H47) and SEQ ID NO:97 (L64)], H38L72 [SEQ ID NO:59 (H38) and SEQ ID NO:98 (L72)], H38L74 [SEQ ID NO:59 (H38) and SEQ ID NO:99 (L74)], H38L75 [SEQ ID NO:59 (H38) and SEQ ID NO: 100 (L75)], H38L76 [SEQ ID NO:59 (H38) and SEQ ID NO:101 (L76)], H36L76 [SEQ ID NO:57 (H36) and SEQ ID NO:101 (L76)], H37L92 [SEQ ID NO:58 (H37) and SEQ ID NO:103 (L92)], H29L104 [SEQ ID NO:56 (H29) and SEQ ID NO:104 (L104)], H4L106 [SEQ ID NO:54 (H4) and SEQ ID NO:105 (L106)], and H10L122 [SEQ ID NO:55 (H10) and SEQ ID NO:106 (L122)].

The invention also includes an anti-platelet autoantibody wherein the autoantibody comprises a heavy chain comprising an amino acid sequence selected from the group consisting of SEQ ID NO:54 (H4), SEQ ID NO:55 (H10), SEQ ID NO:56 (H29), SEQ ID NO:57 (H36), SEQ ID NO:58 (H37), SEQ ID NO:59 (H38), SEQ ID NO:60 (H39), SEQ ID NO:61 (H40), SEQ ID NO:62 (H41); SEQ ID NO:63 (H42), SEQ ID NO:64 (H44), SEQ ID NO:65 (H45), SEQ ID NO:66 (H46), SEQ ID NO:67 (H47), SEQ ID NO:68 (H48), and SEQ ID NO:69 (H83).

In one aspect, the autoantibody further comprising a light chain comprising an amino acid sequence selected from the group consisting of SEQ ID NO:70 (L4), SEQ ID NO:71

(L16), SEQ ID NO:72 (L24); SEQ ID NO:73 (L34), SEQ ID NO:74 (L35), SEQ ID NO:75 (L36), SEQ ID NO:76 (L37), SEQ ID NO:77 (L38), SEQ ID NO:78 (L39), SEQ ID NO:79 (L40), SEQ ID NO:80 (L41), SEQ ID NO:81 (L42), SEQ ID NO:82 (L43); SEQ ID NO:83 (L44), SEQ ID NO:84 (L45), SEQ ID NO:86 (L47), SEQ ID NO:87 (L48), SEQ ID NO:88 (L49), SEQ ID NO:89 (L50), SEQ ID NO:90 (L51), SEQ ID NO:91 (L52), SEQ ID NO:92 (L53); SEQ ID NO:93 (L54), SEQ ID NO:94 (L55), SEQ ID NO:95 (L61), SEQ ID NO:96 (L63), SEQ ID NO:97 (L64), SEQ ID NO:98 (L72), SEQ ID NO:99 (L74), SEQ ID NO:100 (L75), SEQ ID NO:101 (L76), SEQ ID NO:102 (L125); SEQ ID NO:103 (L92), SEQ ID NO:104 (L104), SEQ ID NO:105 (L 106), and SEQ ID NO:106 (L122).

In yet another aspect, the heavy chain is H38 (SEQ ID NO:78) and the light chain is selected from the group consisting of L39 SEQ ID NO:78, L54 (SEQ ID NO:93), L55 (SEQ ID NO:94), L72 (SEQ ID NO:98), L74 (SEQ ID NO:99), L75 (SEQ ID NO:100), L76 (SEQ ID NO:101), and L92 (SEQ ID NO:103).

In yet a further aspect, the heavy chain is H37 and the light chain is selected from the group consisting of L40, L41, L44, L45, L47, L48, L50, L93.

The invention includes an anti-platelet autoantibody wherein the autoantibody comprises a light chain comprising an amino acid sequence selected from the group consisting of SEQ ID NO:70 (L4), SEQ ID NO:71 (L16), SEQ ID NO:72 (L24); SEQ ID NO:73 (L34), SEQ ID NO:74 (L35), SEQ ID NO:75 (L36), SEQ ID NO:76 (L37), SEQ ID NO:77 (L38), SEQ ID NO:78 (L39), SEQ ID NO:79 (L40), SEQ ID NO:80 (L41), SEQ ID NO:81 (l42), SEQ ID NO:82 (L43); SEQ ID NO:83 (L44), SEQ ID NO:84 (L45), SEQ ID NO:85 (L46), SEQ ID NO:86 (L47), SEQ ID NO:87 (L48), SEQ ID NO:88 (L49), SEQ ID NO:89 (L50), SEQ ID NO:90 (L51), SEQ ID NO:91 (L52), SEQ ID NO:92 (L53); SEQ ID NO:93 (L54), SEQ ID NO:94 (L55), SEQ ID NO:95 (L61), SEQ ID NO:96 (L63), SEQ ID NO:97 (L64), SEQ ID NO:98 (L72), SEQ ID NO:99 (L74), SEQ ID NO:100 (L75), SEQ ID NO:101 (L76), SEQ ID NO:102 (L125); SEQ ID NO:103 (L92), SEQ ID NO:104 (L104), SEQ ID NO:105 (L106), and SEQ ID NO:106 (L122).

In one aspect, the autoantibody further comprises a heavy chain comprising an amino acid sequence selected from the group consisting of SEQ ID NO:54 (H4), SEQ ID NO:55 (1110), SEQ ID NO:56 (H29), SEQ ID NO:57 (H36), SEQ ID NO:58 (H37), SEQ ID NO:59 (H38), SEQ ID NO:60 (H139), SEQ ID NO:61 (H40), SEQ ID NO:62 (H41); SEQ ID NO:63 (H42), SEQ ID NO:64 (H44), SEQ ID NO:65 (H45), SEQ ID NO:66 (H146), SEQ ID NO:67 (H47), SEQ ID NO:68 (H48), and SEQ ID NO:69 (H83).

In another aspect, the light chain is L76 and the heavy chain is selected from the group consisting of H36 and H38.

The invention includes an isolated nucleic acid encoding an anti-platelet autoantibody.

In one aspect, the isolated nucleic acid encodes a heavy chain and comprises a nucleotide sequence selected from the group consisting of SEQ ID NO: 1 (H4), SEQ ID NO:2 (H10), SEQ ID NO:3 (H29), SEQ ID NO:4 (H36), SEQ ID NO:5 (H37), SEQ ID NO:6 (H38), SEQ ID NO:7 (H39), SEQ ID NO:8 (H40), SEQ ID NO:9 (H41); SEQ ID NO:10 (H42), SEQ ID NO:1 (H44), SEQ ID NO:12 (H45), SEQ ID NO:13 (H46), SEQ ID NO:14 (H47), SEQ ID NO:15 (H48), SEQ ID NO:16 (H83).

In another aspect, the nucleic acid encodes a light chain and comprises a nucleotide sequence selected from the group consisting of SEQ ID NO: 17 (L4), SEQ ID NO:18 (L16), SEQ ID NO:19 (L24); SEQ ID NO:20 (L34), SEQ ID NO:21 (L35), SEQ ID NO:22 (L36), SEQ ID NO:23 (L37), SEQ ID NO:24 (L38), SEQ ID NO:25 (L39), SEQ ID NO:26 (L40), SEQ ID NO:27 (L41), SEQ ID NO:28 (L42), SEQ ID NO:29 (L43); SEQ ID NO:30 (L44), SEQ ID NO:31 (L45), SEQ ID NO:32 (L46), SEQ ID NO:33 (L47), SEQ ID NO:34 (L48), SEQ ID NO:35 (L49), SEQ ID NO:36 (L50), SEQ ID NO:37 (L51), SEQ ID NO:38 (L52), SEQ ID NO:39 (L53); SEQ ID NO:40 (L54), SEQ ID NO:41 (L55), SEQ ID NO:42 (L61), SEQ ID NO:43 (L63), SEQ ID NO:44 (L64), SEQ ID NO:45 (L72), SEQ ID NO:46 (L74), SEQ ID NO:47 (L75), SEQ ID NO:48 (L76), SEQ ID NO:49 (L125); SEQ ID NO:50 (L92), SEQ ID NO:51 (L104), SEQ ID NO:52 (L106), and SEQ ID NO:53 (L122).

In yet another aspect, the nucleic acid encodes a heavy chain comprising an amino acid sequence selected from the group consisting of SEQ ID NO:54 (H4), SEQ ID NO:55 (H10), SEQ ID NO:56 (H29), SEQ ID NO:57 (H36), SEQ ID NO:58 (H37), SEQ ID NO:59 (H38), SEQ ID NO:60 (H39), SEQ ID NO:61 (H40), SEQ ID NO:62 (H41); SEQ ID NO:63 (H42), SEQ ID NO:64 (H44), SEQ ID NO:65 (H45), SEQ ID NO:66 (H46), SEQ ID NO:67 (H47), SEQ ID NO:68 (H48), and SEQ ID NO:69 (H83).

In yet a further aspect, the nucleic acid encodes a light chain comprising an amino acid sequence selected from the group consisting of SEQ ID NO:70 (L4), SEQ ID NO:71 (L116), SEQ ID NO:72 (L24); SEQ ID NO:73 (L34), SEQ ID NO:74 (L35), SEQ ID NO:75 (L36), SEQ ID NO:76 (L37), SEQ ID NO:77 (L38), SEQ ID NO:78 (L39), SEQ ID NO:79 (L40), SEQ ID NO:80 (L41), SEQ ID NO:81 (L42), SEQ ID NO:82 (L43); SEQ ID NO:83 (L44), SEQ ID NO:84 (L45), SEQ ID NO:85 (L46), SEQ ID NO:86 (L47), SEQ ID NO:87 (L48), SEQ ID NO:88 (L49), SEQ ID NO:89 (L50), SEQ ID NO:90 (L51), SEQ ID NO:91 (L52), SEQ ID NO:92 (L53); SEQ ID NO:93 (L54), SEQ ID NO:94 (L55), SEQ ID NO:95 (L61), SEQ ID NO:96 (L63), SEQ ID NO:97 (L64), SEQ ID NO:98 (L72), SEQ ID NO:99 (L74), SEQ BD NO:100 (L75), SEQ ID NO:101 (L76), SEQ ID NO:102 (L125); SEQ ID NO:103 (L92), SEQ ID NO:104 (L104), SEQ ID NO:105 (L106), and SEQ ID NO:106 (L122).

The invention includes a method for inhibiting blood clotting in a mammal having a thrombus or at risk of thrombus formation. The method comprises administering to the mammal an effective amount of an antibody, or a biologically active fragment thereof, that specifically binds with glycoprotein IIb/IIIa, wherein the antibody, or fragment thereof, comprises an antigen binding region derived from an H44L4 anti-platelet autoantibody, thereby inhibiting blood clotting in the mammal.

In one aspect, the method further comprises administering a thrombolytic agent.

In another aspect, the mammal is a human.

The invention includes a method for reversibly inhibiting blood clotting in a mammal having a thrombus or at risk of thrombus formation. The method comprises administering to the mammal an effective amount of an antibody, or a biologically active fragment thereof, that specifically binds with glycoprotein IIb/IIIa, wherein the antibody, or fragment thereof, comprises an antigen binding region derived from an H44L4 anti-platelet autoantibody, thereby inhibiting blood clotting in the mammal. The method further comprises administering to the mammal an effective amount of a peptide inhibitor of the binding with glycoprotein IIb/IIIa, thereby reversibly inhibiting blood clotting in the mammal.

In one aspect, the mammal is a human.

In another aspect, the peptide inhibitor is selected from the group consisting of P4-12 (SEQ ID NO:111), P3-4 (SEQ ID NO:112), P4-7 (SEQ ID NO:113), P4-2a (SEQ ID NO:114).

The invention includes a method of inhibiting binding of an anti-platelet autoantibody with a platelet component. The method comprises contacting the autoantibody with a peptide inhibitor of the binding, thereby inhibiting binding of the anti-platelet autoantibody with the component.

In one aspect, the component is GPIIb/IIIa and further the autoantibody is H44L4 and wherein the peptide inhibitor is selected from the group consisting of P4-12 (SEQ ID NO:111), P3-4 (SEQ ID NO:112), P4-7 (SEQ ID NO:113), P4-2a (SEQ ID NO:114), P73-11 (SEQ ID NO:116), P123-10 (SEQ ID NO:118), P744 (SEQ ID NO:120), P73-10 (SEQ ID NO:122), P74-3 (SEQ ID NO:124), P74-9 (SEQ ID NO:126), P74-5 (SEQ ID NO: 128), P73-9 (SEQ ID NO:130), P124-8 (SEQ ID NO:132), P123-11 (SEQ ID NO:134), P124-1 (SEQ ID NO:136), P73-2 (SEQ ID NO:138), P73-6 (SEQ ID NO: 140), P124-11 (SEQ ID NO: 142), P124-2 (SEQ ID NO: 144), P73-7 (SEQ ID NO: 146), P74-1a (SEQ ID NO:148), P123-8 (SEQ ID NO:150), P74-8 (SEQ ID NO: 152).

The invention also includes a method of inhibiting platelet adhesion in a mammal. The method comprises administering to the mammal an effective amount of an anti-platelet autoantibody, or a biologically active fragment thereof, wherein the autoantibody specifically binds with GPIb/IX thereby inhibiting interaction of the GPIb/IX with a von Willebrand multimer, and where the interaction is required for platelet adhesion, thereby inhibiting platelet adhesion in the mammal.

In one aspect, the mammal is a human.

The invention includes a method of treating thrombotic thrombocytopenic purpura in a mammal. The method comprises administering to the animal an effective amount of an anti-platelet autoantibody, or a biologically active fragment thereof, wherein the autoantibody specifically binds with GPIb/IIIa thereby inhibiting interaction of the GPIb/IX with a von Willebrand multimer, and wherein the interaction is required for platelet adhesion and further wherein the platelet adhesion mediates thrombotic thrombocytopenic purpura in the mammal, thereby treating thrombotic thrombocytopenic purpura in the mammal.

In one aspect, the mammal is a human.

The invention includes a method of inhibiting platelet aggregation. The method comprises contacting a platelet with an effective amount of an anti-platelet autoantibody, or a biologically active fragment thereof.

In one aspect, the autoantibody specifically binds with GPIIb/IIIa.

In another aspect, the autoantibody is H44L4 [SEQ ID NO:64 (H44) and SEQ ID NO:70 (L4)].

The invention further includes a method of inhibiting platelet activation. The method comprises contacting a platelet with an effective amount of an anti-platelet autoantibody, or a biologically active fragment thereof.

The invention includes a method of inhibiting platelet function. The method comprises contacting a platelet with an effective amount of an anti-platelet autoantibody, or a biologically active fragment thereof.

In one aspect, the autoantibody specifically binds with a platelet component selected from the group consisting of GPIa/IIa, GPIIb/IIIa, and GPIb/IX.

The invention includes a method of inhibiting binding of an anti-platelet autoantibody, or a biologically active fragment thereof, with a platelet. The method comprises contacting the autoantibody with an effective amount of a peptide inhibitor, thereby inhibiting binding of the autoantibody with the platelet.

In one aspect, the autoantibody specifically binds with at least one platelet component selected from the group consisting of GPIa/IIa, GPIIb/IIa, and GPIIb/IX.

In another aspect, the peptide inhibitor is selected from the group consisting of P4-12 (SEQ ID NO: 111), P3-4 (SEQ ID NO:112), P4-7 (SEQ ID NO:113), P4-2a (SEQ ID NO:114), P73-11 (SEQ ID NO:116), P123-10 (SEQ ID NO:118), P74-4 (SEQ ID NO:120), P73-10 (SEQ ID NO:122), P74-3 (SEQ ID NO:124), P74-9 (SEQ ID NO:126), P74-5 (SEQ ID NO:128), P73-9 (SEQ ID NO:130), P124-8 (SEQ ID NO:132), P123-11 (SEQ ID NO:134), P124-1 (SEQ ID NO:136), P73-2 (SEQ ID NO:138), P73-6 (SEQ ID NO:140), P124-11 (SEQ ID NO:142), P124-2 (SEQ ID NO:144), P73-7 (SEQ ID NO:146), P74-1a (SEQ ID NO:148), P123-8 (SEQ ID NO:150), P74-8 (SEQ ID NO:152).

The invention includes a method of identifying a peptide that inhibits binding of an anti-platelet autoantibody with a platelet. The method comprises assessing the binding of an anti-platelet autoantibody with a platelet in the presence or absence of a peptide-displaying phage, wherein a lower level of binding of the autoantibody with the platelet in the presence of the peptide displaying phage compared with the binding of the autoantibody with the platelet in the absence of the peptide displaying phage is an indication that the peptide displayed by the peptide displaying phage inhibits binding of the autoantibody with the platelet, thereby identifying a peptide that inhibits binding of an anti-platelet autoantibody with a platelet.

The invention includes a peptide identified by this method.

The invention includes a method of identifying a peptide that inhibits binding of an anti-platelet autoantibody with a platelet component. The method comprises assessing the binding of an anti-platelet autoantibody with a platelet component in the presence or absence of a peptide displaying phage, wherein a lower level of binding of the autoantibody with the platelet component in the presence of the peptide displaying phage compared with the binding of the autoantibody with the platelet component in the absence of the peptide displaying phage is an indication that the peptide displayed by the peptide displaying phage inhibits binding of the autoantibody with the platelet component, thereby identifying a peptide that inhibits binding of an anti-platelet autoantibody with a platelet component. The invention includes a peptide identified by this method.

In one aspect, the platelet component is selected from the group consisting of GPIa/IIa, GPIIb/IIIa, and GPIb/IX.

The invention includes a method of identifying a peptide that binds with an anti-platelet autoantibody. The method comprises contacting a peptide-displaying phage with an anti-platelet autoantibody and detecting whether the phage specifically binds with the autoantibody, thereby identifying a peptide that specifically binds with an anti-platelet autoantibody.

The invention includes a peptide identified by this method.

The invention includes a peptide that specifically binds with an anti-platelet autoantibody.

The invention also includes a method of treating idiopathic thrombocytopenic purpura (ITP) in a mammal. The method comprises administering to an animal afflicted with ITP an effective amount of a compound that specifically kills a B-lymphocyte expressing VH3-30, thereby treating the ITP in the mammal.

In one aspect, the mammal is a human.

In another aspect, the compound is selected from Staphylococcal Protein A (SpA) and an immunotoxin comprising an antibody portion that specifically binds with VH3-30.

The invention includes a kit for inhibiting blood clotting. The kit comprises an effective amount of an anti-platelet autoantibody, or a biologically active fragment thereof, that specifically binds with glycoprotein IIb/IIIa, wherein the autoantibody, or fragment thereof, comprises an antigen binding region derived from an H44L4 anti-platelet autoantibody. The kit further comprises an applicator and an instructional material for use thereof.

The invention includes a kit for reversibly inhibiting blood clotting. The kit comprises an effective amount of an anti-platelet autoantibody, or a biologically active fragment thereof, that specifically binds with glycoprotein IIb/IIIa, wherein the autoantibody, or fragment thereof, comprises an antigen binding region derived from an H44L4 anti-platelet autoantibody. The kit further comprises a peptide inhibitor of the binding with glycoprotein IIb/IIIa, and the kit also comprising an applicator and an instructional material for use thereof.

The invention includes a kit for inhibiting platelet aggregation. The kit comprises an effective amount of an anti-platelet autoantibody, or a biologically active fragment thereof. The kit further comprises an applicator and an instructional material for use thereof.

The invention also includes a kit for inhibiting platelet function. The kit comprises contacting an effective amount of an anti-platelet autoantibody, or a biologically active fragment thereof. The kit further comprises an applicator and an instructional material for use thereof.

The invention includes a kit for inhibiting platelet activation. The kit comprises contacting an effective amount of an anti-platelet autoantibody, or a biologically active fragment thereof. The kit further comprises an applicator and an instructional material for use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising of FIGS. 2A through 2D, depicts an alignment of clonally related platelet autoantibody heavy-chain amino acid sequences and their putative ontogenic trees. The H and L nomenclature is the same as in FIG. 1. FIG. 2A depicts groups of related sequences comprising expanded heavy-chain clones in each patient library (clone A and clone B) enclosed in boxes. For clone A, the putative intermediate heavy-chain sequences are also shown (1, 2, and 3 asterisks, SEQ ID NO: 180, 181, and 182, respectively). FIG. 2A depicts a comparison of the following sequences: 1-02 ?D JH4b (SEQ ID NO:153), H4 (SEQ ID NO:54), 1-46 D5-5 JH3b (SEQ ID NO:154), H10 (SEQ ID NO:55), 3-21 D3-22 JH4b (SEQ ID NO:155), H29 (SEQ ID NO:56), clone B (SEQ ID NO:156), H36 (SEQ ID NO:57), H37 (SEQ ID NO:58), H38 (SEQ ID NO:59), H39 (SEQ ID NO:60), H40 (SEQ ID NO:61), H41 (SEQ ID NO:62), H42 (SEQ ID NO:63), 3-30 ?D JH4b (SEQ ID NO:157), H44 (SEQ ID NO:64), clone A (SEQ ID NO:158), H48 (SEQ ID NO:68), H45 (SEQ ID NO:65), H46 (SEQ ID NO:66), H47 (SEQ ID NO:67), 4-59 ?D JH6b (SEQ ID NO:159), H83 (SEQ ID NO:69). The number of nucleotide differences from germline $V_H$ is tabulated to the right of each sequence. Because D segments showed poor homology with known D genes, mutations were not scored in these regions. Replacement mutations are indicated by letters, identities as ".", and insertions as -, and + to maintain spacing due to variability in CDR3 length. Sequences derived from the 5' V-region primers used for library construction as in Siegel et al. (1997, J. Immunol. Methods 206:73-85) are marked as >. CDR-region designations are according to the system of Kabat et al. (1991, U.S. Dept. of Health and Human Services, National Institutes of Health; NIH Publication number 91-3242); numbering and hypervariable loop designations are according to the system of Chothia et al. (1992, J. Mol. Biol. 227:799-817). FIG. 2B is a diagram depicting the analysis of nucleotide data in each patient and demonstrates a distinct set of somatically mutated heavy chains sharing common $V_HDJ_H$ rearrangements of $V_{H3-30}$, D1-26, and $J_{H4b}$ gene segments. Circles represent isolated and sequenced clones FIGS. 1 and 2A); diamonds (for ITP patient A only) represent putative intermediates. For each member of a patient's clone, the number of nucleotide mutations from its germline $V_H$ gene is shown in parentheses, and the resulting number of replacement (R) or silent mutations (S) is shown in brackets. For each patient clone ontogenic tree, the distance in the horizontal direction represents the extent of mutation from the proposed germline origin within the constraints of the diagram. FIG. 2C depicts a set of aligned amino acid sequences for anti-platelet autoantibody x light-chain clones in each patient library (clone A and clone B); the figure legend is as set forth for FIG. 2A, supra. FIG. 2C depicts a comparison of the following sequences: 012/02 JK4 (SEQ ID NO:160), A20 JK4 (SEQ ID NO:161), L8 JK4 (SEQ ID NO:162), A19/A3 JK1 (SEQ ID NO:163), A19/A3 JK2 (SEQ ID NO:164), A19/A3 JK3 (SEQ ID NO:165), A19/A3 JK4 (SEQ ID NO:166), A19/A3 JK5 (SEQ ID NO:167), A27 JK4 (SEQ ID NO:168), L6 JK1 (SEQ ID NO:169), L6 JK4 (SEQ ID NO:170), L6 JK5 (SEQ ID NO:171), L4 (SEQ ID NO:70), L16 (SEQ ID NO:71), L24 (SEQ ID NO:72), L34 (SEQ ID NO:73), L35 (SEQ ID NO:74), L36 (SEQ ID NO:75), L37 (SEQ ID NO:76), L38 (SEQ ID NO:77), L39 (SEQ ID NO:78), L40 (SEQ ID NO:79), L41 (SEQ ID NO:80), L42 (SEQ ID NO:81), L43 (SEQ ID NO:82), L44 (SEQ ID NO:83), L45 (SEQ ID NO:84), L46 (SEQ ID NO:85), L47 (SEQ ID NO:86), L48 (SEQ ID NO:87), L49 (SEQ ID NO:88), L50 (SEQ ID NO:89), L51 (SEQ ID NO:90), L52 (SEQ ID NO:91), L53 (SEQ ID NO:92), L54 (SEQ ID NO:93), L55 (SEQ ID NO:94), L61 (SEQ ID NO:95), L63 (SEQ ID NO:96), L64 (SEQ ID NO:97), L72 (SEQ ID NO:98), L74 (SEQ ID NO:99), L75 (SEQ ID NO:100), and L76 (SEQ ID NO:101). FIG. 2D depicts a set of aligned amino acid sequences for anti-platelet autoantibody λ light-chain clones in the patient library (clone B); the figure legend is as set forth for FIG. 2A, supra. FIG. 2D depicts a comparison of the following sequences: 2a2 JL2/JL3a (SEQ ID NO:172), 31 JL3b (SEQ ID NO:173), 4b JL2/JL3a (SEQ ID NO:174), 7b*JL3b (SEQ ID NO:175), L92 (SEQ ID NO:103), L104 (SEQ ID NO:104), L106 (SEQ ID NO:105), and L122 (SEQ ID NO:106).

FIG. 3, comprising of FIGS. 3A and 3B, demonstrate platelet autoantibody specificity by ELISA and flow cytometry.

FIG. 5, comprising FIGS. 5A and 5B, depicts data demonstrating platelet binding of randomized light chains paired with platelet autoantibody heavy-chain H44. The heavy chain of GPIIb/IIIa-specific H44L4 was paired again with a library of more than $10^6$ light chains derived from the original, unselected ITP patient A library, and 101 resorted clones were screened for platelet binding by flow cytometry. FIG. 5A depicts a matrix illustrating the genetic composition of the single retrieved positive resorted clone (designated H44L125), which exhibited a mean fluorescence value of 243. For comparison, 20 (of the 100) randomly chosen negative clones (designated H44L126 through H44L145) and the original H44L4 antibody were tabulated. Numbers in shaded boxes represent mean fluorescent intensities. Note that the single positive platelet-binding clone comprises a light chain derived from the same Ig light-chain gene as the original L4 light chain (012/02), yet no other 012/02-encoded light chain (e.g., L125-L128) conferred binding when paired with H44. FIG. 5B depicts a sequence analysis of the cohort of 012/02-encoded light chains retrieved in resorting experiment demonstrating that light-chain L125, which reconstituted platelet binding, may be clonally related to the original L4 light chain because of a distinctive VJ junction characterized by loss of an entire amino acid residue at position 95 (boldface region). FIG. 5B depicts a comparison of the following sequences: 012/02 JK4 (SEQ ID NO:161), L4 (SEQ ID NO:70), L125 (SEQ ID NO:176), L126 (SEQ ID NO:177), L127 (SEQ ID NO:178), L128 (SEQ ID NO:179).

FIG. 6, comprising FIG. 6A depicts flow cytograms comparing the fluorescence intensities of the 3 index antibodies. FIG. 6B depicts a matrix showing that only reconstituted original heavy-chain-light-chain pairs conferred platelet binding. Numbers in boxes represent mean fluorescent intensities.

FIG. 9, comprising FIGS. 9A and 9B, depicts a peptide sequence comparison of the peptidomimetic inhibitors of platelet autoantibody H44L4 binding to human GPIIb/IIIa, that is, the peptide inhibitors bind to the antibody preventing it from binding to GPIIb/IIIa. FIG. 9A depicts the amino acid sequences of the following peptide inhibitors: P4-12 (SEQ ID NO:111); P3-4 (SEQ ID NO:112); P4-7 (SEQ ID NO:113); P4-2a (SEQ ID NO:114); P73-11 (SEQ ID NO:116); P123-10 (SEQ ID NO:118); P74-4 (SEQ ID NO:120); P73-10 (SEQ ID NO:122); P74-3 (SEQ ID NO:124); P74-9 (SEQ ID NO:126); P74-5 (SEQ ID NO:128); P73-9 (SEQ ID NO:130); P124-8 (SEQ ID NO:132); P123-11 (SEQ ID NO:134); P124-1 (SEQ ID NO:136); P73-2 (SEQ ID NO:138); P73-6 (SEQ ID NO:140); P124-11 (SEQ ID NO:142); P124-2 (SEQ ID NO:144); P73-7 (SEQ ID NO:146); P74-1a (SEQ ID NO:148); P123-8 (SEQ ID NO: 150); P74-8 (SEQ ID NO: 152). FIG. 9B depicts the nucleotide sequence of the following peptide inhibitors: P4-12 (SEQ ID NO:107); P3-4 (SEQ ID NO:108); P4-7 (SEQ ID NO: 109); P4-2a (SEQ ID NO:110); P73-11 (SEQ ID NO:115); P123-10 (SEQ ID NO:117); P74-4 (SEQ ID NO:119); P73-10 (SEQ ID NO:121); P74-3 (SEQ ID NO:123); P74-9 (SEQ ID NO:125); P74-5 (SEQ ID NO:127); P73-9 (SEQ ID NO:129); P124-8 (SEQ ID NO:131); P123-11 (SEQ ID NO:133); P124-1 (SEQ ID NO:135); P73-2 (SEQ ID NO:137); P73-6 (SEQ ID NO:139); P124-11 (SEQ ID NO:141); P124-2 (SEQ ID NO:143); P73-7 (SEQ ID NO:145); P74-1a (SEQ ID NO:147); P123-8 (SEQ ID NO:149); P74-8 (SEQ ID NO:151).

FIG. 13, comprising

FIG. 16A depicts the nucleotide sequence of heavy chain H4 (SEQ ID NO:1). FIG. 16B depicts the nucleotide sequence of heavy chain H10 (SEQ ID NO:2).

FIG. 16C depicts the nucleotide sequence of heavy chain H29 (SEQ ID NO:3). FIG. 16D depicts the nucleotide sequence of heavy chain H36 (SEQ ID NO:4).

FIG. 16E depicts the nucleotide sequence of heavy chain H37 (SEQ ID NO:5). FIG. 16F depicts the nucleotide sequence of heavy chain H38 (SEQ ID NO:6). FIG. 16G depicts the nucleotide sequence of heavy chain H39 (SEQ ID NO:7). FIG. 16H depicts the nucleotide sequence of heavy chain H40 (SEQ ID NO:8). FIG. 16I depicts the nucleotide sequence of heavy chain H41 (SEQ ID NO:9). FIG. 16J depicts the nucleotide sequence of heavy chain H42 (SEQ ID NO: 10). FIG. 16K depicts the nucleotide sequence of heavy chain H44 (SEQ ID NO: 11). FIG. 16L depicts the nucleotide sequence of heavy chain H45 (SEQ ID NO: 12).

FIG. 16M depicts the nucleotide sequence of heavy chain H46 (SEQ ID NO: 13). FIG. 16N depicts the nucleotide sequence of heavy chain H47 (SEQ ID NO:14). FIG. 16O depicts the nucleotide sequence of heavy chain H48 (SEQ ID NO: 15). FIG. 16P depicts the nucleotide sequence of heavy chain H83 (SEQ ID NO:16).

FIG. 17A depicts the nucleotide sequence of light chain L4 (SEQ ID NO: 17). FIG. 17B depicts the nucleotide sequence of light chain L16 (SEQ ID NO: 18). FIG. 17C depicts the nucleotide sequence of light chain L24 (SEQ ID NO:19). FIG. 17D depicts the nucleotide sequence of light chain L34 (SEQ ID NO:20). FIG. 17E depicts the nucleotide sequence of light chain L35 (SEQ ID NO:21). FIG. 17F depicts the nucleotide sequence of light chain L36 (SEQ ID NO:22). FIG. 17G depicts the nucleotide sequence of light chain L37 (SEQ ID NO:23). FIG. 17H depicts the nucleotide sequence of light chain L38 (SEQ ID NO:24). FIG. 17I depicts the nucleotide sequence of light chain L39 (SEQ ID NO:25). FIG. 17J depicts the nucleotide sequence of light chain L40 (SEQ ID NO:26). FIG. 17K depicts the nucleotide sequence of light chain L41 (SEQ ID NO:27). FIG. 17L depicts the nucleotide sequence of light chain L42 (SEQ ID NO:28). FIG. 17M depicts the nucleotide sequence of light chain L43 (SEQ ID NO:29). FIG. 17N depicts the nucleotide sequence of light chain L44 (SEQ ID NO:30). FIG. 17O depicts the nucleotide sequence of light chain L45 (SEQ ID NO:31). FIG. 17P depicts the nucleotide sequence of light chain L46 (SEQ ID NO:32). FIG. 17Q depicts the nucleotide sequence of light chain L47 (SEQ ID NO:33). FIG. 17R depicts the nucleotide sequence of light chain L48 (SEQ ID NO:34). FIG. 17S depicts the nucleotide sequence of light chain L49 (SEQ ID NO:35). FIG. 17T depicts the nucleotide sequence of light chain L50 (SEQ ID NO:36). FIG. 17U depicts the nucleotide sequence of light chain L51 (SEQ ID NO:37). FIG. 17V depicts the nucleotide sequence of light chain L52 (SEQ ID NO:38). FIG. 17W depicts the nucleotide sequence of light chain L53 (SEQ ID NO:39). FIG. 17X depicts the nucleotide sequence of light chain L54 (SEQ ID NO:40). FIG. 17Y depicts the nucleotide sequence of light chain L55 (SEQ ID NO:41). FIG. 17Z depicts the nucleotide sequence of light chain L61 (SEQ ID NO:42). FIG. 17AA depicts the nucleotide sequence of light chain L63 (SEQ ID NO:43). FIG. 17BB depicts the nucleotide-sequence of light chain L64 (SEQ ID NO:44). FIG. 17CC depicts the nucleotide sequence of light chain L72 (SEQ ID NO:45). FIG. 17DD depicts the nucleotide sequence of light chain L74 (SEQ ID NO:46). FIG. 17EE depicts the nucleotide sequence of light chain L75 (SEQ ID NO:47). FIG. 17FF depicts the nucleotide sequence of light chain L76 (SEQ ID NO:48). FIG. 17GG depicts the nucleotide sequence of light chain L125 (SEQ ID NO:49).

FIG. 18A depicts the nucleotide sequence of light chain L92 (SEQ ID NO:50). FIG. 18B depicts the nucleotide sequence of light chain L104 (SEQ ID NO:51). FIG. 18C depicts the nucleotide sequence of light chain L106 (SEQ ID NO:52). FIG. 18D depicts the nucleotide sequence of light chain L122 (SEQ ID NO:53).

FIG. 19A depicts the amino acid sequence of heavy chain H4 (SEQ ID NO:54). FIG. 19B depicts the amino acid sequence of heavy chain H10 (SEQ ID NO:55). FIG. 19C depicts the amino acid sequence of heavy chain H29 (SEQ ID NO:56). FIG. 19D depicts the amino acid sequence of heavy chain H36 (SEQ ID NO:57). FIG. 19E depicts the amino acid sequence of heavy chain H37 (SEQ ID NO:58). FIG. 19F depicts the amino acid sequence of heavy chain H38 (SEQ ID NO:59). FIG. 19G depicts the amino acid sequence of heavy chain H39 (SEQ ID NO:60). FIG. 19H depicts the amino acid sequence of heavy chain H40 (SEQ ID NO:61). FIG. 19I depicts the amino acid sequence of heavy chain H41 (SEQ ID NO:62). FIG. 19J depicts the amino acid sequence of heavy chain H42 (SEQ ID NO:63). FIG. 19K depicts the amino acid sequence of heavy chain H44 (SEQ ID NO:64). FIG. 19L depicts the amino acid sequence of heavy chain H45 (SEQ ID NO:65). FIG. 19M depicts the amino acid sequence of heavy chain H46 (SEQ ID NO:66). FIG. 19N depicts the amino acid sequence of heavy chain H47 (SEQ ID NO:67). FIG. 19O depicts the amino acid sequence of heavy chain H48 (SEQ ID NO:68). FIG. 19P depicts the amino acid sequence of heavy chain H83 (SEQ ID NO:69).

FIG. 20A depicts the amino acid sequence of light chain L4 (SEQ ID NO:70). FIG. 20B depicts the amino acid sequence of light chain L16 (SEQ ID NO:71). FIG. 20C depicts the amino acid sequence of light chain L24 (SEQ ID NO:72). FIG. 20D depicts the amino acid sequence of light chain L34 (SEQ ID NO:73). FIG. 20E depicts the amino acid sequence of light chain L35 (SEQ ID NO:74). FIG. 20F depicts the amino acid sequence of light chain L36 (SEQ ID NO:75). FIG. 20G depicts the amino acid sequence of light chain L37 (SEQ ID NO:76). FIG. 20H depicts the amino acid sequence of light chain L38 (SEQ ID NO:77). FIG. 20I depicts the amino acid sequence of light chain L39 (SEQ ID NO:78). FIG. 20J depicts the amino acid sequence of light chain L40 (SEQ ID NO:79). FIG. 20K depicts the amino acid sequence of light chain L41 (SEQ ID NO:80). FIG. 20L depicts the amino acid sequence of light chain L42 (SEQ ID NO:81). FIG. 20M depicts the amino acid sequence of light chain L43 (SEQ ID NO:82). FIG. 20N depicts the amino acid sequence of light chain L44 (SEQ ID NO:83). FIG. 20O depicts the amino acid sequence of light chain L45 (SEQ ID NO:84). FIG. 20P depicts the amino acid sequence of light chain L46 (SEQ ID NO:85). FIG. 20Q depicts the amino acid sequence of light chain L47 (SEQ ID NO:86). FIG. 20R depicts the amino acid sequence of light chain L48 (SEQ ID NO:87). FIG. 20S depicts the amino acid sequence of light chain L49 (SEQ ID NO:88). FIG. 20T depicts the amino acid sequence of light chain L50 (SEQ ID NO:89). FIG. 20U depicts the amino acid sequence of light chain L51 (SEQ ID NO:90). FIG. 20V depicts the amino acid sequence of light chain L52 (SEQ ID NO:91). FIG. 20W depicts the amino acid sequence of light chain L53 (SEQ ID NO:92). FIG. 20X depicts the amino acid sequence of light chain L54 (SEQ ID NO:93). FIG. 20Y depicts the amino acid sequence of light chain L55 (SEQ ID NO:94). FIG. 20Z depicts the amino acid sequence of light chain L61 (SEQ ID NO:95). FIG. 20AA depicts the amino acid sequence of light chain L63 (SEQ ID NO:96). FIG. 20BB depicts the amino acid sequence of light chain L64 (SEQ ID NO:97). FIG. 20CC depicts the amino acid sequence of light chain L72 (SEQ ID NO:98). FIG. 20DD depicts the amino acid sequence of light chain L74 (SEQ ID NO:99). FIG. 20EE depicts the amino acid sequence of light chain L75 (SEQ ID NO: 100). FIG. 20FF depicts the amino acid sequence of light chain L76 (SEQ ID NO:101). FIG. 20GG depicts the amino acid sequence of light chain L125 (SEQ ID NO:102).

FIG. 21A depicts the amino acid sequence of light chain L92 (SEQ ID NO:103). FIG. 21B depicts the amino acid sequence of light chain L104 (SEQ ID NO:104). FIG. 21C depicts the amino acid sequence of light chain L106 (SEQ ID NO:105). FIG. 21D depicts the amino acid sequence of light chain L122 (SEQ ID NO:106).

DETAILED DESCRIPTION OF THE INVENTION

Definitions

Figure 1:
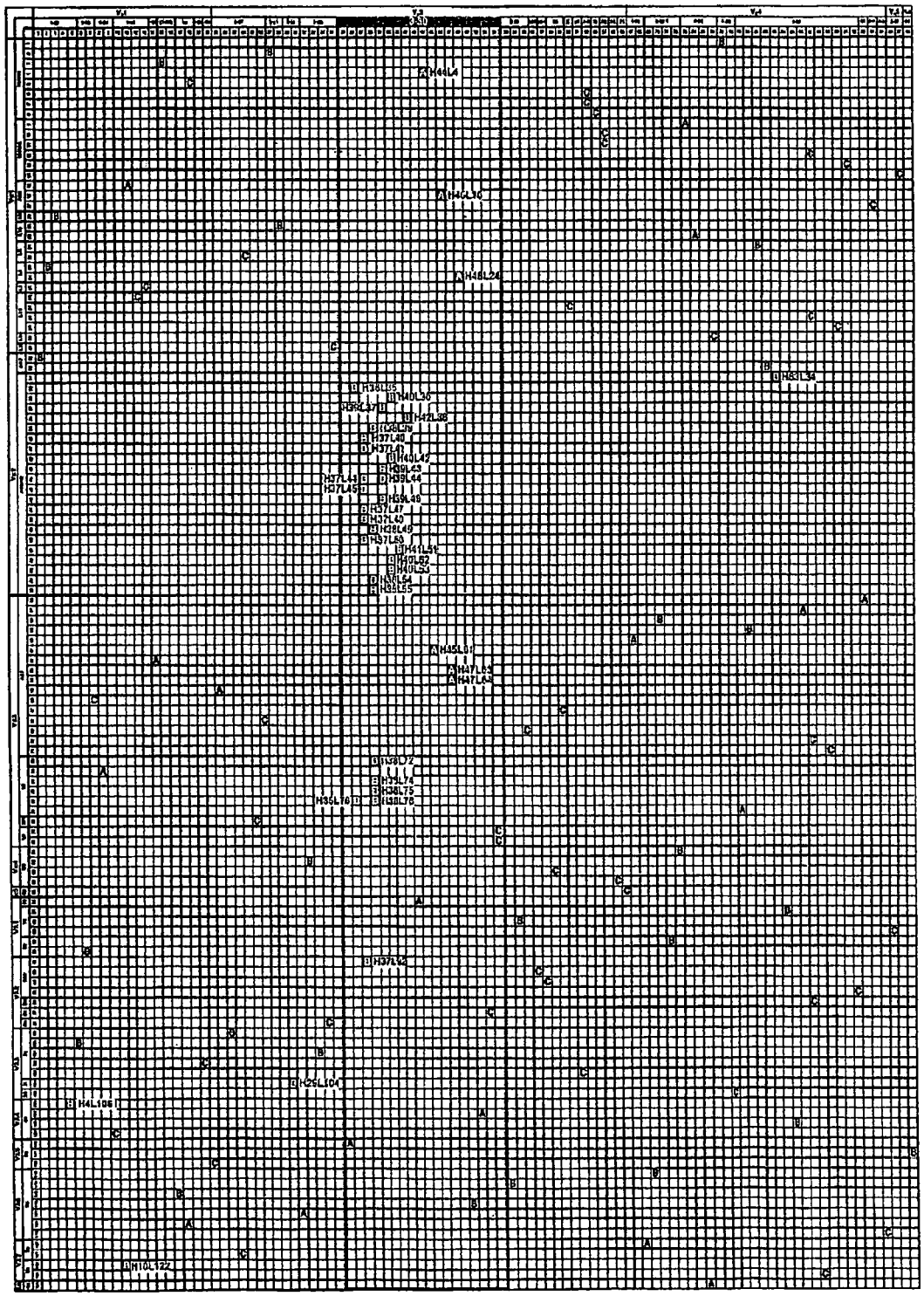
FIG. 1 depicts a matrix illustrating the genetic composition of platelet autoantibodies. The horizontal axis represents the unique γ heavy chains (H01 through H98) and the vertical axis represents the unique κ and γ light chains (L01 through L124) used by antibodies cloned and sequenced from the patients with ITP and the control patient. The letter at the intersection of a heavy-chain-light-chain pair indicates the composition of a platelet-reactive (black box) or platelet-unreactive (white box) antibody isolated from ITP patient A or patient B or control patient C. For positive clones, heavy (H) and light (L) chain designations are indicated. The order of heavy chains (left to right) and light chains (top to bottom) was determined using multiple alignments based on amino acid similarity and then grouped by putative Ig variable-region germline gene and germline gene family. Note the marked predominant use of the VH3-30 germline gene to encode platelet-binding antibodies in both patient A and B repertoires (boxed area towards the middle of the grid).

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |

-continued

| Full Name | Three-Letter Code | One-Letter Code |
|---|---|---|
| Phenylalanine | Phe | F |
| Tryptophan | Trp | W |

By "platelet activation," as the term is used herein, is meant the biological characteristics associated with platelet function in, inter alia, clot formation. The biological characteristics associated with platelet activation include, but are not limited to, structural changes in certain membrane components that lead to their interaction with other substances (e.g., fibrinogen, von Willebrand factor, collagen, and the like), the release of various intracellular materials from storage granules (e.g., serotonin, fibrinogen, ADP, various enzymes, among other things), the expression of additional receptors on the platelet surface (e.g., P-selectin, annexin, and the like), and initiation of enzymes and other components in a series of intracellular signaling pathways.

As used herein, to "alleviate" a disease means reducing the severity of one or more symptoms of the disease.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

An "anti-platelet autoantibody," also referred to herein as an "autoantibody," refers to an antibody in an animal that specifically binds with a platelet, or a component thereof, in that same animal or in an animal of the same species.

Autoimmune diseases and their associated antigens to which autoantibodies may be isolated include, but are not limited to the following: Myasthenia gravis (acetylcholine receptor; neurons), chronic inflammatory demyelinating polyneuropathy (myelin; neurons), autoimmune thyroid disease (thyroid stimulating hormone receptor; thyroid cells), primary biliary cirrhosis (mitochondrial autoantigens; liver mitochondria), idiopathic thrombocytopenic purpura (platelet membrane integrins; platelets, as disclosed elsewhere herein), pemphigus vulgaris (epidermal antigens; epidermis), and Goodpasture's syndrome (basement membrane antigens; kidney or lung cells), among others.

Platelet "component," as used herein, includes any molecule present in or on a platelet, or associated therewith. More preferably, a platelet component means a glycoprotein (e.g., GPIa/IIa, GPIIb/IIIa, GPIb/IX, among others) present on the platelet surface, which can specifically bind with, and/or interact with, another component, e.g., fibrinogen, an antiplatelet autoantibody, and the like.

By the term "applicator," as the term is used herein, is meant any device including, but not limited to, a hypodermic syringe, a pipette, and the like, for administering the autoantibody or peptide inhibitor of the invention to a cell, a tissue, or an animal (e.g., a mammal, such as a human).

Inhibition of platelet "aggregation", as the term is used herein, includes any detectable decrease in the level of platelet aggregation, i.e., where at least two platelets bind with each other, following contacting a platelet with a compound, compared with the aggregation of otherwise identical platelets not so contacted. Platelet aggregation may be mediated by interactions between a platelet component, e.g., a glycoprotein on the platelet surface, with another component, e.g., fibrinogen. A compound that prevents or inhibits these interactions can serve to inhibit platelet aggregation.

"Biologically active fragment," as that term is used herein, means that the portion of the anti-platelet autoantibody from which the fragment is derived, can specifically bind with the antigen that the full-length autoantibody binds and that such binding results in a similar, if not identical, effect as the binding of the full-length autoantibody with the antigen. One such fragment includes, but is not limited to, a portion of a full-length antibody which lacks the CH2 and CH3 constant region domains of the full-length antibody (i.e., the Fc portion) so as to maintain platelet binding of the fragment while eliminating the Fc receptor binding to macrophages, and other cells bearing an Fc receptor, and thereby avoiding platelet destruction that would otherwise result due to Fc receptor binding.

A "biological activity" of an anti-platelet autoantibody, or a biologically active fragment thereof, should be construed, but not be limited to, include the ability of the autoantibody to bind specifically with a platelet component, activate a platelet, promote the clearance of a platelet by a macrophage, induce or inhibit platelet aggregation, induce or inhibit platelet serotonin release, induce or inhibit platelet binding with fibrinogen, inhibit platelet binding with von Willebrand factor, inhibit platelet binding with collagen, and the like.

As used herein, the term "fragment" as applied to a nucleic acid, may ordinarily be at least about 20 nucleotides in length, preferably, at least about 30 nucleotides, more typically, from about 40 to about 50 nucleotides, preferably, at least about 50 to about 80 nucleotides, even more preferably, at least about 80 nucleotides to about 90 nucleotides, yet even more preferably, at least about 90 to about 100, even more preferably, at least about 100 nucleotides to about 150 nucleotides, yet even more preferably, at least about 150 to about 200, even more preferably, at least about 200 nucleotides to about 250 nucleotides, yet even more preferably, at least about 250 to about 300, more preferably, from about 300 to about 350 nucleotides, preferably, at least about 350 to about 360 nucleotides, and most preferably, the nucleic acid fragment will be greater than about 365 nucleotides in length.

As used herein, the term "fragment" as applied to a polypeptide, may ordinarily be at least about 20 amino acids in length, preferably, at least about 30 amino acids, more typically, from about 40 to about 50 amino acids, preferably, at least about 50 to about 80 amino acids, even more preferably, at least about 80 amino acids to about 90 amino acids, yet even more preferably, at least about 90 to about 100, even more preferably, at least about 100 amino acids to about 120 amino acids, and most preferably, the amino acid fragment will be greater than about 123 amino acids in length.

By "inhibition of blood clotting," as used herein, is meant any detectable decrease in the level of thrombus formation, as detected by any available assay. Such assay for blood clotting includes, but is not limited to, measuring bleeding time in vivo as well as assessing platelet functional activity ex vivo, e.g., by assessing the ability of platelets to respond to known platelet agonists (e.g., ADP, epinephrine, thrombin, collagen), to aggregate, to adhere, and/or to secrete the contents of intracellular granules contained therein.

"Ihibiting platelet function," as used herein, means any detectable decrease in the level of platelet function upon contacting a platelet with a compound, when compared with that same platelet function in the platelet prior to being contacted, or in an otherwise identical platelet that is not contacted with the compound.

Platelet "function", in turn, means any biological activity associated with a platelet. Such activity includes, but is not limited to, the formation of platelet aggregates, platelet binding to von Willebrand Factor, collagen, and other substances, the adherence of platelets to endothelial cells, and the secretion of various substances from intracellular stores (e.g., serotonin, and the like).

The term "inhibition of platelet activation," as the term is used herein, means any detectable decrease in the level of platelet activation.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "effective amount" of an anti-platelet autoantibody, as the term is used herein, means an amount of an anti-platelet autoantibody that when a platelet is contacted with the autoantibody, produces a detectable effect on a platelet function and/or biological activity or characteristic. Such effect can be assessed using a variety of assays either disclosed herein, known in the art, or to be developed. A characteristic and/or biological activity that is assessed includes, but is not limited to, the ability of the platelet to aggregate, secrete serotonin, or other intracellular substance, bind fibrinogen, form a clot, adhere to collagen-coated surfaces, and the like.

Likewise, the term "effective amount," as it relates to a peptide inhibitor, means an amount of a peptide inhibitor that when contacted with an anti-platelet autoantibody, will detectably inhibit binding of the autoantibody with a platelet, or a component thereof. The level of binding of the peptide with the autoantibody, as well as the level of binding of the autoantibody with the platelet, or component thereof, in the presence or absence of the peptide inhibitor can be readily assessed using the methods disclosed herein, those well-known in the art, or such methods as are developed in the future.

The skilled artisan would understand that the effective amount varies and can be readily determined based on a number of factors such as the disease or condition being treated, the age and health and physical condition of the mammal being treated, the severity of the disease, the particular compound being administered, and the like. Generally, the effective amount will be set between about 0.1 mg/kg to about 100 mg/kg, more preferably from about 1 mg/kg and 25 mg/kg. The compound (e.g., an anti-platelet autoantibody, or biologically active fragment thereof, a peptide inhibitor, and the like) can be administered through intravenous injection, including, among other things, a bolus injection. However, the invention is not limited to this method of administration.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC3' and 5'TATGGC3' share 50% homology.

By the term "a peptide inhibitor" of binding of an antiplatelet autoantibody with a platelet, or component of a platelet (e.g., a purified GPIa/IIa, GPIIb/IIIa, GPIb/IX, and the like), is meant any peptide that when administered in the presence of the autoantibody and a platelet, detectably decreases the level of autoantibody binding with the platelet, or a component thereof. Although relatively small peptides, e.g., linear 12-mers and C7C constrained 9-mers, are exemplified elsewhere herein, the invention is not limited to these, or any particular, peptides. Instead, the peptides can range from about 5 to about 20 amino acid residues in length.

"Instructional material," as that term is used herein, includes a publication, a recording, a diagram, or any other medium of expression which can be used to communicate the usefulness of the nucleic acid, peptide, and/or compound of the invention in the kit for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the nucleic acid, peptide, and/or compound of the invention or be shipped together with a container which contains the nucleic acid, peptide, and/or compound. Alternatively, the instructional material may be shipped separately from the container with the intention that the recipient uses the instructional material and the compound cooperatively.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids that have been substantially purified from other components that naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA that is part of a hybrid gene encoding additional polypeptide sequence.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene that is expressed in a recombinant host cell wherein the gene comprises a recombinant polynucleotide, produces a "recombinant polypeptide."

A "recombinant polypeptide" is one that is produced upon expression of a recombinant polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

A "receptor" is a compound that specifically binds with a ligand.

By the term "specifically binds," as used herein, is meant a compound, e.g., a protein, a nucleic acid, an antibody, and the like, which recognizes and binds a specific molecule, but does not substantially recognize or bind other molecules in a sample. For instance, an antibody or a peptide inhibitor which recognizes and binds a cognate ligand (i.e., an anti-platelet autoantibody that binds with its cognate platelet antigen, and a peptide inhibitor that specifically binds with an autoantibody thereby inhibiting such binding) in a sample, but does not substantially recognize or bind other molecules in the sample.

To "treat" a disease as the term is used herein, means to reduce the frequency of the disease or disorder reducing the frequency with which a symptom of the one or more symptoms disease or disorder is experienced by an animal.

DESCRIPTION

The invention relates to compositions and methods for identifying anti-platelet antibodies, as well as compositions and methods of identifying inhibitors of such antibodies. In addition, the invention relates to compositions and methods for inhibiting blood clotting and various platelet functions, and to methods of treating various platelet-related autoimmune diseases.

Until the present invention, technical obstacles had prevented identification and isolation of human monoclonal anti-platelet autoantibodies. The data disclosed herein demonstrates novel screening methods for the successful identification of numerous novel human anti-platelet autoantibodies which are disclosed herein. Further, the invention relates to identification of novel inhibitors of such antibodies. In addition, the invention relates to methods of inhibiting platelet function, including, among other things, inhibition of platelet aggregation, activation, serotonin release, fibronigen binding, and the like, using the novel anti-platelet autoantibodies of the invention. Additionally, the invention relates to reversing the inhibition using the novel inhibitors of the invention. Moreover, the invention relates to uses for the novel autoantibodies, including diagnostics and development of therapeutics for diseases mediated by autoantibody binding with platelet antigens.

I. Isolated Nucleic Acids

A. Nucleic Acid Encoding an Anti-Platelet Autoantibody

The present invention includes an isolated nucleic acid encoding a mammalian anti-platelet autoantibody, or a biologically active fragment thereof, wherein the nucleotide sequence of the nucleic acid comprises at least one of SEQ ID NO: 1 (H4), SEQ ID NO:2 (H10), SEQ ID NO:3 (H29), SEQ ID NO:4 (H36), SEQ ID NO:5 (H37), SEQ ID NO:6 (H38), SEQ ID NO:7 (H39), SEQ ID NO:8 (H40), SEQ ID NO:9 (H41); SEQ ID NO:110 (H42), SEQ ID NO:11 (H44), SEQ ID NO:12 (H45), SEQ ID NO:13 (H46), SEQ ID NO:14 (H47), SEQ ID NO:15 (H48), and SEQ ID NO:16 (H83).

In another aspect, the nucleic acid encodes a light chain, where the nucleotide sequence of the nucleic acid encoding the light chain comprises at least one sequence selected from the group consisting of SEQ ID NO:17 (L4), SEQ ID NO:18 (L16), SEQ ID NO:19 (L24); SEQ ID NO:20 (L34), SEQ ID NO:21 (L35), SEQ ID NO:22 (L36), SEQ ID NO:23 (L37), SEQ ID NO:24 (L38), SEQ ID NO:25 (L39), SEQ ID NO:26 (L40), SEQ ID NO:27 (L41), SEQ ID NO:28 (L42), SEQ ID NO:29 (L43); SEQ ID NO:30 (L44), SEQ ID NO:31 (L45), SEQ ID NO:32 (L46), SEQ ID NO:33 (L47), SEQ ID NO:34 (L48), SEQ ID NO:35 (L49), SEQ ID NO:36 (L50), SEQ ID NO:37 (L51), SEQ ID NO:38 (L52), SEQ ID NO:39 (L53); SEQ ID NO:40 (L54), SEQ ID NO:41 (L55), SEQ ID NO:42 (L61), SEQ ID NO:43 (L63), SEQ ID NO:44 (L64), SEQ ID NO:45 (L72), SEQ ID NO:46 (L74), SEQ ID NO:47 (L75), SEQ ID NO:48 (L76), SEQ ID NO:49 (L125); SEQ ID NO:50 (L92), SEQ ID NO:51 (L104), SEQ ID NO:52 (L106), and SEQ ID NO:53 (L122).

In another aspect, the present invention includes an isolated nucleic acid encoding a mammalian anti-platelet autoantibody, or a biologically active fragment thereof, wherein the protein encoded by the nucleic acid is a heavy chain and where the amino acid of the heavy chain is a sequence of at least one of SEQ ID NO:54 (H4), SEQ ID NO:55 (H10), SEQ ID NO:56 (H29), SEQ ID NO:57 (H36), SEQ ID NO:58 (H37), SEQ ID NO:59 (H38), SEQ ID NO:60 (H39), SEQ ID NO:61 (H40), SEQ ID NO:62 (H41); SEQ ID NO:63 (H42), SEQ ID NO:64 (H44), SEQ ID NO:65 (H45), SEQ ID NO:66 (1146), SEQ ID NO:67 (H47), SEQ ID NO:68 (H48), and SEQ ID NO:69 (H83).

Similarly, the invention encompasses an isolated nucleic acid encoding an anti-platelet autoantibody, where the nucleic acid encodes a light chain, and where the amino acid of the light chain comprises a sequence selected from the group consisting of SEQ ID NO:70 (L4), SEQ ID NO:71 (L16), SEQ ID NO:72 (L24); SEQ ID NO:73 (L34), SEQ ID NO:74 (L35), SEQ ID NO:75 (L36), SEQ ID NO:76 (L37), SEQ ID NO:77 (L38), SEQ ID NO:78 (L39), SEQ ID NO:79 (L40), SEQ ID NO:80 (L41), SEQ ID NO:81 (142), SEQ ID NO:82 (L43); SEQ ID NO:83 (L44), SEQ ID NO:84 (L45), SEQ ID NO:85 (L46), SEQ ID NO:86 (L47), SEQ ID NO:87 (L48), SEQ ID NO:88 (L49), SEQ ID NO:89 (L50), SEQ ID NO:90 (L51), SEQ ID NO:91 (L52), SEQ ID NO:92 (L53); SEQ ID NO:93 (L54), SEQ ID NO:94 (L55), SEQ ID NO:95 (L61), SEQ ID NO:96 (L63), SEQ ID NO:97 (L64), SEQ ID NO:98 (L72), SEQ ID NO:99 (L74), SEQ ID NO:100 (L75), SEQ ID NO:101 (L76), SEQ ID NO: 102 (L125); SEQ ID NO:103 (L92), SEQ ID NO:104 (L104), SEQ ID NO:105 (L106), and SEQ ID NO:106 (L122).

One skilled in the art, armed with the teachings provided herein, would appreciate that the heavy and light chains of the autoantibodies of the invention can be combined in any combination to arrive at an anti-platelet autoantibody as disclosed elsewhere herein. That is, the data disclosed elsewhere herein demonstrate that a heavy chain, or a light chain, can combine with various other light or heavy chains, respectively, to produce an anti-platelet autoantibody as disclosed herein. For instance, the data disclosed in FIG. 1 clearly demonstrate that the heavy chain, H38, can combine with several light chains, e.g., L39, L49, L54, L55, L72, L74, L75, and L76. Similarly, the data demonstrate that a light chain, e.g., L44, can combine with several heavy chains, e.g., H37 and H39. Thus, the data demonstrate that the heavy and light chains disclosed here, as well as those identified using the methods disclosed herein, can be combined such that the combinations produce autoantibodies of the invention. Methods for screening potential autoantibodies, including combinations of various heavy and light chains, are set forth elsewhere herein. Therefore, the skilled artisan, armed with teachings known in the art and the disclosure provided herein, would be able to isolated and identify anti-platelet autoantibodies, especially where heavy and light chains of such autoantibodies have been described previously.

The skilled artisan, based upon the disclosure provided herein, would understand that the nucleic acids of the invention are useful for production of the autoantibody of interest. Further, the nucleic acids are useful for studying, among other things, the genetic origins of the autoantibodies, as well as, but not limited to, the extent of somatic mutation and clonal relatedness.

One skilled in the art would appreciate, based upon the disclosure provided herein, that a homolog of anti-platelet autoantibody likely exists and can be readily identified and isolated using the novel screening methods described herein and using the sequence data disclosed herein. Thus, the present invention encompasses additional anti-platelet autoantibodies that can be readily identified based upon the disclosure provided herein.

The isolated nucleic acid of the invention should be construed to include an RNA or a DNA sequence encoding an anti-platelet autoantibody of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding anti-platelet autoantibodies can be identified, such as, but not limited to, other nucleic acids encoding human autoantibodies, as well as those present in other species of mammals (e.g., ape, gibbon, bovine, ovine, equine, porcine, canine, feline, and the like). These additional sequences can be obtained by following the procedures described herein in the experimental details section for the isolation of human nucleic acids encoding anti-platelet autoantibodies as disclosed herein (e.g., screening of phage display libraries, panning on intact platelets, and the like), and procedures that are well-known in the art, or to be developed.

Further, any number of procedures may be used for the generation of mutant, derivative or variant forms of an anti-platelet autoantibody using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention includes a nucleic acid encoding a mammalian anti-platelet autoantibody wherein a nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one anti-platelet autoantibody, or biologically active fragment thereof. Such tag polypeptides are well known in the art and include, for instance, green fluorescent protein (GFP), an influenza virus hemagglutinin tag polypeptide, myc, myc-pyruvate kinase (myc-PK), His$_6$, maltose binding protein (MBP), a FLAG tag polypeptide, and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should, be construed to be included in the present invention.

The nucleic acid comprising a nucleic acid encoding a tag polypeptide can be used to localize an anti-platelet autoantibody, or a biologically active fragment thereof, within a cell, a tissue (e.g., a blood vessel, bone, and the like), and/or a whole organism (e.g., a human, and the like), and to study the role(s) of an anti-platelet autoantibody in a cell. Further, addition of a tag polypeptide facilitates isolation and purification of the "tagged" protein such that the proteins of the invention can be produced and purified readily.

Further, anti-platelet auto antibody chimeric immunoglobulins of this invention are also useful for thrombus imaging. For this purpose, antibody fragments are generally preferred. Chimeric heavy chain gene can be designed in truncated form to produce a chimeric immunoglobulin fragment (e.g., Fab, Fab', or F(ab')$_2$) for immunoscintigraphic imaging. These molecules can be labeled either directly or through a coupled chelating agent such as DTPA, with radioisotopes such as $^{131}$Iodine, $^{125}$Iodine, $^{99m}$Technetium or $^{111}$Indium to produce radioimmunoscintigraphic agents. Alternatively, a radiometal binding (chelating) domain can be engineered into the chimeric antibody site to provide a site for labeling. Thus, a chimeric immunoglobulin can be designed as a protein that has a platelet-specific variable region, a constant region (preferably truncated), and a metal binding domain derived from a metal binding protein, such as metallothionein.

The platelet-specific chimeric immunoglobulin is administered to a patient suspected of having thrombus. After sufficient time to allow the labeled immunoglobulin to localize at the thrombus site, the signal generated by the label is detected by a photoscanning device such as a gamma camera. The detected signal is then converted to an image of the thrombus. The image makes it possible to locate the thrombus in vivo and to devise an appropriate therapeutic strategy.

Where an anti-platelet autoantibody of the invention binds with platelets that are activated, inactivated, or both, it would be understood that a thrombus can be visualized due to the aggregation of the platelets producing a detectable signal over background "noise" due to labeling of all platelets. Alternatively, where an anti-platelet autoantibody of the invention binds specifically activated, but not inactivated, platelets, the thrombus can be detected since activated platelets will be present therein.

B. Nucleic Acid Encoding a Peptide Inhibitor

The present invention includes an isolated nucleic acid encoding a peptide inhibitor of an anti-platelet autoantibody, or a biologically active fragment thereof, wherein the nucleic acid comprises a nucleotide sequence selected from the group consisting of P4-12 (SEQ ID NO:107); P34 (SEQ ID NO:108); P4-7 (SEQ ID NO:109); P4-2a (SEQ ID NO:110); P73-11 (SEQ ID NO:115); P123-10 (SEQ ID NO: 117); P74-4 (SEQ ID NO:119); P73-10 (SEQ ID NO:121); P74-3 (SEQ ID NO:123); P74-9 (SEQ ID NO: 125); P74-5 (SEQ ID NO:127); P73-9 (SEQ ID NO:129); P124-8 (SEQ ID NO:131); P123-11 (SEQ ID NO:133); P124-1 (SEQ ID NO:135); P73-2 (SEQ ID NO: 137); P73-6 (SEQ ID NO:139); P124-11 (SEQ ID NO: 141); P124-2 (SEQ ID NO:143); P73-7 (SEQ ID NO:145); P74-1a (SEQ ID NO:147); P123-8 (SEQ ID NO:149); P74-8 (SEQ ID NO:151).

In another aspect, the present invention includes an isolated nucleic acid encoding a peptide inhibitor of an anti-platelet autoantibody, or a biologically active fragment thereof, wherein the protein encoded comprises an amino acid sequence seletected from the group consisting of P4-12 (SEQ ID NO:111); P3-4 (SEQ ID NO:112); P4-7 (SEQ ID NO:113); P4-2a (SEQ ID NO:114); P73-11 (SEQ ID NO:116); P123-10 (SEQ ID NO: 118); P74-4 (SEQ ID NO:120); P73-10 (SEQ ID NO: 122); P74-3 (SEQ ID NO:124); P74-9 (SEQ ID NO:126); P74-5 (SEQ ID NO:128); P73-9 (SEQ ID NO:130); P124-8 (SEQ ID NO:132); P123-11 (SEQ ID NO:134); P124-1 (SEQ ID NO:136); P73-2 (SEQ ID NO:138); P73-6 (SEQ ID NO:140); P124-11 (SEQ ID NO:142); P124-2 (SEQ ID NO:144); P73-7 (SEQ ID NO:146); P74-1a (SEQ ID NO:148); P123-8 (SEQ ID NO:150); P74-8 (SEQ ID NO:152).

The skilled artisan, armed with the teachings provided herein, would appreciate that such peptide inhibitor of the binding of an anti-platelet autoantibody is useful for, among other things, inhibiting such binding, thereby treating or ameliorating any disease mediated or associated with such binding, including, but not limited to, ITP post-transfusion purpura (PTP), and the like. This is because, as demonstrated elsewhere herein, the peptide inhibitor binds with the autoantibody thereby preventing the autoantibody from binding its cognate antigen, e.g., a platelet component, such as, but not limited to, a glycoprotein present on the platelet surface. Thus, the peptide inhibitor inhibits the binding, which binding mediates the disease, thereby treating or ameliorating the disease, disorder or condition mediated by autoantibody binding with a platelet, or a component of a platelet.

II. Isolated Polypeptides

The invention also includes an isolated polypeptide comprising a mammalian anti-platelet autoantibody, or a biologically active fragment thereof. Preferably, the isolated polypeptide comprises a heavy chain, where the amino acid of the heavy chain is selected from the group consisting of heavy chain and where the amino acid of the heavy chain is a sequence of at least one of SEQ ID NO:54 (H4), SEQ ID NO:55 (H110), SEQ ID NO:56 (H29), SEQ ID NO:57 (H36), SEQ ID NO:58 (H37), SEQ ID NO:59 (H38), SEQ ID NO:60 (H39), SEQ ID NO:61 (H40), SEQ ID NO:62 (H41); SEQ ID NO:63 (H42), SEQ ID NO:64 (H44), SEQ ID NO:65 (H145), SEQ ID NO:66 (H46), SEQ ID NO:67 (H47), SEQ ID NO:68 (H48), and SEQ ID NO:69 (H83).

The invention also includes an isolated polypeptide comprising a mammalian anti-platelet autoantibody, or a biologically active fragment thereof, where the autoantibody comprises a light chain where the amino acid of the light chain comprises an amino acid sequence selected from the group consisting of SEQ ID NO:70 (LA), SEQ ID NO:71 (L16), SEQ ID NO:72 (L24); SEQ ID NO:73 (L34), SEQ ID NO:74 (L35), SEQ ID NO:75 (L36), SEQ ID NO:76 (L37), SEQ ID NO:77 (L38), SEQ ID NO:78 (L39), SEQ ID NO:79 (L40), SEQ ID NO:80 (L41), SEQ ID NO:81 (L42), SEQ ID NO:82 (L43); SEQ ID NO:83 (L44), SEQ ID NO:84 (L45), SEQ ID NO:85 (L46), SEQ ID NO:86 (L47), SEQ ID NO:87 (L48), SEQ ID NO:88 (L49), SEQ ID NO:89 (L50), SEQ ID NO:90 (L51), SEQ ID NO:91 (L52), SEQ ID NO:92 (L53); SEQ ID NO:93 (L54), SEQ ID NO:94 (L55), SEQ ID NO:95 (L61), SEQ ID NO:96 (L63), SEQ ID NO:97 (L64), SEQ ID NO:98 (L72), SEQ ID NO:99 (L74), SEQ ID NO:100 (L75), SEQ ID NO:101 (L76), SEQ ID NO:102 (L125); SEQ ID NO:103 (L92), SEQ ID NO:104 (L104), SEQ ID NO:105 (L106), and SEQ ID NO:106 (L122).

The skilled artisan would appreciate, based upon the disclosure provided herein, that the heavy chain can combine with a wide plethora of light chains, and the other way around, such that each of the heavy and light chains can combine with a light or heavy chain, respectively, disclosed herein. Moreover, each heavy and light chain disclosed herein can combine with a light or heavy chain, respectively, not disclosed, but known in the art, or to be identified in the future. This is because, as more fully set forth elsewhere herein (see, e.g., FIG. 1 and discussion thereof), a single light chain can combine with various heavy chains to produce an anti-platelet autoantibody of the invention. Similarly, the data disclosed elsewhere herein amply demonstrate that a single heavy chain can combine with various light chains to form an anti-platelet autoantibody of the invention. Thus, one skilled in the art, armed with the teachings provided herein, and methods well-known in the art, could readily identify additional H+ L chain combinations that bind with a platelet component, and such autoantibodies are encompassed herein.

Additionally, certain combinations of heavy and light chains are preferred, and are as follows: H44L4 [SEQ ID NO:64 (H44) and SEQ ID NO:70 (L4)], H46L16 [SEQ ID NO:66 (H46) and SEQ ID NO:71 (L16)], H48L24 [SEQ ID NO:68 (H48) and SEQ ID NO:72 (L24)], H36L35 [SEQ ID NO:57 (H36) and SEQ ID NO:74 (L35)], H40L36 [SEQ ID NO:61 (H40) and SEQ ID NO:75 (L36)], H83L34 [SEQ ID NO:69 (H83) and SEQ ID NO:73 (L34)], H39L37 [SEQ ID NO:60 (H39) and SEQ ID NO:76 (L37)], H42L38 [SEQ ID NO:63 (H42) and SEQ ID NO:77 (L38)], H38L39 [SEQ ID NO:59 (H38) and SEQ ID NO:78 (L39)], H37L40 [SEQ ID NO:58 (H37) and SEQ ID NO:79 (L40)], H37L41 [SEQ ID NO:58 (H37) and SEQ ID NO:80 (L41)], H40L42 [SEQ ID NO:61 (H40) and SEQ ID NO:81 (L42)], H39L43 [SEQ ID NO:60 (H39) and SEQ ID NO:82 (L43)], H37L44 [SEQ ID NO:58 (H37) and SEQ ID NO:83 (L44)], H39L44 [SEQ ID NO:60 (H39) and SEQ ID NO:83 (L44)], H37L45 [SEQ ID NO:58 (H37) and SEQ ID NO:84 (L45)], H39L46 [SEQ ID NO:60 (H39) and SEQ ID NO:85 (L46)], H37L47 [SEQ ID NO:58 (H37) and SEQ ID NO:86 (L47)], H37L48 [SEQ ID NO:58 (H37) and SEQ ID NO:87 (L48)], H38L49 [SEQ ID NO:59 (H38) and SEQ ID NO:88 (L49)], H37L50 [SEQ ID NO:58 (H37) and SEQ ID NO:89 (L50)], H41L51 [SEQ ID NO:62 (H41) and SEQ ID NO:90 (L51)], H40L52 [SEQ ED NO:61 (H40) and SEQ ID NO:91 (L52)], H40L53 [SEQ ID NO:61 (H40) and SEQ ID NO:92 (L53)], H38L54 [SEQ ID NO:59 (H38) and SEQ ID NO:93 (L54)], H38L55 [SEQ ID NO:59 (H38) and SEQ ID NO:94 (L55)], H45L61 [SEQ ID NO:84 (L45) and SEQ ID NO:95 (L61)], H47L63 [SEQ ID NO:67 (H47) and SEQ ID NO:96 (L63)], H47L64 [SEQ ID NO:67 (H47) and SEQ ID NO:97 (L64)], H38L72 [SEQ ID NO:59 (H38) and SEQ ID NO:98 (L72)], H38L74 [SEQ ID NO:59 (H38) and SEQ ID NO:99 (L74)], H38L75 [SEQ ID NO:59 (H38) and SEQ ID NO:100 (L75)], H38L76 [SEQ ID NO:59 (H138) and SEQ ID NO:101 (L76)], H36L76 [SEQ ID NO:57 (H36) and SEQ ID NO:101 (L76)], H37L92 [SEQ ID NO:58 (H37) and SEQ ID NO:103 (L92)], H29L104 [SEQ ID NO:56 (H29) and SEQ ID NO:104 (L104)], H4L106 [SEQ ID NO:54 (H4) and SEQ ID NO:105 (L106)], and H10L122 [SEQ ID NO:55 (H10) and SEQ ID NO:106 (L122)]. However, as pointed out previously elsewhere herein, the autoantibodies of the present invention are in no way limited to these, or any other, combination of heavy and light chains.

The invention encompasses a biologically active fragment of the anti-platelet autoantibody of the invention. That is, the skilled artisan would appreciate, based upon the disclosure provided herein, that a fragment of the autoantibody of the invention can be used in the methods of the invention. Use of antibody fragments is well known in the art, and the identification of the relevant portion(s) of the antibody molecule to be used is within the purview of the skilled artisan. Accordingly, identification and production of antibody fragments that have biological acitivity that is substantially similar, if not identical, to the full-length autoantibody molecule, is encompassed in the present invention.

The present invention also encompasses an anti-platelet antibody, or biologically active fragment thereof, that specifically binds with a specific region of a platelet antigen. Such platelet antigen includes, but is not limited to, certain integrins, e.g., GPIa/IIa, GPIIb/IIIa, and GPIb/IX, among others. However, the invention is not limited to these, or any other, platelet component. That is, using the methods disclosed elsewhere herein, and following the teachings set forth elsewhere herein, the skilled artisan could readily identify anti-platelet autoantibodies that specifically bind with a wide plethora of platelet components.

Further, the present invention includes an anti-platelet autoantibody that specifically binds a certain portion of a platelet component. More specifically, the portions of the platelet component required for epitope expression and recognition by the autoantibody can be identified, and autoantibodies that require one, but not other, portions of the full-length platelet component can be identified. Such autoantibody includes, but is not limited to, an anti-platelet autoantibody that requires a certain portion of, e.g., GPIIb/IIIa, such as, but not limited to, from about amino acid residue number 447 to about amino acid residue number 1009 of $\alpha_{IIb}$ (SEQ ID NO: 153; GenBank Acc. No. P08514), for binding with the platelet component (GPIIb/IIIa) Thus, the invention includes an anti-platelet autoantibody that does not require the N-terminal portion of the $\alpha_{IIb}$ type of integrin (i.e., the analogous vitronectin portion will suffice), e.g., the portion comprising from about amino acid residue number 1 to about amino acid residue number 446 relative to the sequence of SEQ ID NO:153.

The invention encompasses monoclonal, synthetic antibodies, and the like. One skilled in the art would understand, based upon the disclosure provided herein, that the crucial feature of the autoantibody of the invention is that the autoantibody bind specifically with a platelet component (e.g., GPIa/IIa, GPIIb/IIIa, GPIb/IX, and the like). That is, the autoantibody of the invention recognizes a platelet, or a component thereof, as demonstrated by the data disclosed elsewhere herein, using standard methods well-known in the art, and such binding can also be assessed using methods known in the art but not described herein, as well as methods to be developed in the future.

The present invention encompasses monoclonal antibodies identified using the screening methods disclosed elsewhere herein.

The autoantibodies of the invention, which are produced by a phage display library, can be subcloned and expressed from an appropriate promoter sequence in cells suitable for the generation of large quantities of peptide. Monoclonal autoantibodies of the invention can also be produce by chemical synthesis using standard procedures known in the art.

Nucleic acid encoding the monoclonal autoantibody obtained using the procedures described herein may be cloned and sequenced using technology which is available in the art, and is described, for example, in Wright et al. (1992, Critical Rev. Immunol. 12:125-168), and the references cited therein.

Further, a non-human mammalian autoantibody of the invention may be "humanized" using the technology described in, for example, Wright et al. (supra), and in the references cited therein, and in Gu et al. (1997, Thrombosis and Hematocyst. 77:755-759), and other methods of humanizing antibodies well-known in the art or to be developed.

As more fully set forth elsewhere herein, to generate a phage antibody library, a cDNA library is first obtained from mRNA which is isolated from cells, e.g., splenocytes from a normal animal or an animal, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described herein in, as well as in for example, in Sambrook et al., supra.

Bacteriophage which encode the desired antibody may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Methods relating to production of such display libraries, and the screening thereof, are set forth in U.S. Pat. No. 6,255,455, to Siegel, which is incorporated by reference as if set forth in its entirety herein. Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors (or phagemids with M13 packaging signals) creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581-597). Panning of phage so generated for the isolation of a desired antibody is conducted in a manner similar to that described for phage libraries comprising Fab DNA.

The present autoantibodies can be monovalent, divalent or polyvalent. Monovalent immunoglobulins are dimers (HL) formed of a chimeric heavy chain associated through disulfide bridges with a chimeric light chain. Divalent immunoglobulins are tetramers ($H_2 L_2$) formed of two dimers associated through at least one disulfide bridge. Polyvalent immunoglobulins can also be produced, for example, by employing a heavy chain constant region that aggregates (e.g., µ heavy chain constant regions). Chimeric immunoglobulin fragments such as Fab, Fab' or F(ab')$_2$ can also be produced. For purposes of using the present autoantibodies to affect platelet function, but not result in platelet destruction (such as in patients with ITP from whom the antibody clones were derived), immunoglobulin fragments bearing just the antigen recognition portion (e.g. Fab, Fab', F(ab')$_2$, or Fv) and lacking an Fc domain may be desirable. That is, the skilled artisan, based upon the disclosure provided herein, would understand that the invention encompasses producing and using a fragment of a full-length autoantibody which lacked the CH2 and CH3 constant region domains of the full-length form (i.e., the Fc portion) so as to maintain platelet binding of the fragment with the platelet, or component of the platelet, but eliminate Fc receptor binding to macrophages (and other cells bearing Fc receptors) and resultant platelet destruction.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

The present invention also provides for analogs of proteins or peptides which comprise an anti-platelet autoantibody, or biologically active fragment thereof, as disclosed herein. The invention further includes analogs of peptide inhibitors of autoantibody binding, which inhibitors are disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are anti-platelet autoantibody, or biologically active fragment thereof, peptide inhibitors thereof, or both, which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the anti-platelet autoantibody, or biologically active fragment thereof, or the peptide inhibitor thereof, of the present invention.

Further, the invention should be construed to include naturally occurring variants or recombinantly derived mutants of anti-platelet autoantibody, or biologically active fragment thereof, sequences, which variants or mutants render the protein encoded thereby either more, less, or just as biologically active as the full-length clones of the invention.

The nucleic acids, and peptides encoded thereby, are useful tools for elucidating and affecting the function(s) of platelets. Further, nucleic and amino acids comprising mammalian anti-platelet autoantibody, or biologically active fragment thereof, are useful diagnostics which can be used, for example, to identify a compound that, inter alia, inhibits binding of an anti-platelet autoantibody, or biologically active fragment thereof, with a platelet, and is therefore a potential therapeutic drug candidate for, among other things, a disease, disorder or condition mediated by binding of an anti-platelet autoantibody with a platelet, e.g., ITP, and the like.

Additionally, the nucleic and amino acids of the invention can be used to produce recombinant cells and transgenic non-human mammals which are useful tools for the study of autoantibody action, the identification of novel diagnostics and therapeutics for treatment, and for elucidating the cellular role(s) of an anti-platelet autoantibody, or biologically active fragment thereof, among other things. For instance, transgenic animals can be used to a disease, disorder or condition mediated by binding of an anti-platelet autoantibody with a platelet, such as, but not limited to, ITP.

Further, the nucleic and amino acids of the invention can be used diagnostically, either by assessing the level of gene expression or protein expression, to assess severity and prognosis of a disease, disorder or condition mediated by binding of an anti-platelet autoantibody, or biologically active fragment thereof, with a platelet, e.g. ITP. The nucleic acids and proteins of the invention are also useful in the development of assays to assess the efficacy of a treatment for treating, ameliorating, or both, such disease, and the like. That is, the nucleic acids and polypeptides of the invention can be used to detect the effect of various therapies on a disease, disorder or condition mediated by binding of an anti-platelet autoantibody with a platelet, thereby ascertaining the effectiveness of the therapies such as, but not limited to, assessment of treatment efficacies for ITP, and the like. For example, peptides specific for particular clones of patient anti-platelet autoantibodies can be used to assess the level of such autoantibodies in patient serum during various treatment protocols. This is because the level of the autoantibody present in plasma is correlated to the severity, prognosis, and the like, for the disease, and assessing the level of the autoantibody provides as method of assessing the efficacy of the treatment.

III. Vectors

In other related aspects, the invention includes an isolated nucleic acid encoding an anti-platelet autoantibody, or biologically active fragment thereof, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, supra), and Ausubel et al. (1997, supra). However, the present invention does not encompass a vector comprising the pComb3H phagemid vector.

Expression of an anti-platelet autoantibody, or biologically active fragment thereof, either alone or fused to a detectable tag polypeptide, in cells which either do not normally express the anti-platelet autoantibody, or biologically active fragment thereof, or which do not express the anti-platelet autoantibody, or biologically active fragment thereof, fused with a tag polypeptide, may be accomplished by generating a plasmid, viral or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like.

Moreover, inducible and tissue specific expression of the nucleic acid encoding an anti-platelet autoantibody, or biologically active fragment thereof, may be accomplished by placing the nucleic acid encoding an anti-platelet autoantibody, or biologically active fragment thereof, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Similarly, the invention encompasses an isolated nucleic acid encoding a peptide inhibitor of binding of an anti-platelet autoantibody, or biologically active fragment thereof, wherein the nucleic acid encoding the inhibitor is operably linked to a nucleic acid comprising a promoter/regulatory sequence such that the nucleic acid is preferably capable of directing expression of the peptide inhibitor encoded by the nucleic acid.

Expressing an anti-platelet autoantibody, or biologically active fragment thereof, or a peptide inhibitor of such an autoantibody, using a vector, allows the isolation of large amounts of recombinantly produced protein.

Selection of any particular plasmid vector or other DNA vector is not a limiting factor in this invention and a wide plethora vectors is well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook, supra, and Ausubel, supra.

The invention thus includes a vector comprising an isolated nucleic acid encoding an anti-platelet autoantibody, or biologically active fragment thereof, or a peptide inhibitor of such autoantibody. The incorporation of a desired nucleic acid into a vector and the choice of vectors is well-known in the art as described in, for example, Sambrook et al., supra, and Ausubel et al., supra.

The invention also includes cells, viruses, proviruses, and the like, containing such vectors. Methods for producing cells comprising vectors and/or exogenous nucleic acids are well-known in the art. See, e.g., Sambrook et al., supra; Ausubel et al., supra.

The nucleic acids encoding an anti-platelet autoantibody, or biologically active fragment thereof, or a peptide inhibitor of such an anti-platelet autoantibody, can be cloned into various plasmid vectors. However, the present invention should not be construed to be limited to plasmids or to any particular vector. Instead, the present invention should be construed to encompass a wide plethora of vectors which are readily available and/or well-known in the art and no vector at all.

IV. Antisense Molecules and Ribozymes

Further, the invention includes a recombinant cell comprising an antisense nucleic acid which cell is a useful model for elucidating the role(s) of an anti-platelet autoantibody in cellular processes. Accordingly, a transgenic cell comprising an antisense nucleic acid complementary to a nucleic acid encoding an anti-platelet autoantibody, but in an antisense orientation, is a useful tool for the study of the mechanism(s) of action of the autoantibody and its role(s) in the cell and for the identification of therapeutics that ameliorate the effect(s) of autoantibody binding with a platelet.

One skilled in the art will appreciate that one way to decrease the levels of an anti-platelet autoantibody mRNA and/or protein in a cell is to inhibit expression of the nucleic acid encoding the protein. Expression of an anti-platelet autoantibody may be inhibited using, for example, antisense molecules, and also by using ribozymes or double-stranded RNA as described in, for example, Wianny and Kernicka-Goetz (2000, Nature Cell Biol. 2:70-75).

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue (1993, U.S. Pat. No. 5,190,931).

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of an anti-platelet autoantibody can be designed by incorporating target sequences into the basic ribozyme structure which are complementary to the mRNA sequence of the anti-platelet autoantibody or complementary to a nucleic acid sequence comprising a nucleotide sequence selected from the group consisting of SEQ ID NO:1 (H4), SEQ ID NO:2 (H10), SEQ ID NO:3 (H29), SEQ ID NO:4 (H36), SEQ ID NO:5 (H37), SEQ ID NO:6 (H38), SEQ ID NO:7 (H39), SEQ ID NO:8 (H40), SEQ ID NO:9 (H41); SEQ ID NO:10 (H42), SEQ ID NO: 11 (H44), SEQ ID NO: 12 (H45), SEQ ID NO: 13 (H46), SEQ ID NO: 14 (H47), SEQ ID NO:15 (H48), SEQ ID NO:16 (H83), SEQ ID NO:17 (L4), SEQ ID NO:18 (L16), SEQ ID NO:19 (L24); SEQ ID NO:20 (L34), SEQ ID NO:21 (L35), SEQ ID NO:22 (L36), SEQ ID NO:23 (L37), SEQ ID NO:24 (L38), SEQ ID NO:25 (L39), SEQ ID NO:26 (L40), SEQ ID NO:27 (L41), SEQ ID NO:28 (L42), SEQ ID NO:29 (L43); SEQ ID NO:30 (L44), SEQ ID NO:31 (L45), SEQ ID NO:32 (L46), SEQ ID NO:33 (L47), SEQ ID NO:34 (L48), SEQ ID NO:35 (L49), SEQ ID NO:36 (L50), SEQ ID NO:37 (L51), SEQ ID NO:38 (L52), SEQ ID NO:39 (L53); SEQ ID NO:40 (L54), SEQ ID NO:41 (L55), SEQ ID NO:42 (L61), SEQ ID NO:43 (L63), SEQ ID NO:44 (L64), SEQ ID NO:45 (L72), SEQ ID NO:46 (L74), SEQ ID NO:47 (L75), SEQ ID NO:48 (L76), SEQ ID NO:49 (L125); SEQ ID NO:50 (L92), SEQ ID NO:51 (L104), SEQ ID NO:52 (L106), and SEQ ID NO:53 (L122). Moreover, an antisense for a nucleic acid sequence encoding a anti-platelet autoantibody identified using the methods of the invention is also encompassed by the invention.

Ribozymes targeting an anti-platelet autoantibody may be synthesized using commercially available reagents (Applied Biosystems, Inc., Foster City, Calif.) or they may be genetically expressed from DNA encoding them.

V. Recombinant Cells and Transgenic Non-Human Mammals

The invention includes a recombinant cell comprising, inter alia, an isolated nucleic acid encoding an anti-platelet autoantibody, or a biologically active fragment thereof, an antisense nucleic acid complementary thereto, a nucleic acid encoding a peptide inhibitor of an anti-platelet autoantibody, and the like. In one aspect, the recombinant cell can be transiently transfected with a vector (e.g., a plasmid, and the like) encoding a portion of the nucleic acid encoding the anti-platelet autoantibody, or a biologically active fragment thereof, an antisense nucleic acid complementary thereto, a nucleic acid encoding a peptide inhibitor of an anti-platelet autoantibody. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, fibroblasts, mouse stem cells, amphibian oocytes, osteoblasts, smooth muscle cells, endothelial cells, and the like.

In one aspect, the recombinant cell comprising an isolated nucleic acid encoding mammalian anti-platelet autoantibody, or a biologically active fragment thereof, is used to produce a transgenic non-human mammal. That is, the exogenous nucleic acid, or "transgene" as it is also referred to herein, of the invention is introduced into a cell, and the cell is then used to generate the non-human transgenic mammal. The cell into which the transgene is introduced is preferably an embryonic stem (ES) cell. However, the invention should not be construed to be limited solely to ES cells comprising the transgene of the invention nor to cells used to produce transgenic animals. Rather, a transgenic cell of the invention includes, but is not limited to, any cell derived from a transgenic animal comprising a transgene, a cell comprising the transgene derived from a chimeric animal derived from the transgenic ES cell, and any other comprising the transgene which may or may not be used to generate a non-human transgenic mammal.

Further, it is important to note that the purpose of transgene-comprising, i.e., recombinant, cells should not be construed to be limited to the generation of transgenic mammals. Rather, the invention should be construed to include any cell type into which a nucleic acid encoding a mammalian anti-platelet autoantibody, or a biologically active fragment thereof, is introduced, including, without limitation, a prokaryotic cell and a eukaryotic cell comprising an isolated nucleic acid encoding mammalian anti-platelet autoantibody, or a biologically active fragment thereof.

When the cell is a eukaryotic cell, the cell may be any eukaryotic cell which, when the transgene of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, a disease mediated by binding of the anti-platelet autoantibody, or a biologically active fragment thereof, with a platelet (e.g., ITP), and the like. That is, one skilled in the art would appreciate, based upon the disclosure provided herein, that because binding of an anti-platelet antibody with its ligand mediates, among other things, clearance of platelets, inhibited platelet function, including decreased aggregation, activation, and the like, selected disease states or processes associated with such inhibition can be investigated by assessing expression, or lack of expression, of the anti-platelet autoantibody, such as, but not limited to, ITP and post-transfusion purpura (PTP).

Alternatively, the invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system in the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Such cell expressing an isolated nucleic acid encoding an anti-platelet autoantibody, or a biologically active fragment thereof, can be used to provide the anti-platelet autoantibody, or a biologically active fragment thereof, to a cell, tissue, or whole animal where a higher level of an anti-platelet autoantibody, or a biologically, active fragment thereof, can be useful to treat or alleviate a disease, disorder or condition associated with low level of anti-platelet autoantibody, or a biologically active fragment thereof, expression and/or activity.

One of ordinary skill would appreciate, based upon the disclosure provided herein, that a "knock-in" or "knock-out" vector of the invention comprises at least two sequences homologous to two portions of the nucleic acid which is to be replaced or deleted, respectively. The two sequences are homologous with sequences that flank the gene; that is, one sequence is homologous with a region at or near the 5' portion of the coding sequence of the nucleic acid encoding an anti-platelet autoantibody, or a biologically active fragment thereof, and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all (i.e., a "knock-out" vector) or which insert (i.e., a "knock-in" vector) a nucleic acid encoding an anti-platelet autoantibody, or a biologically active fragment thereof, from or into a mammalian genome, respectively. The crucial feature of the targeting vector is that it comprise sufficient portions of two sequences located towards opposite, i.e., 5' and 3', ends of the anti-platelet autoantibody, or a biologically active fragment thereof, open reading frame (ORF) in the case of a "knock-out" vector, to allow deletion/insertion by homologous recombination to occur such that all or a portion of the nucleic acid encoding an anti-platelet autoantibody, or a biologically active fragment thereof, is deleted from or inserted into a location on a mammalian chromosome.

The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the anti-platelet autoantibody, or a biologically active fragment thereof, coding region to be used in the targeting vector may be easily selected based upon known methods and following the teachings disclosed herein based on the disclosure provided herein including the nucleic and amino acid sequences of numerous human anti-platelet autoantibodies. Armed with these sequences, one of ordinary skill in the art would be able to construct the transgenes and knock-out vectors of the invention.

The invention further includes a knock-out targeting vector comprising a nucleic acid encoding a selectable marker such as, for example, a nucleic acid encoding the $neo^R$ gene thereby allowing the selection of transgenic cell where the nucleic acid encoding an anti-platelet autoantibody, or a biologically active fragment thereof, has been deleted and replaced with the neomycin resistance gene by the cell's ability to grow in the presence of G418. However, the present invention should not be construed to be limited to neomycin resistance as a selectable marker. Rather, other selectable markers well-known in the art may be used in the knock-out targeting vector to allow selection of recombinant cells where the anti-platelet autoantibody, or a biologically active fragment thereof, gene has been deleted and/or inactivated and replaced by the nucleic acid encoding the selectable marker of choice. Methods of selecting and incorporating a selectable marker into a vector are well-known in the art and are describe in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

As noted herein, the invention includes a non-human transgenic mammal comprising an exogenous nucleic acid inserted into a desired site in the genome thereof thereby deleting the coding region of a desired endogenous target gene, i.e., a knock-out transgenic mammal. Further, the invention includes a transgenic non-human mammal wherein an exogenous nucleic acid encoding an anti-platelet autoantibody, or a biologically active fragment thereof, is inserted into a site in the genome, i.e., a "knock-in" transgenic mammal. The knock-in transgene inserted may comprise various nucleic acids encoding, for example, a tag polypeptide, a promoter/regulatory region operably linked to the nucleic acid encoding an anti-platelet autoantibody, or a biologically active fragment thereof, not normally present in the cell or not typically operably linked to an anti-platelet autoantibody, or a biologically active fragment thereof.

The generation of the non-human transgenic mammal of the invention is preferably accomplished using the method which is now described. However, the invention should in no way be construed as being limited solely to the use of this method, in that, other methods can be used to generate the desired knock-out mammal.

In the preferred method of generating a non-human transgenic mammal, ES cells are generated comprising the transgene of the invention and the cells are then used to generate the knock-out animal essentially as described in Nagy and Rossant (1993, In: Gene Targeting, A Practical Approach, pp. 146-179, Joyner ed., IRL Press). ES cells behave as normal embryonic cells if they are returned to the embryonic environment by injection into a host blastocyst or aggregate with blastomere stage embryos. When so returned, the cells have the full potential to develop along all lineages of the embryo. Thus, it is possible, to obtain ES cells, introduce a desired DNA therein, and then return the cell to the embryonic environment for development into mature mammalian cells, wherein the desired DNA may be expressed.

Precise protocols for the generation of transgenic mice are disclosed in Nagy and Rossant (1993, In: Gene Targeting, A Practical Approach, Joyner ed. IRL Press, pp. 146-179). and are therefore not repeated herein. Transfection or transduction of ES cells in order to introduce the desired DNA therein is accomplished using standard protocols, such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York). Preferably, the desired DNA contained within the transgene of the invention is electroporated into ES cells, and the cells are propagated as described in Soriano et al. (1991, Cell 64:693-702).

Introduction of an isolated nucleic acid into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the nucleic acid is introduced into the embryo by way of microinjection.

Once the nucleic acid is introduced into the egg, the egg is incubated for a short period of time and is then transferred into a pseudopregnant mammal of the same species from which the egg was obtained as described, for example, in Hogan et al. (1986, Manipulating the Mouse Embryo: A Laboratory Manual, Cold Spring Harbor, N.Y.). Typically, many eggs are injected per experiment, and approximately two-thirds of the eggs survive the procedure. About twenty viable eggs are then transferred into pseudopregnant animals, and usually four to ten of the viable eggs so transferred will develop into live pups.

Any mammalian anti-platelet autoantibody gene, or a fragment thereof, may be used in the methods described herein to produce a transgenic mammal or a transgenic cell harboring a transgene comprising a deletion of all or part of a nucleic acid encoding a mammalian anti-platelet autoantibody, or a biologically active fragment thereof. Preferably, a nucleic acid encoding an anti-platelet autoantibody, or a biologically active fragment thereof, such as, e.g., SEQ ID NO: (H4), SEQ ID NO:2 (H10), SEQ ID NO:3 (H29), SEQ ID NO:4 (H36), SEQ ID NO:5 (H37), SEQ ID NO:6 (H38), SEQ ID NO:7 (H39), SEQ ID NO:8 (H40), SEQ ID NO:9 (H41); SEQ ID NO:10 (H42), SEQ ID NO:11 (H44), SEQ ID NO:12 (H45), SEQ ID NO:13 (H46), SEQ ID NO: 14 (H47), SEQ ID NO:15 (H48), SEQ ID NO:16 (H83), SEQ ID NO:17 (L4), SEQ ID NO:18 (L16), SEQ ID NO:19 (L24); SEQ ID NO:20 (L34), SEQ ID NO:21 (L35), SEQ ID NO:22 (L36), SEQ ID NO:23 (L37), SEQ ID NO:24 (L38), SEQ ID NO:25 (L39), SEQ ID NO:26 (L40), SEQ ID NO:27 (L41), SEQ ID NO:28 (L42), SEQ ID NO:29 (L43); SEQ ID NO:30 (L44), SEQ ID NO:31 (L45), SEQ ID NO:32 (L46), SEQ ID NO:33 (L47), SEQ ID NO:34 (L48), SEQ ID NO:35 (L49), SEQ ID NO:36 (L50), SEQ ID NO:37 (L51), SEQ ID NO:38 (L52), SEQ ID NO:39 (L53); SEQ ID NO:40 (L54), SEQ ID NO:41 (L55), SEQ ID NO:42 (L61), SEQ ID NO:43 (L63), SEQ ID NO:44 (L64), SEQ ID NO:45 (L72), SEQ ID NO:46 (L74), SEQ ID NO:47 (L75), SEQ ID NO:48 (L76), SEQ ID NO:49 (L125); SEQ ID NO:50 (L92), SEQ ID NO:51 (L104), SEQ ID NO:52 (L106), and SEQ ID NO:53 (L122), is used.

The transgenic mammal of the invention can be any species of mammal. Thus, the invention should be construed to include generation of transgenic mammals encoding the chimeric nucleic acid, which mammals include mice, hamsters, rats, rabbits, pigs, sheep and cattle. The methods described herein for generation of transgenic mice can be analogously applied using any mammalian species. Preferably, the transgenic mammal of the invention is a rodent and even more preferably, the transgenic mammal of the invention is a mouse. By way of example, Lukkarinen et al. (1997, Stroke 28:639-645), teaches that gene constructs which enable the generation of transgenic mice also enable the generation of other transgenic rodents, including rats. Similarly, nullizygous mutations in a genetic locus of an animal of one species can be replicated in an animal of another species having a genetic locus highly homologous to the first species.

To identify the transgenic mammals of the invention, pups are examined for the presence of the isolated nucleic acid using standard technology such as Southern blot hybridization, PCR, and/or RT-PCR. Expression of the nucleic acid in the cells and in the tissues of the mammal is also assessed using ordinary technology described herein. Further, the presence or absence of an anti-platelet autoantibody, or a biologically active fragment thereof, in the circulating blood of the transgenic animal can be determined, if the protein is secreted, by using, for example, Western blot analysis, or using standard methods for protein detection that are well-known in the art.

Cells obtained from the transgenic mammal of the invention, which are also considered "transgenic cells" as the term is used herein, encompass such as cells as those obtained from the anti-platelet autoantibody, or a biologically active fragment thereof, (+/−) and (−/−) transgenic non-human mammal described elsewhere herein, are useful systems for modeling diseases and symptoms of mammals which are believed to be associated with altered levels of an anti-platelet autoantibody, or a biologically active fragment thereof, expression such as an effect on platelet function, clearance, aggregation, activation, blood clotting (which can be assessed using a wide plethora of assays to detect an increase or decrease in blood formation), and any other disease, disorder or condition associated with expression of an anti-platelet autoantibody, or a biologically active fragment thereof, e.g., ITP. Moreover, as a marker of platelet function, expression levels of an anti-platelet autoantibody, or a biologically active fragment thereof, are also useful indicators in assessment of various diseases, disorders or conditions associated with an anti-platelet autoantibody, or a biologically active fragment thereof, (e.g., ITP, and the like).

Particularly suitable are cells derived from a tissue of the non-human knock-out or knock-in transgenic mammal described herein, wherein the transgene comprising the an anti-platelet autoantibody, or a biologically active fragment thereof, gene is expressed or inhibits expression of an anti-platelet autoantibody, or a biologically active fragment thereof, in various tissues. By way of example, cell types from which such cells are derived include fibroblasts and like cells of (1) the anti-platelet autoantibody, or a biologically active fragment thereof, (+/+), (+/−) and (−/−) non-human transgenic liveborn mammal, (2) the anti-platelet autoantibody, or a biologically active fragment thereof, (+/+), (−/−) or (+/−) fetal animal, and (3) placental cell lines obtained from the an anti-platelet autoantibody, or a biologically active fragment thereof, (+/+), (−/−) and (+/−) fetus and liveborn mammal.

One skilled in the art would appreciate, based upon this disclosure, that cells comprising decreased levels of an anti-platelet autoantibody, or a biologically active fragment thereof, decreased level of anti-platelet autoantibody, or a biologically active fragment thereof, activity, or both, include, but are not limited to, cells expressing inhibitors of anti-platelet autoantibody, or a biologically active fragment thereof, expression (e.g., antisense or ribozyme molecules).

Methods and compositions useful for maintaining mammalian cells in culture are well known in the art, wherein the mammalian cells are obtained from a mammal including, but not limited to, cells obtained from a mouse such as the transgenic mouse described herein.

Recombinant cells expressing an anti-platelet autoantibody, or a biologically active fragment thereof, can be administered in ex vivo and in vivo therapies where administering the recombinant cells thereby administers the protein to a cell, a tissue, and/or an animal. Additionally, the recombinant cells are useful for the discovery of an anti-platelet autoantibody, or a biologically active fragment thereof, ligand and anti-platelet autoantibody-associated cell pathway(s).

The transgenic mammal of the invention, rendered susceptible to ITP, and the like, such as, for example, an anti-platelet autoantibody, or a biologically active fragment thereof, knock-in mouse, can be used to study the pathogenesis of this disease and the potential role of the anti-platelet autoantibody, or a biologically active fragment thereof, therein. Such a model system could be used to develop novel more specific therapies for ITP such as the efficacy of Staphylococcal Protein A (SpA)-induced B-cell deletion or the use of autoantibody-blocking reagents.

VI. Compositions

The invention includes a composition comprising an isolated nucleic encoding a mammalian anti-platelet autoantibody, or a biologically active fragment thereof. Preferably, the composition comprises a pharmaceutically acceptable carrier.

The invention includes a composition comprising an isolated nucleic complementary to a nucleic acid, or a portion thereof, encoding a mammalian an anti-platelet autoantibody, or a biologically active fragment thereof, which is in an antisense orientation with respect to transcription. Preferably, the composition comprises a pharmaceutically acceptable carrier.

The invention includes a composition comprising an isolated mammalian anti-platelet autoantibody, or a biologically active fragment thereof, as described herein. Preferably, the composition comprises a pharmaceutically-acceptable carrier. In one aspect, the mammal is a human. In another aspect, the autoantibody is H44L4.

The invention further includes a composition comprising an isolated nucleic acid encoding a peptide inhibitor of an anti-platelet autoantibody, or a biologically active fragment thereof. Preferably, the composition comprises a pharmaceutically acceptable carrier.

The compositions can be used to administer a peptide inhibitor of an anti-platelet autoantibody, or a biologically active fragment thereof, to a cell, a tissue, or an animal or to inhibit binding of the autoantibody with a platelet. The compositions are useful to treat a disease, disorder or condition mediated by binding of the autoantibody with a platelet such that decreasing binding of the autoantibody with a platelet, is beneficial to a mammal. That is, where a disease, disorder or condition (e.g., ITP, among others) in an animal is mediated by, or associated with, binding of an anti-platelet autoantibody with a platelet, the composition can be used to modulate such binding.

For administration to the mammal, a polypeptide, or a nucleic acid encoding it, and/or an antisense nucleic acid complementary to all or a portion thereof, can be suspended in any pharmaceutically acceptable carrier, for example, HEPES buffered saline at a pH of about 7.8.

Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., N.J.).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an anti-platelet autoantibody, or a biologically active portion thereof, and/or a nucleic acid encoding the same, according to the methods of the invention.

Compounds which are identified using any of the methods described herein may be formulated and administered to a mammal for treatment of ITP, thrombosis, and the like, are now described.

The invention encompasses the preparation and use of pharmaceutical compositions comprising a compound useful for treatment of arterial restenosis, adventitial fibrosis, negative remodeling, and the like, as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry-powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

VII. Methods A. Methods of Identifying a Useful Compound The present invention further includes a method of identifying an anti-platelet autoantibody in a mammal where the mammal is afflicted with a disease that is mediated by such an autoantibody. The method comprises producing a phage-display library from the B-cells contained within a sample of peripheral blood or splenic tissue of the mammal using methods that are well-known in the art. That is, it is well understood in the art that because B-cells are antigen-producing cells, a phage-display library made from such cells contains phage expressing and displaying a large number of antibodies (see, e.g., Chang et al. (1998, Blood 91:3066-3078); Roark et al., 2002, Blood 100:1388-1398). Preferably, the phage displaying the proteins can be panned on intact platelets using competitive cell-surface panning and magnetically activated cell sorting essentially as described previously (Siegel et al., 1997, J. Immunol. Methods 206:73-85) and U.S. Pat. No. 6,255,455, which is incorporated by reference herein.

The phage are then selected for their ability(ies) to bind to a surface protein present on intact platelets. Preferably, the protein is an integrin receptor, selected from the group of GPIa/IIa, GPIIb/IIIa, and GPIb/IX, among others. Even more preferably, the platelet protein is GPIIb/IIIa. The skilled artisan would appreciate, based upon the disclosure provided herein, that the method can readily be used to identify an autoantibody directed against any component present on an intact platelet. Such platelet component includes, but is not limited to, GPIa/IIa, GPIIb/IIIa, GPIb/IX, as well as other glycoproteins, glycolipids, lipids, or any other cell-surface moiety.

The animal from which the B-cells are obtained can be afflicted with a disease mediated by anti-platelet autoantibody binding with a platelet. In that way, autoantibodies involved in disease can be identified readily. Preferably, the animal is known to be producing an autoantibody that specifically binds with a platelet. More preferably, the autoantibody specifically binds with GPIa/IIa, GPIIb/IIIa, and GPIb/IX, where the animal can have an autoantibody that binds at least one of these molecules, and can have at least one autoantibody that binds each of the molecules, as well as an autoantibody that binds other molecules on the surface of a platelet.

The invention encompasses producing an autoantibody using B-cells obtained from a patient afflicted with ITP. This should not be construed to limit the invention in any way to an autoantibody specific for this, or any other, particular disease, disorder or condition mediated by binding of an autoantibody with a platelet. Nor, should this be construed to limit the invention to using only splenocytes as the source of B-lymphocytes, e.g., peripheral blood lymphocytes (PBLs), splenocytes, or both, can be used as starting material for autoantibody library construction. Therefore, the invention includes an autoantibody obtained using the methods disclosed herein where the phage display library is produced using the B-cells from a broad class of patients afflicted with any disease, disorder or condition mediated by autoantibody binding with a platelet, including, but not limited to, ITP and PTP. This is because, as would be appreciated by one skilled in the art, based upon the disclosure provided herein, the methods of the invention allow, for the first time, the rapid identification and isolation of an autoantibody specific for a surface component of a platelet, which component is exemplified herein, but is not limited to, GPIa/IIa, GPIIb/IIIa, and GPIb/IX.

The invention encompasses identifying an anti-platelet autoantibody that specifically binds a portion of component of a platelet. That is, by using a portion of the platelet antigen to screen the antibody-phage display library, an antibody can be selected which specifically binds with a desired portion of an antigen. This is exemplified elsewhere herein in that an anti-platelet autoantibody (i.e., H44L4) was produced which binds with a GPIIb/IIIa molecule where the molecule comprises from about from about amino acid residue number 447 to about amino acid residue number 1009 of $\alpha_{IIb}$ (SEQ ID NO:153, GenBank Acc. No. P08514), but the autoantibody does not bind GPIIb/IIIa where the molecule comprises the N-terminal portion of the GPIIb/IIIa, e.g. from about amino acid residue number 1 to about amino acid residue number 446 of $\alpha_{IIb}$ (based on the amino acid sequence of SEQ ID NO:153, which sets forth the full-length 1009 amino acids). Thus, the present invention takes advantage of the exquisite specificity of monoclonal antibodies and provides a method for producing an anti-platelet autoantibody, which autoantibody possesses the desired specificity for a platelet antigen of choice, or a precise portion thereof. Therefore, the method of the present invention is readily applicable to identification and production of a wide variety of anti-platelet autoantibodies where the platelet component (i.e., the target) is known, and where the specific portion of the component involved in platelet function, or disease pathology, is known.

This method provides a powerful tool for identifying anti-platelet autoantibodies that specifically bind with a platelet, which binding can mediate a disease, disorder or condition in a mammal. Further, the autoantibodies identified by this method have, as more fully disclosed elsewhere herein, a wide number of uses including, among other things, methods that exploit the binding of the autoantibody with a platelet, such as, use of the antibodies for imaging of blood clots, as well as use of the autoantibody to treat or prevent a blood clot in an animal. While it was known that such autoantibody was desirable for these, and other, uses, no human monoclonal IgG anti-platelet autoantibody had been identified prior to the present invention. The skilled artisan would appreciate that a human monoclonal IgG anti-platelet autoantibody represents an important improvement to prior art antibodies which were not of human origin, and suffered from serious drawbacks in that such intra-species autoantibodies were immunogenic when used in humans and produced undesired serious side-effects because of this immune reactivity. Accordingly, the present invention represents a vast improvement over prior art methods of producing an anti-platelet autoantibody and is the first successful method to produce platelet-specific human IgG autoantibodies from the immune repertoires of ITP patients.

The invention also encompasses a method of identifying a peptide that inhibits binding of an anti-platelet autoantibody with a platelet. The method comprises assessing the binding of an anti-platelet autoantibody with a platelet in the presence or absence of a peptide displaying phage. That is, the binding of an anti-platelet autoantibody with its ligand is assessed both in the presence of a phage displaying a specific peptide, in the absence of such phage, or in the presence of a phage displaying an irrelevant peptide (control phage). If a lower level of binding of the anti-platelet autoantibody with its ligand is detected in the presence of the specific phage, compared with the level of the autoantibody binding with its ligand in the absence of the phage or with control phage, this indicates that the peptide displayed by the phage inhibits binding of the anti-platelet autoantibody with the ligand.

The skilled artisan would understand, based upon the disclosure provided herein, that the present invention encompasses using a wide plethora of phages displaying numerous peptides. That is, the present invention is in no way limited by the peptide-displaying phage library that can be used to identify a peptide that detectably inhibits binding of an anti-platelet autoantibody with a platelet (i.e., a peptide inhibitor). Thus, although the data disclosed herein exemplify the invention by demonstrating the use of a commercially available phage display library expressing certain peptides (e.g., a 12-mer linear peptide library and a "cys-7-mer-cys" constrained peptide library), the invention is in no way limited to these, or any other, peptide phage display library or any particular peptide displayed. Indeed, the present invention includes using other peptides and peptide-display libraries such as are known in the art, or to be developed. For example, non-random peptide libraries based on the linear sequences of particular platelet membrane proteins may be constructed using techniques well known in the art.

The ability of the peptide displayed to inhibit binding of the anti-platelet autoantibody with its ligand can be assessed using a wide plethora of methods such as those exemplified herein, as well as those known in the art, or to be developed in the future. For instance, an ELISA-based assay where a solid substrate is coated with the ligand (i.e., also referred to as the "target") can be used, where phage that specifically bind with the target are selected. The phage selected are then assayed for their ability to inhibit the binding of an anti-platelet autoantibody known to otherwise specifically bind the same target (e.g., H44L4, H31L4, and the like). That is, the anti-platelet autoantibody can be bound with a substrate and binding of the autoantibody with its target, which target can be detected using a wide variety of methods, can be assessed using a wide plethora of methods based on detection of the target. The binding of the anti-platelet autoantibody with the target can be assessed in the presence or absence of the phage displaying the peptide of interest, which phage displayed peptide binds with the autoantibody thereby preventing binding of the autoantibody with its cognate antigen. Such methods are exemplified herein, and are well-known in the art.

The skilled artisan, based upon the disclosure provided herein, would appreciate that that peptides displayed by the phages disclosed herein were produced such that the carboxyl termini of the peptides were not "free". That is, the carboxyl terminus of each peptide was fused with an M13 pIII coat protein, such that the terminus did not carry a negative charge (due to the peptide bond with pIII). Thus, the free peptide, once isolated from the pIII coat protein portion, can have different properties than when the peptide was bound with the coat protein. One skilled in the art would understand that methods well-known in the art, such as, but not limited to, methods for capping the free COOH terminus to eliminate any negative charge associated therewith, can be used to substantially restore the binding activity of the peptide once it is isolated from the phage coat protein portion. Additionally, the ability of the peptide to affect the binding of the anti-platelet autoantibody with an intact platelet can also be assessed. That is, there are a wide variety of methods, such as, but not limited to, those exemplified herein and those known in the art, for assessing the binding of an autoantibody with a platelet, including, but not limited to, using a labeled autoantibody in conjunction with fluorescence activated flow cytometry. These peptides are extremely useful potential therapeutics for use in a disease, disorder or condition mediated by binding of an anti-platelet autoantibody with a platelet. This is because these peptides can inhibit the binding, which binding is required for the disease process. Further, as disclosed elsewhere herein, the peptide inhibitor can be used in combination therapy where the anti-platelet autoantibody is administered to a patient to affect, among other things, platelet function, and where it is then desirable or beneficial to reverse the effect of the autoantibody so administered.

The present invention encompasses any peptide identified by this method, as exemplified by, among others, 12-mer linear peptides P4-12 and P4-7, and C7C constrained peptides P4-2a and P3-4. The skilled artisan would realize, based upon the disclosure provided herein, that the invention is in no way limited to these, or any other, peptide inhibitor. Such peptide inhibitors of the binding of an anti-platelet autoantibody with a platelet antigen, an intact platelet, or both, have a wide variety of uses, including, but not limited to, uses where it is desirable to inhibit the binding of the autoantibody with a platelet, such as where such binding mediates a disease (e.g., ITP, and the like). Alternatively, peptides which neutralize the binding of platelet autoantibodies to their platelet target components may be useful for diagnostic assays analogous to the way natural or synthetic blood group substances can be used to identify the specificity of anti-red blood cell antibodies.

While the data disclosed herein exemplify that a peptide inhibitor of the invention can inhibit binding of an anti-platelet autoantibody (e.g., H44L4) with purified GPIIb/IIIa and/or with an intact platelet, the present invention is in no way limited to any particular anti-platelet antibody or any particular target component of a platelet.

B. Methods Relating to Autoantibody Binding with a Platelet Component

The present invention encompasses numerous methods based upon the binding of an anti-platelet autoantibody with a platelet, or a component thereof. These methods are important in that binding of autoantibodies with platelets mediates a number of effects on such platelets and their function(s), including mediating diseases, disorders or conditions, including, but not limited to, ITP and PTP. While the methods of treating, and the like, can be performed on a mammal, it should be understood that the methods of the invention are, preferably, performed on a human.

The invention encompasses a method for inhibiting blood clotting. The method comprises administering to a patient, an effective amount of an anti-platelet autoantibody that specifically binds with a platelet. The patient is in need of a treatment to inhibit blood clotting due to, among other things, having a thrombus or a risk of thrombus formation, including, but not limited to a variety of situations where thrombus formation or reformation (reocclusion) is to be prevented. For instance, the autoantibody can be administered to an individual (e.g., a mammal, such as a human) to prevent thrombosis in pulmonary embolism, transient ischemic attacks (TIAs), deep vein thrombosis, coronary bypass surgery, surgery to insert a prosthetic valve or vessel (e.g., in autologous, non-autologous or synthetic vessel graft).

The autoantibodies of the present invention can also be administered to an individual to prevent platelet aggregation and thrombosis in angioplasty procedures performed by balloon, coronary atherectomy, laser angioplasty or other suitable methods. The autoantibody can be administered prior to the angioplasty procedure (pre-angioplasty), during angioplasty, or post-angioplasty. Such treatment can prevent thrombosis and thereby reduce the rate of thrombotic complications following angioplasty, such as death, myocardial infarction, or recurrent ischemic events necessitating angioplasty (percutaneous transluminal coronary angioplasty, PTCA), or coronary bypass surgery.

For instance, administration of an anti-platelet autoantibody of the invention as adjuvant therapy prior to angioplasty can increase bleeding times and reduce platelet aggregation. The data disclosed herein demonstrating that an anti-platelet autoantibody inhibited, inter alia, platelet aggregation, activation, function, release of serotonin, binding to fibrinogen, and the like, indicate that inhibition of binding of an autoantibody with platelet GPIIb/IIIa can provide an in vivo antithrombotic effect in a human.

The anti-platelet autoantibody of the invention can be administered to an individual (e.g., a human) alone or in conjunction with a thrombolytic agent, such as a plasminogen activator (e.g., tissue plasminogen activator, urokinase, or streptokinase, recombinant tissue plasminogen activator), or an anticoagulant or anti-platelet agent, such as aspirin, heparin, or a coumarin anticoagulant (e.g., warfarin), to prevent or reduce reocclusion that can occur after thrombolysis and to accelerate clot lysis. The autoantibody, or a biologically active fragment, can be administered before, along with or subsequent to administration of the thrombolytic agent or anticoagulant, in amounts sufficient to prevent platelet aggregation that can result in reocclusion.

An effective amount (e.g., an amount sufficient for inhibition of, inter alia, platelet aggregation, function, activation, and thereby of inhibition of thrombus formation) of the antibody or antibody fragment can be given parenterally, preferably intravenously, in a pharmaceutically acceptable vehicle such as sterile saline. Buffered media may be included. The antibody formulation can contain additional additives, such as a stabilizer (e.g., Polysorbate 80, USP/NF). The antibody can be administered in a single dose, continuously, or in multiple infusions (e.g., a bolus injection, followed by continuous infusion). Alternatively, the antibody can be administered by a controlled release mechanism (e.g., by a polymer or patch delivery system) or by another suitable method. The amount to be administered will depend on a variety of factors such as the clinical symptoms, weight of the individual, whether other drugs (e.g., thrombolytic agents) are administered. Determinations of formulations, dosage, and treatment regimen are routinely performed by those skilled in the art, and are discussed in, among other things, many treatises available to the skilled artisan (e.g., Genaro, ed., 1985, Remington's Pharmaceutical Sciences, Mack Publishing Co., Easton, Pa.), as more fully set forth elsewhere herein.

The invention encompasses inhibiting platelet aggregation using, for example, an anti-platelet autoantibody that specifically binds with GPIIb/IIIa. Such an autoantibody is exemplified by H44L4, which requires the presence of the portion of $\alpha_{IIb}$ comprising from about amino acid residue number 447 to about amino acid residue number 1009, based upon the amino acid sequence provided in GenBank Accession No. P08514 (also referred to as integrin alpha-IIb precursor, platelet membrane glycoprotein IIb, GPalpha IIb, GPIIb, and CD41 antigen; SEQ ID NO:153). However, the invention is not limited to this platelet protein, nor to any specific portion thereof. For example, anti-platelet autoantibodies specific to GPIb/IX may be effective at blocking the interaction of platelets with von Willebrand factor multimers and prevent the thrombus formation, morbidity, and mortality associated with the disease thrombotic thrombocytopenic purpura (TTP). In addition, anti-platelet autoantibodies to other platelet membrane components, including the platelet Fc receptors, may prevent the binding of anti-platelet factor4/heparin complex autoantibodies to platelets and prevent the thrombocytopenia and thrombosis associated with the disorder heparin-induced thrombocytopenia/thrombosis (HIT/T).

Thrombotic thrombocytopenic purpura (TTP) is a disease in which an individual's platelets clump and adhere inappropriately resulting in small vessel thrombosis (clots) which may occur in many organs and affect their function (particularly the brain and kidneys). Without immediate treatment, which consists of plasmapheresis and reinfusion of fresh frozen plasma, mortality is greater than 90%.

Recent studies have significantly advanced understanding of the pathophysiology of the acute form of this disorder (e.g., Tsai et al., 1998, NEJM 339:1585-1594). That is, an autoantibody develops in the bloodstream which inhibits the action of a serum enzyme known as the "von Willebrand Factor cleaving protease". The function of this enzyme is to cleave vWF (von Willebrand factor), a serum protein required for normal platelet function, into small functional units. Without the normal activity of this enzyme, vWF remains in inappropriately large forms as produced by endothelial cells (termed "unusually large multimers"). These large multimers then inappropriately interact with GPIb/IX, causing an individual's platelets to clump and adhere to endothelial surfaces without cause.

Presently, it is understood why plasmapheresis with FFP infusion is an effective treatment for TTP. More particularly, the removal of patient plasma during the procedure serves to remove the unwanted protease inhibitor, and the concomitant replacement of patient plasma with fresh normal plasma serves to supply the patient with active protease enzyme. With daily plasma exchange procedures (usually along with the additional of immunosuppressive medications), when successful, the patient's production of protease inhibitor ceases and treatment and/or alleviation of the disease is achieved.

Until a permanent "cure" is achieved and patients are undergoing daily plasmapheresis procedures for perhaps as long as a month or more, their platelets may continue to inappropriately clump and adhere and further aggravate the condition for which they originally presented, i.e., neurological, renal, and/or other organ damage due to obstructed blood flow from platelet thrombi (mediated inappropriately by vWF); resultant thrombocytopenia due to consumption of platelets, thus putting the patient at risk for hemorrhage elsewhere; and anemia due to fragmentation of red blood cells presumably as they are forced past the thrombi in the microvasculature. For some patients, plasmapheresis does not work rapidly enough and they die (usually from brain or cardiac infarction) before the inappropriate interaction between vWF and their platelets is halted. For other patients who cannot quickly get to a medical center capable of performing the plasmapheresis procedure, they die before treatment can be initiated.

It would be desirable to have an agent that can inhibit the interaction of vWF multimers with their main platelet receptor, GPIb/IX, to infuse into patients acutely and during treatment to break the cycle of inappropriate vWF-mediated platelet clumping and adherence and subsequent organ damage and other pathological features of the disease. A human autoantibody to GPIb/IX developed using methods described herein can serve as a powerful therapeutic by binding to platelet GPIb/IX, as demonstrated elsewhere herein, thereby preventing and/or inhibiting undesirable vWF/platelet interaction.

In sum, the invention includes using an anti-platelet autoantibody to inhibit blood clotting wherein the autoantibody binds a platelet such that the binding inhibits the formation of a clot by the platelet.

Without wishing to be bound by any particular theory, the inhibition of platelet function by the autoantibody can be simply due to steric hindrance such that the platelet is unable to bind with a ligand, which binding then mediates various effects required for clot formation, or other platelet function. Alternatively, the binding of the autoantibody with the platelet (i.e., with a platelet component) can alter the conformation of the target antigen on the platelet or prevent such an alteration from occurring naturally. Such effect can affect the ability of the platelet to activate, aggregate, secrete serotonin, and the like, in that it may be that a conformational change in the target protein (also referred to as the platelet component), which is otherwise required for platelet function, is inhibited by the binding of the autoantibody with the target. For example, studies comprising structural investigations regarding the mechanism of regulation of integrin activation suggest that in the inactive state, the αβ heterodimeric stalk-like chains are sharply bent over half-way through their extracellular length (Takagi et al., 2002, Cell, 110:599-611). Upon activation, the molecules convert to a more upright orientation exposing the ligand (fibrinogen)-binding domain near their globular heads. The region of αIIb required for the binding of H44L4, a platelet inhibiting autoantibody described in this invention, coincides with the region of the bend. It is tempting to speculate that H44L4 may bind to the integrin, stabilize its inactive state, and prevent the conformational changes required for its activation and subsequent binding of its ligand; however, the present invention is in no way limited to this, or any other, possible mechanism whereby the autoantibody of the invention affects platelet function, and the like.

The invention encompasses administering to the patient, an effective amount of a peptide inhibitor, such that the binding of the autoantibody administered to the patient with the platelet is now inhibited. Such inhibition is desirable where blood clotting is no longer desired and/or does not provide a therapeutic benefit, to the patient. This is especially true where a patient that was previously in need of inhibition of blood clotting due to, e.g., myocardial infarction, and now requires surgical intervention such that decreased clotting presents an undesirable risk to the surgical procedure. Unlike prior art methods relating to administration of an anti-platelet chimeric mouse-human autoantibody (e.g., ReoPro™), which is not reversible, the methods of the invention provide a reversible method of inhibiting blood clotting whereby a peptide inhibitor of the binding of the autoantibody with GPIIb/IIIa can be administered, thereby rapidly reversing the anti-clotting effect of the autoantibody. Developing peptide inhibitors to ReoPro may be problematic since their conformation would be expected to mimic the fibrinogen-binding domain of $\alpha_{IIb}$ and would thus be expected to be rapidly bound up by the relatively enormous quantity of free plasma fibrinogen leaving insufficient amounts to neutralize ReoPro™. The present invention circumvents these limitations and allows the effect of the autoantibody of the invention to be optionally reversed where it is desired to abrogate the effect of administering the autoantibody to a mammal, more specifically, to a human. This is a substantial improvement over prior methods for affecting platelet function and activity, including, but not limited to, use of ReoPro™.

Moreover, ReoPro™ is not specific to GPIIb/IIIa as it is known to bind to the vitronectin receptor, among other substances. Unlike ReoPro™, the data disclosed herein (e.g., FIG. 13) demonstrate that H44L4 does not bind to the vitronectin receptor. Thus, the autoantibody of the invention presents a substantial improvement over non-specific antibodies such as, but not limited to, ReoPro™, where binding of the autoantibody with vitronectin is not desired.

While the present invention provides a number of peptide inhibitors (e.g., P4-12, P4-7, P4-2a, and P34) that inhibit binding of an anti-platelet autoantibody (e.g., H44L4) binding with a platelet component (e.g., GPIIb/IIIa), the skilled artisan would appreciate, based upon the teachings provided herein, that the invention is not limited to these, or any other particular, peptide inhibitors, autoantibody, or target antigen. Rather, armed with the teachings of the invention, one skilled in the art would be able to readily identify additional targets, autoantibodies, and peptide inhibitors, to practice the methods of the invention as disclosed herein.

The invention encompasses a method of inhibiting platelet aggregation. This is because, as demonstrated by the data disclosed elsewhere herein, binding of an anti-platelet autoantibody with a platelet (such as, but not limited to, by binding with a protein on the platelet, e.g., GPIa/IIa, GPIIb/IIIa, and GPIb/IX) can inhibit, among other things, platelet aggregation. Thus, the method comprises contacting a platelet with an effective amount of an anti-platelet autoantibody, or a biologically active fragment thereof, such that platelet aggregation is inhibited. Such methods are useful to treat or alleviate a disease, disorder or condition mediated by platelet aggregation, e.g., thrombotic thrombocytopenic purpura (TTP) and heparin-induced thrombocytopenia/thrombosis (HIT/T).

Similarly, the invention encompasses a method of inhibiting platelet activation. More particularly, the method comprises contacting a platelet with an effective amount of an anti-platelet autoantibody, or a biologically active fragment thereof. This is because, as demonstrated by the data disclosed elsewhere herein, binding of an anti-platelet autoantibody with a platelet can inhibit platelet activation, as exemplified by the inhibition in serotonin release and inhibition of ligand (fibrinogen) binding. Such methods are useful where inhibiting platelet activation can provide a benefit, such as, but not limited to, where inhibiting platelet activation inhibits, among other things, platelet aggregation, the benefits of which are discussed elsewhere previously herein.

The invention also includes a method of inhibiting platelet function, where such function includes, but is not limited to, any biological activity associated with a platelet. Such activity includes, but is not limited to, the formation of platelet aggregates, platelet binding to von Willebrand Factor, collagen, and other substances, the adherence of platelets to endothelial cells, and the secretion of various substances from intracellular stores (e.g., serotonin, and the like), and the like. The method comprises contacting a platelet with an effective amount of an anti-platelet autoantibody, or a biologically active fragment thereof. This is because it has been demonstrated elsewhere herein that such binding inhibits platelet function. Further, the present invention is not limited to the specific antibody (H44L4) or platelet target (GPIIb/IIIa) exemplified elsewhere herein. Instead, the invention encompasses such autoantibodies as are produced according to the methods of the invention, as well as any platelet target disclosed herein, known in the art, or identified in the future.

The invention encompasses a method of inhibiting binding of an anti-platelet autoantibody, or a biologically active fragment thereof, with a platelet. The method comprises contacting the platelet with an effective amount of a peptide inhibitor of the autoantibody. This is because the data disclosed herein demonstrate that where an anti-platelet autoantibody binds with a platelet, such binding can be inhibited using a peptide inhibitor. Further, the present invention is not limited to the specific antibody (H44L4), platelet target (GPIIb/IIIa), or peptide inhibitor (12-mer linear peptides and C7C constrained peptides) exemplified elsewhere herein. Instead, the invention encompasses such autoantibodies and peptide inhibitors as are produced according to the methods of the invention, as well as any platelet target disclosed herein, known in the art, or identified in the future.

The invention encompasses a method of treating ITP in a mammal (more preferably, a human). The method comprises administering to an animal afflicted with ITP, an effective amount of a compound that specifically kills a B-lymphocyte expressing VH3-30. This is because, as demonstrated by the date disclosed elsewhere herein, anti-platelet autoantibodies comprising VH3-30 can mediate a variety of diseases, disorders or conditions wherein an anti-platelet autoantibody specifically binds with a platelet, or component thereof, thereby mediating the disease, disorder or condition. One such disease, disorder or condition is ITP and the data disclosed herein demonstrate, for the first time, that a substantial number of the anti-platelet autoantibodies that mediate the disease comprise VH3-30. Accordingly, one skilled in the art, based upon the disclosure provided herein, would appreciate that deletion of B-lymphocytes expressing such deleterious anti-platelet autoantibodies would provide a therapeutic benefit to an animal afflicted with a disease, disorder, or disease mediated by production of such autoantibodies, e.g., ITP.

That is, by cloning anti-platelet autoantibody repertoires from ITP patients, the data disclosed herein demonstrate the novel finding that there is an apparent restriction in autoantibody heavy chain gene usage to the VH3-30 immunoglobulin gene. Exploiting this restriction can be used to target the deletion of specific autoantibody-producing B-cells from patients with, inter alia, ITP.

The skilled artisan, armed with the teachings disclosed herein, would understand that there are a wide plethora of methods for specifically deleting a B-lymphocyte of interest in an animal. For instance, as discussed elsewhere herein, the specific elimination of B-lymphocytes expressing an antibody comprising VH3-30 using Staphylococcal protein A can be used to selectively target and delete B-lymphocytes expressing an anti-platelet autoantibody of the invention. Additionally, modification of SpA (termed "mod SpA") using iodination provides a SpA that lacks Fc binding activity but which retains the ability to interact with Fab, more specifically, with VH3-30. Indeed, the data disclosed elsewhere herein (e.g., FIG. 7) demonstrate that mod SpA binds the anti-platelet autoantibodies of the invention comprising VH3-30. These data demonstrate, for the first time, the use of SpA, either modified or unmodified, to selectively delete B-cells expressing an anti-platelet autoantibody of interest, thereby treating a disease, disorder or condition mediated by such autoantibody (e.g., ITP, and the like).

One skilled in the art would further appreciate, based upon the disclosure provided herein, that there are many methods where a B-cell of interest can be selectively eliminated from the B-cell repertoire. For instance, another method of exploiting the VH3-30 restriction of anti-platelet autoantibodies demonstrated elsewhere herein, is to develop agents (e.g., an antibody) that is specific for the VH3-30 generic structure (i.e., specific for common framework determinants in the variable region that distinguish VH3-30 antibodies from others independently of the actual specificity of the antibody). Such an antibody reagent could be obtained using methods well known in the art for generating murine monoclonals to particular human immunoglobulin gene products. Such murine antibodies to VH3-encoded antibodies actually already exist and some show similar binding profiles to VH3-30 and homologous antibodies as SpA (e.g., Potter et al., 1998, Molec. Immunol. 35:1179-1187). For therapeutic use, it may be desirable for such an antibody to be "human" in structure, so producing such hybridomas in mice that are transgenic for human heavy and light chain Ig genes, such as by using the Xenomouse™ produced by Abgenix Corp., can be performed. Additionally, as more fully disclosed elsewhere herein, any antibody of interest can be "humanized" (see, e.g., ReoPro™ as an example of a humanized mouse monoclonal autoantibody) using methods well-known in the art or to be developed in the future.

Alternatively, synthetic antibody phage display libraries which comprise human-like antibody sequences produced in vitro could be used (reviewed in Siegel, 2001, Trans. Med. Rev. 15:35-52). Such antibodies, irrespective of their derivation, could be coupled to toxic molecules to comprise immunotoxins that would destroy VH3-30 expressing B-cells by virtue of their binding to cell-surface immunoglobulin.

Production of immunotoxins, which are typically bicistronic molecules comprising an antibody-binding domain, that is, an immunoreactive domain that specifically binds with an antigen, and a toxin domain, is well-known in the art, and is described in, among others, Dohlsten et al. (1994, Proc. Natl. Acad. Sci. USA 91:8945-8949), and Rosenblum et al. (U.S. Pat. No. 5,624,827). Thus, the skilled artisan would understand, based upon the disclosure provided herein, that these and other methods well-known in the art for producing immunotoxins can be used to selectively delete B-lymphocytes expressing the anti-platelet autoantibodies of the invention, including, but not limited to, B-cells expressing an antibody comprising a VH3-30 domain.

Instead of anti-VH3-30 immunotoxins, which could conceivably destroy all B-cells which use the VH30-30 heavy chain, more specific immunotherapies for ITP can comprise agents specific for the particular idiotype or idiotypes of the anti-platelet autoantibodies made by the given patient. Such idiotypes could be determined from the cloning of patient immune repertoires such as described herein, or actually use the particular idiotypes expressed by the particular anti-platelet autoantibodies claimed. Agents specific to the variable regions of those platelet autoantibodies (irrespective of whether they are encoded by VH3-30) could be designed. Such agents could comprise specific peptides, such as those or others obtained using the methods described herein, or by generating anti-idiotypic antibodies to the platelet-autoantibodies using hybridoma or synthetic phage libraries described above. That is, one skilled in the art would appreciate, based upon the disclosure provided herein, that the peptides that specifically bind with the anti-platelet autoantibody thereby inhibiting binding of the autoantibody with a platelet, or a component thereof (e.g., P4-12 (SEQ ID NO:111); P3-4 (SEQ ID NO:112); P4-7 (SEQ ID NO:113); P4-2a (SEQ ID NO:114); P73-11 (SEQ ID NO:116); P123-10 (SEQ ID NO:118); P74-4 (SEQ ID NO:120); P73-10 (SEQ ID NO:122); P74-3 (SEQ ID NO:124); P74-9 (SEQ ID NO:126); P74-5 (SEQ ID NO:128); P73-9 (SEQ ID NO:130); P124-8 (SEQ ID NO:132); P123-11 (SEQ ID NO:134); P124-1 (SEQ ID NO:136); P73-2 (SEQ ID NO:138); P73-6 (SEQ ID NO:140); P124-11 (SEQ ID NO: 142); P124-2 (SEQ ID NO: 144); P73-7 (SEQ ID NO: 146); P74-1a (SEQ ID NO:148); P123-8 (SEQ ID NO:150); P74-8 (SEQ ID NO:152)), can also be used to target the immunotoxin such that a specific B-cell expressing the autoantibody of interest is deleted from the antibody-producing repertoire.

C. Methods of Diagnosis and Assessment of Therapies

The present invention includes methods of diagnosis certain diseases, disorders, or conditions such as, but not limited to, using peptide inhibitors in neutralization assays to help characterize their specificity(ies) as mentioned earlier. In addition, human anti-platelet autoantibodies to platelet membrane components such as GPIIb/IIIa, GPIb/IX, and GPIa/IIa can serve as positive controls for commercial ELISA assay kits for detecting platelet autoantibodies in patient serum or platelet eluates. Currently, such kits package vials of human serum derived from known ITP patients for use as positive controls. Such materials are of limited supply, expensive to collect, of uncontrolled composition, and serve as an infectious disease risk to laboratory workers.

VIII. Kits

The invention includes various kits which comprise a compound, such as a nucleic acid encoding an anti-platelet autoantibody, an anti-platelet autoantibody, a peptide inhibitor of such binding, or a nucleic acid encoding the peptide inhibitor, and/or compositions of the invention, an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for inhibiting blood clotting. The kit is used pursuant to the methods disclosed in the invention. Briefly, the kit may be used to administer an anti-platelet autoantibody of the invention, or a biologically active fragment thereof, to a mammal (e.g., a human) having a thrombus, or at risk of thrombus formation. This is because, as more fully disclosed elsewhere herein, binding of the autoantibody with the platelet mediates decreased blood clotting wherein the decreased clotting can mediate a beneficial effect.

The kit further comprises an applicator useful for administering the autoantibody to the mammal. The particular applicator included in the kit will depend on, e.g., the method used to administer the autoantibody, as well as the mammal to which the autoantibody is to be administered, and such applicators are well-known in the art and may include, among other things, a pipette, a syringe, a dropper, and the like. Moreover, the kit comprises an instructional material for the use of the kit. These instructions simply embody the disclosure provided herein.

The kit includes a pharmaceutically-acceptable carrier. The composition is provided in an appropriate amount as set forth elsewhere herein. Further, the route of administration and the frequency of administration are as previously set forth elsewhere herein.

In one aspect, the kit further comprises a peptide inhibitor of binding of the anti-platelet autoantibody with a platelet. Such peptide inhibitors, and methods of producing them, are disclosed elsewhere herein. This kit provides a method of reversibly inhibiting blood clotting, since administering the peptide inhibitor inhibits the biding of the autoantibody with the platelet, thereby inhibiting the anti-coagulatory effect of the autoantibody as more fully discussed elsewhere herein.

The present invention includes a kit for inhibiting platelet aggregation. The kit comprises an effective amount of an anti-platelet autoantibody, or a biologically active fragment thereof.

The kit further comprises an applicator useful for administering the autoantibody. The particular applicator included in the kit will depend on, e.g., the method used to administer the autoantibody, and such applicators are wel-known in the art and may include, among other things, a pipette, a syringe, a dropper, and the like. Moreover, the kit comprises an instructional material for the use of the kit. These instructions simply embody the disclosure provided herein.

The present invention includes a kit for inhibiting platelet function. The kit comprises an effective amount of an anti-platelet autoantibody, or a biologically active fragment thereof.

The kit further comprises an applicator useful for administering the autoantibody. The particular applicator included in the kit will depend on, e.g. the method used to administer the autoantibody, and such applicators are well-known in the art and may include, among other things, a pipette, a syringe, a dropper, and the like. Moreover, the kit comprises an instructional material for the use of the kit. These instructions simply embody the disclosure provided herein.

The present invention includes a kit for inhibiting platelet activation. The kit comprises an effective amount of an anti-platelet autoantibody, or a biologically active fragment thereof.

The kit further comprises an applicator useful for administering the autoantibody. The particular applicator included in the kit will depend on, e.g., the method used to administer the autoantibody, and such applicators are well-known in the art and may include, among other things, a pipette, a syringe, a dropper, and the like. Moreover, the kit comprises an instructional material for the use of the kit. These instructions simply embody the disclosure provided herein.

The present invention includes a kit for inhibiting binding of an anti-platelet autoantibody, or a biologically active fragment thereof, with a platelet, or a platelet component. The kit comprises an effective amount of a peptide inhibitor. Such peptide inhibitor includes, but is not limited to, P4-12 (SEQ ID NO: 11); P3-4 (SEQ ID NO:112); P4-7 (SEQ ID NO:113); P4-2a (SEQ ID NO:114); P73-11 (SEQ ID NO: 116); P123-10 (SEQ ID NO:118); P74-4 (SEQ ID NO:120); P73-10 (SEQ ID NO:122); P74-3 (SEQ ID NO:124); P74-9 (SEQ ID NO:126); P74-5 (SEQ ID NO:128); P73-9 (SEQ ID NO: 130); P124-8 (SEQ ID NO:132); P123-11 (SEQ ID NO:134); P124-1 (SEQ ID NO: 136); P73-2 (SEQ ID NO: 138); P73-6 (SEQ ID NO: 140); P124-11 (SEQ ID NO:142); P124-2 (SEQ ID NO:144); P73-7 (SEQ ID NO:146); P74-1a (SEQ ID NO:148); P123-8 (SEQ ID NO:150); P74-8 (SEQ ID NO:152).

The kit further comprises an applicator useful for administering the peptide inhibitor. The particular applicator included in the kit will depend on, e.g., the method used to administer the inhibitor, and such applicators are well-known in the art and may include, among other things, a pipette, a syringe, a dropper, and the like. Moreover, the kit comprises an instructional material for the use of the kit. These instructions simply embody the disclosure provided herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Example 1

Autoantibodies in Idiopathic Thrombocytopenic Purpura

Although idiopathic thrombocytopenic purpura (ITP) is the most common autoimmune hematologic disorder, little is known about the associated autoantibodies on a molecular level. Consequently, diagnostic assays and therapy for ITP lack specificity. To avoid technical limitations imposed by prior art B-cell immortalization methods, repertoire cloning (Fab/phage display) was used to clone platelet autoantibodies and examine the relation between immunoglobulin (Ig) gene usage, clonality, and antigen specificity. Phage display libraries were constructed from splenocytes from 2 patients with chronic ITP, and competitive cell-surface selection was used to isolate several dozen unique IgG platelet-specific autoantibodies. That is, antibody phage display, a molecular approach for cloning human immune repertoires (Siegel et al., 2001, Transfus. Med. Rev. 15:35-52), was combined with a novel competitive cell-surface-selection scheme (Siegel et al., 1997, J. Immunol. Methods 206:73-85), to isolate and study repertoires of IgG anti-platelet autoantibodies from 2 unrelated patients with chronic ITP. Using this strategy, dozens of IgG platelet-reactive autoantibodies were isolated from each patient, thus permitting a comprehensive analysis of their genetic origin, extent of somatic mutation, and clonal relatedness.

The data disclosed herein demonstrate that platelet-reactive Fabs in both patients were associated almost exclusively with rearrangements of a single Ig heavy-chain variable region gene (VH3-30), despite an apparent diversity of antigen specificities. Comparative analysis of platelet-reactive Fab Ig gene rearrangements from each patient suggested that they evolved from a restricted number of B-cell clones through somatic mutation with high replacement to silent mutation ratios. Although VH3-30-encoded heavy chains were found with light chains encoded by several different Ig genes, molecular repairing experiments showed exquisite restriction on the specific heavy- and light-chain pairings that permitted platelet reactivity.

Together, these data demonstrate, for the first time, that the development of platelet-reactive antibodies associated with ITP is driven by an encounter with diverse platelet antigens through the clonal expansion of B cells using genetically restricted and highly specific combinations of heavy- and light chain gene products. The extraordinarily high usage of the VH3-30 heavy-chain gene in these patients provides important advances relating to the pathogenesis, diagnosis, and management of chronic ITP.

Platelet Preparations:

Platelet-rich plasma (PRP) was prepared by centrifuging (500×g) freshly isolated whole blood collected in sodium citrate (final concentration, 10.5 mM/L) containing 3 µM/L prostaglandin E1 (PGE1; Sigma Chemicals, St Louis, Mo.) at room temperature for 15 minutes. For some experiments, platelets were obtained from fresh banked platelet concentrates derived from CP2D-anticoagulated whole blood (Fenwall; Baxter Healthcare, Deerfield, Ill.). PRP from both sources was washed 3 times in acid-citrate-dextrose (ACD; 145 mM/L sodium chloride, 5 mM/L citric acid, 9 nM/L sodium citrate, and 17 mM/L dextrose [pH 6.5]) supplemented with 1% wt/vol bovine serum albumin (BSA).

Patients:

Fab/phage display libraries were constructed from splenic mononuclear cells from 2 unrelated adults with chronic ITP (ITP patient A and ITP patient B) and one control patient with thrombocytopenia but not ITP. Both patient A (a 56-year-old man) and patient B (a 43-year-old woman), had ITP refractory to prednisone and IVIG for at least 8 months. After splenectomy, platelet counts rose to the normal range. Patient A subsequently died of unrelated causes, and patient B has been in clinical remission for more than 4 years. Splenocytes from the control patient, a 65-year-old man with noninimune, multifactorial thrombocytopenia, were harvested at autopsy after he died of respiratory failure.

Construction of Fab/Phage Display Libraries

Using previously described methods for cloning IgG1 κ and λ immune repertoires described in Siegel et al. (1994, Blood 83:2334-2344), total RNA was prepared from about $10^8$ splenocytes. Heavy- and light-chain-rearranged Ig gene segments were amplified by reverse transcriptase-polymerase chain reaction, and the DNA was cloned into a phagemid expression vector (pComb3H; Scripps Research Institute, La Jolla, Calif.). After electroporation into XL1-Blue bacteria (Stratagene, La Jolla) and coinfection with VCSM13 helper phage (Stratagene), Ig DNA was packaged into filamentous phage particles that expressed the human Fab molecules fused to the pIII bacteriophage coat protein.

Panning Fab/Phage Display Libraries

Fab/phage display libraries were enriched for platelet-reactive Fabs by a modification of a previously described method using competitive cell surface selection and magnetically activated cell sorting as described in Siegel et al. (1997, J. Immunol. Methods 206:73-85). Briefly, platelets were washed free of BSA in phosphate-buffered saline (PBS) and PGE1, were resuspended to a concentration of $5 \times 10^8$/mL, and were surface biotinylated by adding sulfo-N-hydroxysuccinimide biotin (Pierce, Rockford, Ill.) to 400 µg/mL. After 2 washes with ACD and BSA, $2 \times 10^8$ biotinylated platelets were incubated with 20 µL streptavidin-coated paramagnetic microbeads (Miltenyi Biotec, Sunnyvale, Calif.) for 10 minutes at room temperature in a total volume of 100 µL ACD, BSA, and PGE1. ACD-BSA buffer (1 mL) containing about 5-fold excess (by surface area) human red blood cells (RBCs; $1 \times 10^7$) was added. The cell admixture was centrifuged and resuspended in 50 µL ACD, BSA, and PGE1 containing about $3 \times 10^{11}$ colony-forming units of Fab/phage display library. After a 2-hour incubation at room temperature with intermittent mixing, the suspension of platelets, RBCs, and phage was loaded on a MiniMACS column (Mitenyi Biotec, Germany) pre-equilibrated with ACD and BSA. Column washes (to remove RBCs and irrelevant Fab-phage), elution of platelet-bound Fab-phage, and amplification of panned libraries were performed as described previously in Siegel et al. (1997, J. Immunol. Methods 206:73-85).

Production of Soluble Anti-Platelet Fab Ig

To screen, isolate, and characterize individual monoclonal platelet-binding Fabs, randomly picked bacterial colonies derived from phage titering plates were grown to an optical density at 600 nm of 0.5, isopropyl-β-D-thiogalactopyranoside (1 mM/L) was added, and cultures were shaken overnight at 30° C. Soluble Fabs were isolated from bacterial pellets by osmotic shock as in Chang et al. (1998, Blood 91:3066-3078) and used in flow cytometric experiments and enzyme-linked immunosorbent assays (ELISAs) without further purification. Where indicated, soluble Fabs were purified by nickel-chelation chromatography as in Siegel et al. (1994, Blood 83:2334-2344). Aliquots of bacterial pellets were used to prepare plasmid DNA (Qiawell Plus; Qiagen, Valencia, Calif.) for nucleotide sequencing or antibody chain shuffling. Heavy- and light-chain DNA was sequenced and analyzed as described previously in Chang et al. (1998, Blood 91:3066-3078). Because of the large number of sequences (greater than about 60), only alignments of the predicted amino acid sequences for a subset of antibodies were depicted in Roark et al. (2002, Blood 100:1388-1398) and the remaining sequence alignments were provided on the publicly available website for the journal, i.e., *Blood*, all of which is incorporated by reference as if set forth in its entirety herein Further, all of the sequence data is disclosed elsewhere herein (see, e.g., FIGS. 2A through 2D).

Characterization of Antibody Binding by Flow Cytometry

Platelets were stained by using 5 µL PRP (~$5 \times 10^6$ platelets) and 50 µL Fab. After a 30-minute incubation, platelets were washed with ACD and BSA, and bound antibody was detected by using a phycoerythrin (PE)-conjugated F(ab)2 fragment of goat antihuman F(ab)2-specific Ig (Jackson ImmunoResearch, West Grove, Pa.) diluted 1:25 in wash buffer. Samples were analyzed using a microfluorometer (FACScan; Becton Dickinson, Mountain View, Calif.). Forward- and side-scatter gates for platelet populations were determined by using murine antihuman GPIIIa (SSA6; Dr J.

Bennett, University of Pennsylvania) counterstained with PE-conjugated goat antimouse reagent (Southern Biotechnology, Birmingham, Ala.). Platelets from 3 unrelated donors with type I Glanzmann thrombasthenia were provided by Dr. M. Poncz (University of Pennsylvania). A stable K562 cell line expressing GPIa/IIa was provided by Dr M. Zutter (Washington University, St Louis, Mo.).

Blocking experiments were conducted to compare the repertoires of recombinant platelet-reactive autoantibodies from ITP patients A and B with those in the serum of other patients with chronic ITP. Platelet aliquots were preincubated with each of 19 different ITP serum samples or a pool of normal serum, then mixed with antibodies from ITP patient A or B expressed as phage displayed Fabs. Blocking of recombinant patient autoantibodies by ITP serum was then detected with biotinylated anti-M13 antibody and PE-streptavidin as in Chang et al. (1998, Blood 91:3066-3078). Binding of recombinant autoantibodies in the presence of normal serum was defined as 100%, and inhibition in the presence of ITP serum was normalized to that value. Administration of IVIG to ITP patients A and B just before splenectomy precluded use of their serum in competition assays.

Characterization of Antibody Binding by ELISA and Immunofluorescence:

Antibodies to platelet GPIIb/IIIa, GPIb/IX, or GPIa/IIa were measured by using a PakAuto kit (GTI, Brookfield, Wis.); those to cardiolipin were assessed with a QuantaLite kit (Inova, San Diego, Calif.). Binding to cytoplasmic or nuclear determinants was assessed by immunofluorescence with HEp-2 cells (ANA Kit, Antibodies Incorporated, Davis, Calif.).

Immunoprecipitation of Platelet-Fab Immune Complexes:

Immunoprecipitation of biotinylated platelet membrane proteins was performed as described previously as in Hou et al. (1995, Eur. J. Haematol. 55:307-314) except that Protein L (Pierce) was used instead of Protein A to capture immune complexes. Precipitated material was electrophoresed on 4% to 12% polyacrylamide gels under nonreducing and reducing conditions and electrophoretically blotted on nitrocellulose membranes. Precipitated, biotinylated platelet membrane proteins were detected with biotinylated horseradish peroxidase-avidin complexes (ABC Staining Kit, Pierce).

Light-Chain-Library Shuffling:

To randomly pair the H44 heavy chain with a library of light chains, 10 μg plasmid DNA from clone H44L4 (a GPIIb/IIIa-specific Fab isolated from ITP patient A) was digested for 6 hours at 37° C. with SacI and XbaI (Roche Molecular Biochemicals, Indianapolis, Ind.) to remove the endogenous light-chain L4, and the heavy-chain-containing vector fragment was gel purified. A preparation of κ and γ light-chain segments from the original, unpanned ITP patient A library was obtained by digesting an equivalent amount of plasmid DNA purified from the bacterial pellet obtained during library preparation with SacI/XbaI and gel purifying the excised light chains. Vector containing heavy-chain H44 was then ligated to the library of light chains and electroporated into XL1-Blue bacteria.

Transformants were plated on carbenicillin-containing Luria-Bertani plates from which antibody clones were randomly selected, produced as soluble Fab preparations, and assayed for platelet binding by flow cytometry. Plasmid minipreparations were performed on the bacterial pellets derived from the expression experiments, and nucleotide sequencing was done to verify the presence of heavy-chain H44 and to determine the sequence of the light chain to which it randomly paired.

Exchanging Heavy and Light Chains Among Platelet-binding Clones:

Light-chain gene segments from clones H36/L76, H44/L4, and H47/L64 were freed from their respective plasmid DNAs by SacI/XbaI digestion, and the restriction products from the 3 clones (i.e., 3 heavy-chain-containing plasmids and 3 free light chains) were combined. Religation regenerated the 3 original Fabs and created 6 novel heavy-chain-light-chain pairs. After bacterial transformation, several dozen bacterial clones were randomly selected to produce Fabs for platelet-binding assays and to isolate plasmid DNA to determine heavy- and light-chain composition.

Fab Binding to Modified Staphylococcal Protein A:

Binding of Fabs to the superantigen domain of staphylococcal protein A (SpA) was measured by ELISA using SpA that had been chemically modified with iodine monochloride to destroy its native Fc-binding domain (designated mod-SpA) as in Silverman et al. (1993, Immunomethods 2:17-32.). Mod-SpA (1 μg in 50 μL) was coated on the wells of a 96-well microplate and incubated overnight at 4° C. After a rinse with distilled water, wells were blocked for 1 hour at 37° C. with PBS and 1% BSA, and Fab samples were added (50 μL/well). After a 2-hour incubation at 37° C., the wells were washed 3 times with PBS, and a mixture of alkaline phosphatase-conjugated goat antihuman κ (1:10 000) and γ (1:5000) light-chain reagents was added (Sigma Chemical). Wells were incubated at 37° C. for an additional hour, washed again with PBS, and developed with P-nitrophenyl phosphate.

Isolation of Monoclonal Human Platelet Autoantibodies:

The purpose of this study was to characterize on a genetic level the repertoires of platelet autoantibodies in chronic ITP. To isolate the repertoires, Fab/phage display technology was used to avoid the technical limitations inherent in experimental approaches that rely on B-cell immortalization to produce human monoclonal antibodies. IgG κ and γ libraries were constructed from splenic lymphocytes from 2 patients with chronic ITP and a control patient with multifactorial thrombocytopenia not due to ITP. The libraries (each comprising greater than about $2 \times 10^8$ independent transformants) were panned against intact platelets (as opposed to isolated platelet membrane GPs) to present the libraries with all possible autoantigenic determinants and to do so in a physiologically relevant manner that would preserve native antigen structure and optimize capture. By employing a magnetically activated competitive cell-surface panning strategy in which selection of platelet binders was done in the presence of an irrelevant cell type (RBCs), the capture of panreactive or nonspecific Fab-phage was prevented.

Individual Fab clones were randomly selected from platelet selected libraries and assessed for platelet binding by flow cytometry. For the 2 patients with ITP, 78 of 294 clones were positive, of which 39 were determined to be unique antibodies on the basis of the heavy- and light-chain DNA sequence. In contrast, only 1 of 77 additional clones randomly selected from the unpanned ITP libraries and none of 59 clones isolated from the control libraries (16 from the original unpanned and 43 from the platelet-selected libraries) showed platelet reactivity.

It was then assessed whether the panned ITP Fab libraries would bind to a cohort of antigens recognized by polyclonal antibodies in serum from patients with ITP. The capacity of 19 ITP serum samples to block the binding of phage displayed Fabs was assessed by flow cytometry using fluorescently labeled anti-M13 (phage) antibody relative to normal control serum samples. Fab-phage from ITP patient A was inhibited 25%±15% (range, 0%-41%) on average; that from ITP patient B was inhibited 41%±17% (range, 14%-74%). Analogous studies with serum from these patients were precluded by administration of IVIG immediately before sample collection.

Sequence Analysis of Platelet Autoantibodies:

The heavy- and light-chain nucleotide sequences from the 39 unique platelet autoantibodies were aligned with the V Base Directory of Human V Gene Segments available at the Center for Protein Engineering website at the Medical Research Council, Cambridge, UK. to examine their genetic origins and possible genetic interrelatedness. As shown in FIG. 1 (dark boxes), all heavy chains from ITP patient A (6 of 6) and all but 4 heavy chains from ITP patient B (29 of 33) used VH3-30. Usage of light-chain variable-region genes was less restricted but comprised a limited set of VL genes, including the Vκ genes A19/A3, A27, and L6.

Selective usage of a particular heavy- or light-chain gene in a cohort of antibodies may occur because of in vivo or in vitro preselection factors (e.g., greater gene usage by the pre-existing pool of B cells or cloning artifacts) or if an encounter with antigen drives clonal expansion and somatic mutation of a restricted population of B cells that use that particular gene. To address the first possibility, the diversity of the unpanned ITP patient A and patient B libraries was assessed. Analysis of the heavy and light chains of a random cohort of 43 of the 76 non-platelet-binding clones from the original libraries found no duplicate sequences and marked heterogeneity in V gene representation before selection for platelet binding (FIG. 1, patient A and B, clear boxes). Specifically, 20 different VH genes and 20 different VL genes were represented and their distribution was similar to that typically found for IgG-secreting lymphocytes in the repertoire of adults (Stollar et al., 1995, Ann. N.Y. Acad. Sci. 764:547-558). The absence of platelet reactivity of recombinant antibodies from the control library was not due to inefficient library construction or lack of VH3-30 heavy-chain representation (FIG. 1, C boxes), since 26 different VH genes and 25 different VL genes were used, including 3 antibodies encoded by VH3-30. Therefore, the highly restricted, near-total use of VH3-30 by the 39 platelet-binding ITP patient autoantibodies did not reflect a skewed representation of genes within the original pool of splenic lymphocytes, nor was it the result of a cloning artifact introduced during construction of the Fab/phage display libraries.

The possibility that the increased usage of a given V gene results from clonal expansion of restricted B-cell populations was assessed. To do this, the fact that rearranged Ig genes have extensive diversity, i.e., there is only a remote probability that 2 B cells will not only randomly select an identical combination of VH, D, and JH (for heavy chain), or VL and JL (for light chain) gene segments but will also splice the genes together to create identical junctional regions, was exploited. More specifically, alignments of the heavy- and light-chain variable-region amino acid sequences of a cohort of 39 platelet autoantibodies from ITP patients A and B were performed. Examination of the complete set of heavy-chain sequences (see FIG. 2A) demonstrated evidence of clonal expansion for a subset of B cells using VH3-30 in both patients. The members of each clone appear to have resulted from recombination of VH3-30, D1-26, and JH4b gene segments, and within each clone, they showed identical junctional regions. The fact that the CDR3 regions of clone A and clone B were quite distinct indicates that neither resulted from an interlibrary contaminant.

By examining nucleotide alignments with germline genes, ontogeny trees for the 2 putative clones were constructed to illustrate how the patterns of somatic mutation in the respective heavy chains may have evolved in vivo (FIG. 2B). For the ITP patient A clone in particular, a parsimonious mutation scheme (i.e., postulating the minimum number of mutations) was used to derive putative intermediate heavy chains (FIG. 2B, 1, 2, and 3 asterisks). The members of this clone appear to have undergone a marked degree of somatic mutation (from 4 to 21 nucleotide changes in the VH segment alone) that resulted in high replacement-to-silent (R:S) ratios, both hallmarks of an immune response characterized by antigen-driven selection (Shlomchik et al., 1987, Nature 328:805-811; and Shlomchik et al., 1990, J. Exp. Med. 171:265-292). For the ITP patient B clone, there were fewer mutations overall, but almost every mutation resulted in an amino acid replacement and clonal expansion was apparent. Therefore, the marked usage of VH3-30 in these cohorts of platelet-binding antibodies resulted at least partly from a restricted number of autoreactive B cells undergoing clonal expansion. The use of VH3-30 may also be important in conferring platelet binding because it encodes H44, a clonally unrelated heavy chain, and at least one IgM platelet autoantibody generated by conventional tissue-culture techniques as described in Kunicki et al. (1991, J. Autoimmun. 4:415-431).

H44 and the remaining heavy chains (H4, H10, H29, and H83) each had its own unique VHDJH recombination, and except for H29, somatic mutation occurred in their VH segments as well. Light chains also underwent somatic mutation (see, e.g., FIGS. 2C and 2D). Without wishing to be bound by any particular theory, some κ light chains in the cohort may be clonally related (e.g., L43, L44, and L45), but because the VLJL junction is not as diverse as the junctional regions for the heavy chain, clonal relatedness among light chains is more difficult to prove. Only a few λ light chains were present in platelet-reactive Fabs, none of which appeared to be clonally related.

Identification of Recombinant Platelet-Autoantibody Specificity:

Autoantibodies from patients with ITP often recognize complexes composed of platelet glycoproteins GPIIb/IIIa or GPIb/IX, as described in van Leeuwen et al. (1982, Blood 59:23-62), Kiefel et al. (1991, Brit. J. Haematol. 79:256-262), He et al. (1994, Blood 83:1024-1032), Hou et al. (1995, Eur. J. Haematol. 55:307-314), Olee et al. (1997, Brit. J. Haematol. 96:836-845), Kunicki et al. (1991, J. Autoimmun. 4:415-431), Woods et al. (1984, Blood 63:368-375), Woods et al. (1984, Blood 64:156-160), McMillan et al. (1987, Blood 70:1040-1045) and Gruel et al. (1995, Semin. Thromb. Hemost. 21:60-67). However, autoantibodies against other identified and unidentified antigens have been described in, e.g., He et al. (1994, Blood 83:1024-1032), Bierling et al. (1994, Brit. J. Haematol. 87:631-633), Hou et al. (1995, Eur. J. Haematol. 55:307-314), Pfueller et al. (1990, Brit. J. Haematol. 74:336-341), Sugiyama et al. (1987, Blood 69:1712-1720), Tomiyama et al. (1992, Blood 79:161-168), Deckmyn et al. (1994, Blood 84:1968-1974), Honda et al. (1990, Brit. J. Haematol 75:245-249) and Varon et al. (1990, Clin. Immunol. Immunopathol. 54:454-468).

Panning on intact platelets ensured that all relevant antigens were present during the selection process and that their native conformation was preserved. Each of the 39 unique platelet-reactive antibodies showed specificity for this cell type. None bound to Chinese hamster ovary cells, K562 cells, erythrocytes, or leukocytes on flow cytometric analysis. In addition, none showed surface, cytoplasmic, or nuclear binding to HEp-2 cells on immunofluorescence analysis and none bound to cardiolipin. However, only the antigen specificity of H44L4 could be determined with relative unambiguity. In an ELISA, H44L4 reacted with purified, immobilized GPIIb/

Figure 3A:
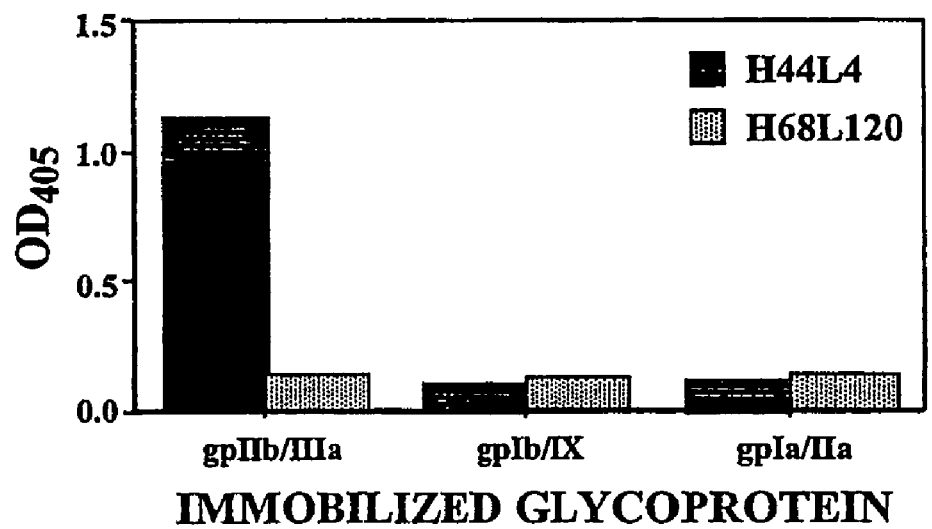
FIG. 3A depicts ELISA results for ITP patient A antibody H44L4, which was determined to be specific for platelet GPIIb/IIIa because of its binding to immobilized GPIIb/IIIa (but not to GPIb/IX or GPIa/IIa).
Figure 3B:
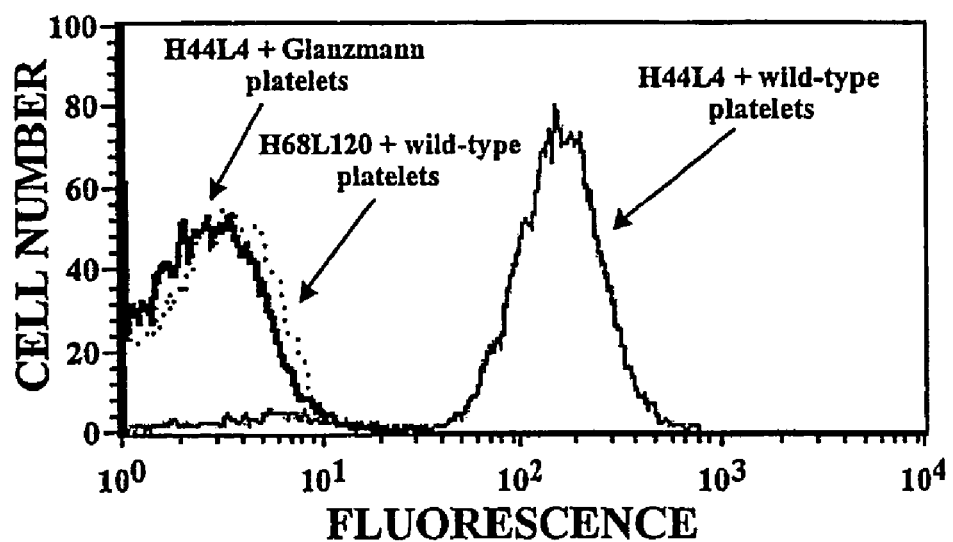
FIG. 3B depicts flow cytometry results demonstrating H44L4 binding to wild-type platelets, but not to GPIIb/IIIa deficient platelets from 3 patients with Glanzmann thrombasthenia (one of 3 examples is shown in the flow cytogram). Antibody H68L120, an anti-blood group B antibody isolated from the same original ITP patient A library (Chang et al., 2001, Transfusion 41:6-12) was used as a negative control as indicated.
Figure 4:
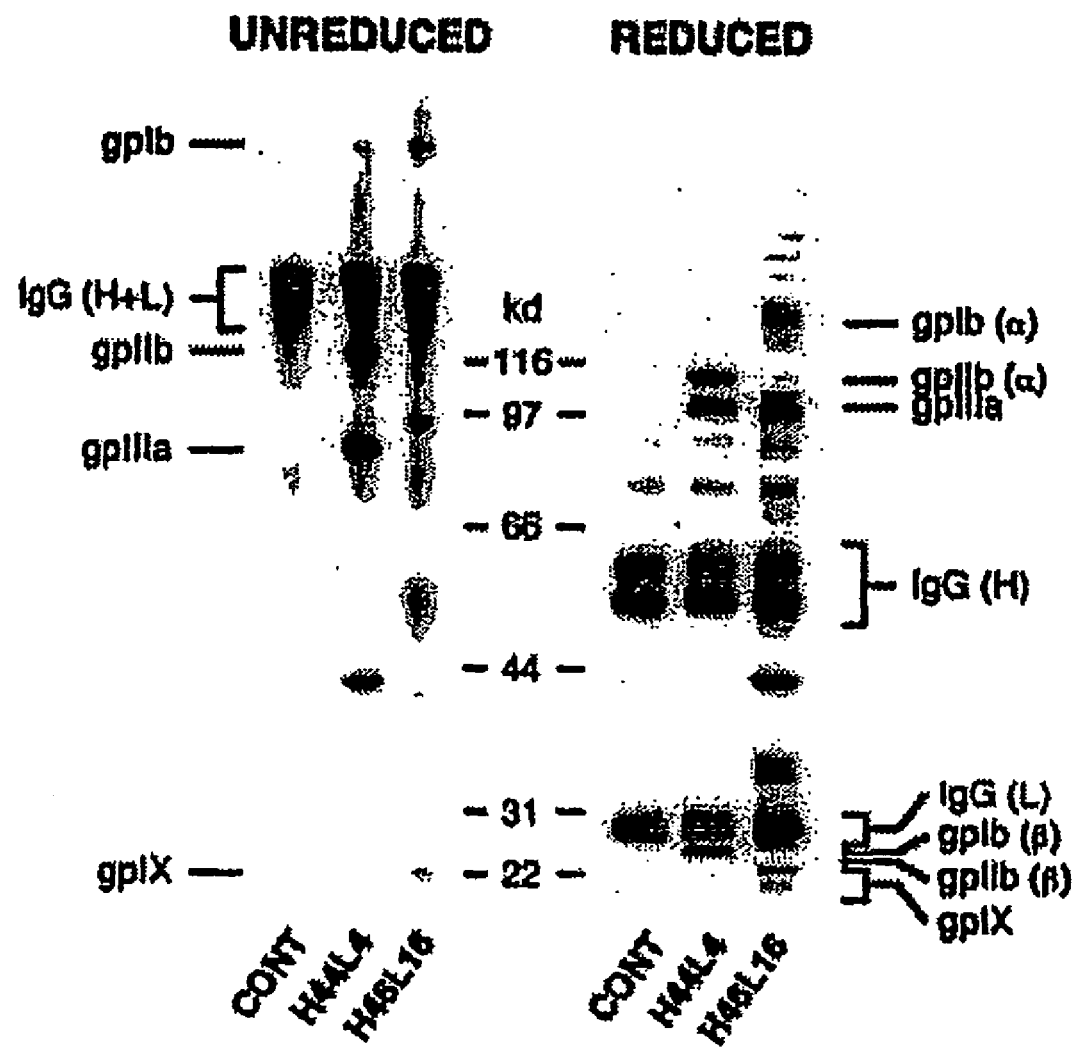
FIG. 4 is a diagram depicting determination of platelet autoantibody specificity using immunoprecipitation. Biotinylated platelets were solubilized after incubation with recombinant Fabs and antigen-Fab complexes were captured on Protein L dextran beads. Immunoprecipitated material was separated by sodium dodecyl sulfate-polyacrylamide gel electrophoresis under nonreducing (left) or reducing (right) conditions, transferred to nitrocellulose, and detected using enzyme-labeled avidin-biotin complexes. Shown in this figure are results with ITP patient A-derived antibodies H44L4 and H46L16. Note that the presence of polypeptide bands with a relative molecular weight of about 150 kD (unreduced) and about 50 kD and 25 kD (reduced) represent platelet-bound autologous IgG that was biotinylated during the platelet-labeling procedure and coprecipitated by Protein L.

IIIa but not with GPIb/IX or GPIa/IIa (FIG. 3A). H44L4 did not recognize platelets from 3 unrelated donors with type I Glanzmann thrombasthenia (FIG. 3B), whereas all other platelet-reactive Fabs bound comparably to wild-type platelets and Glanzmann platelets. Furthermore, H44L4-immunoprecipitated polypeptides migrated in accordance with the behavior of GPIIb/IIIa under reducing and nonreducing conditions (FIG. 4).

None of the other Fabs immunoprecipitated polypeptides in a manner consistent with the behavior of GPIIb/IIIa, a finding in agreement with the results of the ELISA and flow cytometry analysis using Glanzmann platelets; nor did any of them react with a stable K562 cell line expressing GPIa/IIa. However, autoantibodies H46L16, H47L64, and H48L24, 3 Fabs with clonally related heavy chains, immunoprecipitated polypeptides with molecular weights consistent with those for GPIb/IX. On ELISA, this set of Fabs did not bind significantly above background levels to purified immobilized GPIb/IX, but blocking of the relevant epitope by the mouse monoclonal capturing antibody could not be excluded. Without wishing to be bound by any particular theory, the data disclosed suggest GPIb/IX as the specificity for clone A. Neither 2 antibodies from clone B (H37L50 and H42L38) nor the 2 non-VH3-30-encoded antibodies (H4L106 and H83L34) specifically immunoprecipitated labeled protein, perhaps, and without wishing to be bound by any particular theory, because their target polypeptides were not biotinylated sufficiently or lost conformation during solubilization or because their targets are not proteins.

Contribution of the Heavy and Light Chains of H44L4 to GPIIb/IIIa Specificity:

For certain antibodies, antigen specificity is determined primarily by one or the other component chain as in Chang et al. (1991, J. Immunol. 146:176-182), Hoet et al. (1999, J. Immunol. 163:3304-3312), Ohlin et al. (1996, Mol. Immunol. 33:47-56), and Smith-Gill et al. (1987, J. Immunol. 139: 4135-4144). Identification of the platelet GPIIb/IIIa complex as the antigenic target of Fab H44L4 allowed the examination of the contribution of its constituent heavy and light chains to antigen recognition. If the VH3-30 heavy chain of H44L4 is solely responsible for GPIIb/IIIa binding, then the specific light chain that is used might be of little relevance, as long as it is permissive. Alternatively, the fine specificity of the VH3-30 heavy chain might be modified or actually determined by the paired light chain as described in Chang et al. (1998, Blood 91:3066-3078). The amenability of phage display-derived antibodies to molecular manipulation allowed the examination of this issue in detail.

The H44 heavy chain was paired with a panel of light chains and the resultant combinatorial Fabs were surveyed for their capacity to bind platelets. To do this, a new library was produced in which heavy-chain H44 was recombined with the entire light-chain repertoire from the original ITP patient A library. Only one of 101 Fabs expressing the H44 heavy chain paired with random light chains reacted with platelets. Like the original H44L4 antibody, this recombinant Fab recognized GPIIb/IIIa on ELISA. Sequence analysis confirmed that H44 was used to encode this Fab. The presence of H44 in 20 randomly selected nonreactive Fabs was also confirmed. Thus, mere usage of the H44 heavy chain alone was insufficient to confer GPIIb/IIIa reactivity on a Fab molecule. Without wishing to be bound by any particular theory, this finding suggests that specific VH-VL pairing is required to impart this binding specificity.

To examine this idea further, the light-chain gene segments of the platelet-reactive Fab were sequenced and those encoding the reference set of 20H44-expressing Fabs that lacked platelet reactivity. Interestingly, the single positive Fab (H44L125) employed an O12/O2 κ variable light-chain gene and Jκ4 J-segment gene, as did the original H44L4 Fab (FIG. 5). Indeed, light-chains L4 and L125 appear to have derived from the same B-cell clone, because they shared an especially distinctive VJ junction in which 3 nucleotides had been lost, resulting in deletion of the germline encoded proline usually found at amino acid position 95 (FIG. 5B). Because this residue lies in the CDR3 region of the light chain, deletion of 95P may confer or at least contribute to GPIIb/IIIa specificity. This is supported further by the observation that none of the 3 sampled non-platelet-reactive Fabs that use an O12/O2 light chain (FIG. 5B; clones H44L126, H44L127, and H44L128) had a deletion at position 95. These results indicate that only a limited set of light chains impart or are permissive for GPIIb/IIIa specificity when paired with a given VH3-30 gene product. Thus, the limitations in heavy- and light-chain pairings required to generate platelet-reactive Fabs was further examined. As a corollary, whether the specific light chain actually determines antigen specificity was assessed, in view of the finding that VH3-30 heavy-chain gene usage is so prevalent among platelet-reactive antibodies.

Figures 6A, 6B:
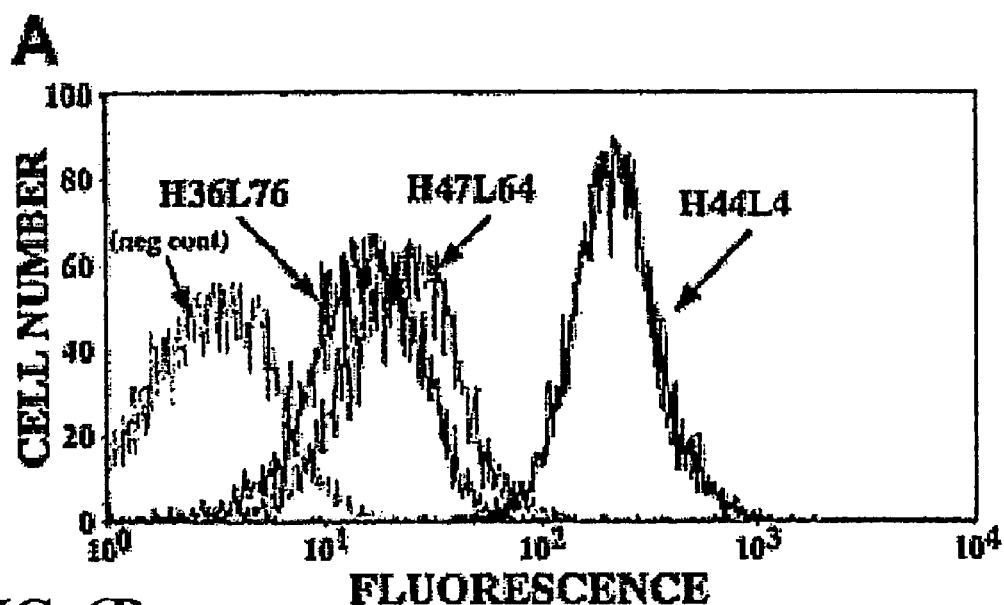
FIGS. 6A and 6B, depicts data demonstrating exchange of light chains among platelet autoantibody clones. Heavy and light chains for 3 platelet-binding clones (H44L4, H47L64, and H36L76) were interchanged to generate 9 possible combinations (6 novel and 3 reconstituted originals).

The distinctive flow cytometric (FIG. 6A) and immunoprecipitation patterns of H44L4 (a GPIIb/IIIa-specific Fab that uses Vκ-O12/O2), H47L64 (a putative GPIb/IX-specific Fab and clone A member that uses Vκ-A27), and H36L76 (a clone B member that uses Vκ-L6), each of which uses VH3-30-encoded heavy chains, was exploited. That is, by mixing their plasmid DNAs, restriction digesting each light chain away from its originally associated heavy chain, and religating the resultant admixture of heavy- and light-chain gene segments, all 9 possible combinations of the 3 heavy chains and 3 light chains were produced. Forty-three randomly selected clones, which included several examples of each combination, were assessed for platelet binding. Only the heavy- and light-chain combinations that reconstituted the 3 original Fabs bound to platelets (FIG. 6B), and their flow cytometric patterns were indistinguishable from those of the parental molecules. Thus, although VH3-30 is used frequently by autoantibodies that bind to platelets, it is not only the specific light chain but also the particular heavy- and light-chain pairing that imparts platelet reactivity and specificity.

Binding of Platelet Autoantibodies to the Superantigen Domain of SpA

The mechanism by which extracorporeal absorption of plasma from ITP patients with affinity columns containing SpA is sometimes efficacious is unknown, given that the amount of IgG removed is only about 2% of that removed during plasmapheresis (Bussel et al., 2000, In: Hematology: Basic Principles and Practice pp. 2097-2114, Churchill Livingstone, Philadelphia, Pa.; and Varnvakas et al., 1997, In: Apheresis: Principles and Practice, pp. 375-407, AABB Press, Bethesda, Md.), a treatment that is rarely effective in chronic ITP (Williams et al., 1990, In: Current Studies in Hematology and Blood Transfusion, Karger, Basel, Switzerland); and Owen et al., 1997, In: Apheresis: Principles and Practice, pp. 225-226, AABB Press, Bethesda, Md.).

Figure 7A:
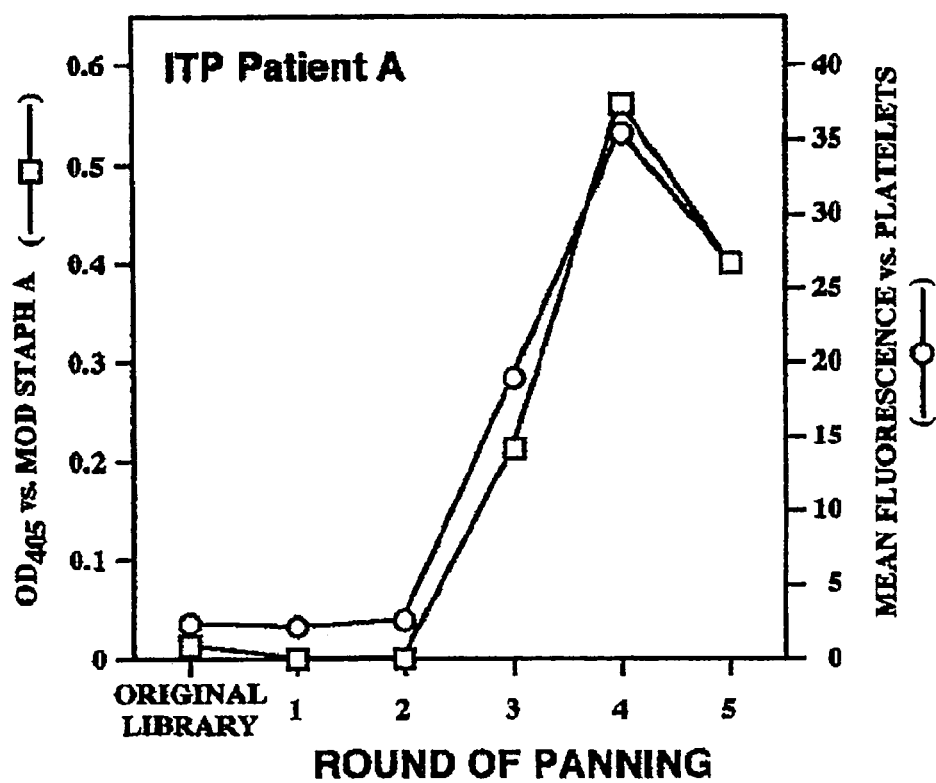
FIG. 7, comprising FIGS. 7A and 7B, demonstrates binding of platelet-selected Fabs to modified (mod), i.e., iodinated, Staphylococcal protein A (SpA). Polyclonal Fab preparations derived from the original unselected ITP patient A and patient B Fab/phage display libraries (panel A and B, respectively) and from the libraries after each round of platelet panning, were assayed for platelet binding by flow cytometry (circles, right set of axes) and for binding to mod-SpA by ELISA (squares, left set of axes).
Figure 7B:
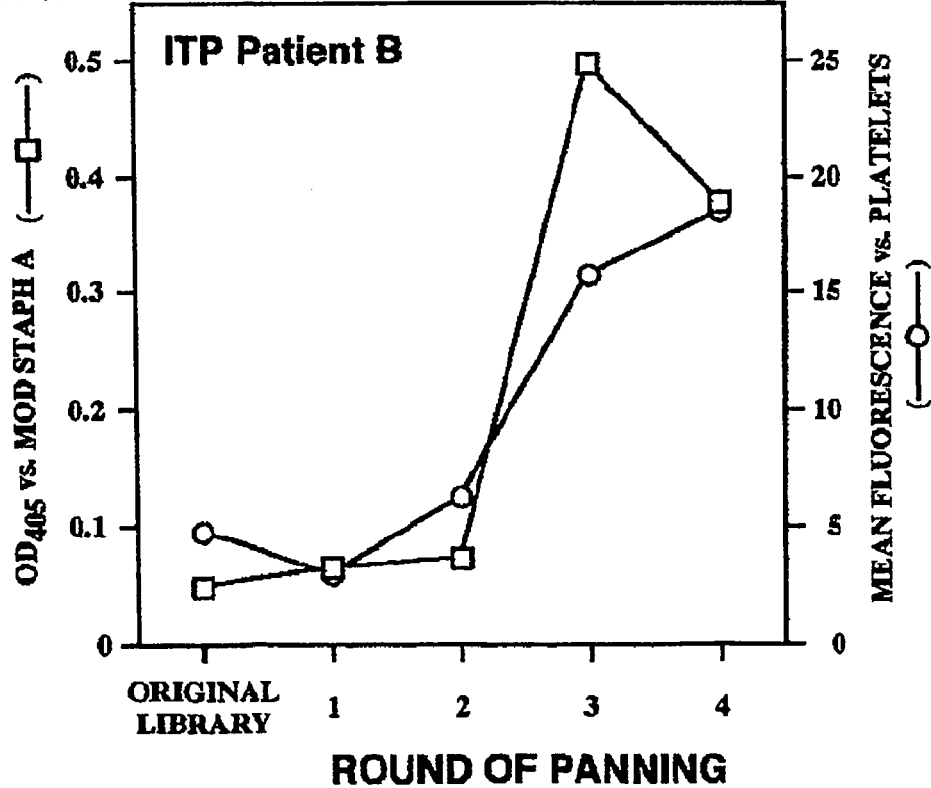

A B-cell superantigen site on SpA has been described that is independent of its well-characterized Fc binding site and that interacts with variable regions of antibodies encoded by certain members of the VH3 family, notably VH3-30 (see, e.g., Silverman, 1998, Semin. Immunol. 10:43-55; Graille et al., 2000, Proc. Natl. Acad. Sci. USA 97:5399-5404). Modification of SpA by iodination completely destroys Fc-binding activity, whereas Fab-binding activity is retained (Silverman et al., 1993, Immunomethods 2:17-32). It was assessed whether this modified SpA would bind the platelet autoantibodies disclosed elsewhere herein by virtue of their genetic restriction. The data disclosed elsewhere herein demonstrates that as platelet-binding autoantibodies were selected from polyclonal, polyspecific Fab libraries through sequential rounds of panning, there was concurrent selection for binding activity to the superantigen domain of SpA (FIG. 7).

Platelet Autoantibodies are Encoded by a Restricted Set of VH Genes

Use of the VH3-30 heavy-chain gene was found to be highly represented among platelet-reactive Fabs from both patients with ITP compared with its prevalence in the general library and despite differences in antigen specificity ($P<10^{-13}$ by Fisher exact test; FIGS. 1 and 4). Interestingly, this same heavy-chain gene was found to encode an IgM anti-GPIIb autoantibody derived by hybridoma technology from another patient with ITP (Kunicki et al., 1991, J. Autoimmun. 4:433-446; Kunicki et al., 1991, J. Autoimmun. 4:415-431), as well as several platelet-reactive, IgG phage display-derived antibodies from ITP patients selected because of their ability to bind to IVIG (e.g., Jendreyko et al., 1998, Eur. J. Immunol. 28:4236-4247; Fischer et al., 1999, Brit. J. Haematol. 105: 626-640). Without wishing to be bound by any particular theory, this marked genetic restriction to the VH3-30 heavy-chain gene for anti-platelet autoantibodies may provide an explanation for the association of ITP with seemingly unrelated disorders, such as autoimmune hemolytic anemia, SLE, chronic lymphocytic leukemia, CVID, and HIV infection, in which VH3-30 and related gene products are expanded or involved in disease pathogenesis (see, e.g., Efremov et al., 1996, Blood 87:3869-3876; Efremov et al., 1997, Ann. N.Y. Acad. Sci. 815:443-447; Roben et al., 1996, J. Clin. Invest. 98:2827-2837; Braun et al., 1992, J. Clin. Invest. 89:1395-1402; Berberian et al., 1993, Science 261:1588-1591; Wisnewski et al., 1996, J. Acquir. Immune. Defic. Syndr. Hum. Retrovirol. 11:31-38; and Bettaieb et al., 1996, Clin. Exp. Immunol. 103:19-23).

Why use of the VH3-30 heavy chain is overrepresented among antibodies that show platelet reactivity is a pivotal question. One possibility is that antibodies encoded by most other VH gene products are less able to bind to platelets. Such a restriction on antigen recognition could explain why no VH3-23 heavy-chain gene product was identified among platelet-reactive Fabs, even though it is the most frequently used VH gene in the repertoire (Brezinschek et al., 1995, J. Immunol. 155:190-202; Brezinschek et al., 1997, J. Clin. Invest. 99:2488-2501; Kraj et al., 1997, J. Immunol. 158: 5824-5832; Suzuki et al., 1995, J. Immunol. 154:3902-3911; and Huang et al., 1996, Mol. Immunol. 33:553-560). However, several antibodies in the cohort of platelet binders were encoded by VH genes other than VH3-30, including VH1-$O_2$, VH1-46, VH3-21, and VH4-59 (FIG. 1 and FIGS. 2A-2D). Remarkably, this identical group of VH genes was found by Boucher et al. (1997, Blood 89:3277-3286) to encode all but one antibody in a large number of human anti-Rh(D) RBC alloantibodies. As noted by these investigators, products of these germline genes are among the most cationic in the human VH repertoire.

Without wishing to be bound by any particular theory, the resulting constitutive net positive charge may allow the antibodies to effectively permeate the highly negative RBC ζ potential, thus permitting contact with antigen (Mollison et al., 1997, In: Blood Transfusion in Clinical Medicine, Blackwell Scientific Publications, Oxford, United Kingdom). Because platelets have an even greater density of cell-surface negative charges as a result of their thick glycocalyx rich in acidic mucopolysaccharides (White, 1971, In: The Circulating Platelet, pp. 4445, Academic Press, New York, N.Y.; and Seaman et al., 1967, In: Platelets: Their Role in Haemostasis and Thrombosis, pp. 53-68, Schattauer-Verlag, Struttgart, Germany), platelet-surface charge may play a similar role in biasing the use of cationic germline VH segments. Therefore, use of cationic VH genes may facilitate access to the membrane surface, but specificity for a particular antigen may be determined by heavy-chain CDR3 and light chain.

The data disclosed herein demonstrate that this role for light chain was examined by pairing the VH3-30-encoded H44 heavy-chain product found in the platelet GPIIb/IIIa-specific Fab with all members of the entire light-chain repertoire from the same library (approximately $10^8$ light chains). Only one other platelet-reactive, GPIIb/IIIa-specific Fab was retrieved (FIG. 5). Remarkably, the light chain in this Fab was not only very similar in sequence to the light chain found in the original antibody, but it appeared, on the basis of CDR3 analysis, to have derived from the same B-cell clone in vivo. Furthermore, light chains from platelet-reactive Fabs that use VH3-30 heavy-chain genes were not interchangeable. Indeed, when the genes from a set of platelet-reactive Fabs with differing specificity were permitted to recombine randomly, only the original combinations of heavy and light chains led to detectable platelet binding (FIG. 6). These observations suggest that platelet antigen specificity cannot result from simple pairing of an array of permissive heavy- and light-chain gene products, but requires precise interactions between particular heavy chains and their light-chain companions.

Role of Autoantigen and Clonal Expansion in Chronic ITP

The study of human autoimmune disease is greatly facilitated by focusing on disorders such as ITP, in which it is clear that the associated autoantibodies are unequivocally involved in pathogenesis. However, the role played by self-antigens in the evolution of autoreactive antibodies and the clonality of the autoimmune response are not well understood. On the basis of light-chain restriction, previous reports suggested that platelet autoantibodies in chronic ITP are clonally restricted (van der Harst et al., 1990, Blood 76:2321-2326; Christie et al., 1993, Brit. J. Haematol. 85:277-284; Stockelberg et al., 1995, Brit. J. Haematol. 90:175-179; Stockelberg et al., 1996, Ann. Hematol. 72:29-34; and McMillan et al., 2001, Thromb. Haemost. 85:821-823).

Figure 2A:
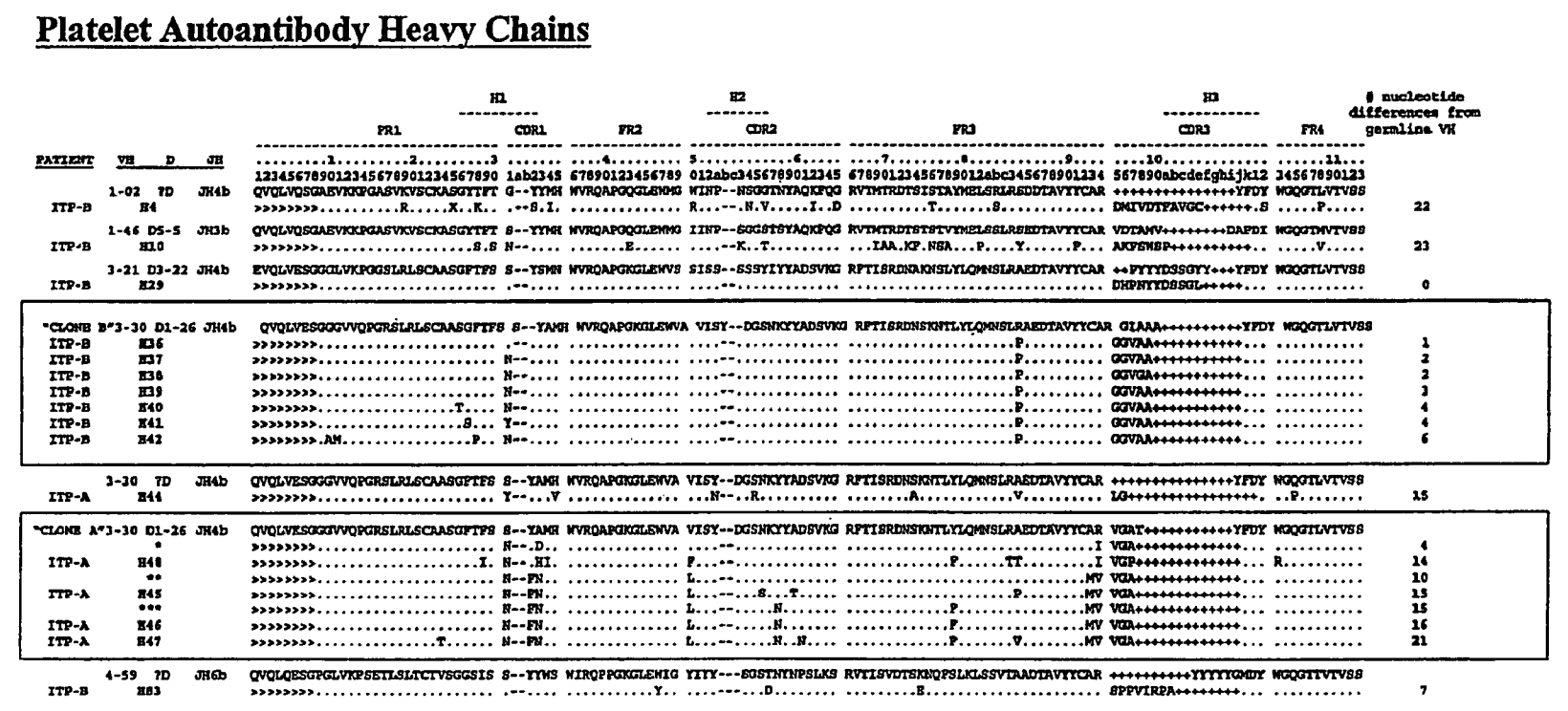
Figure 2C:
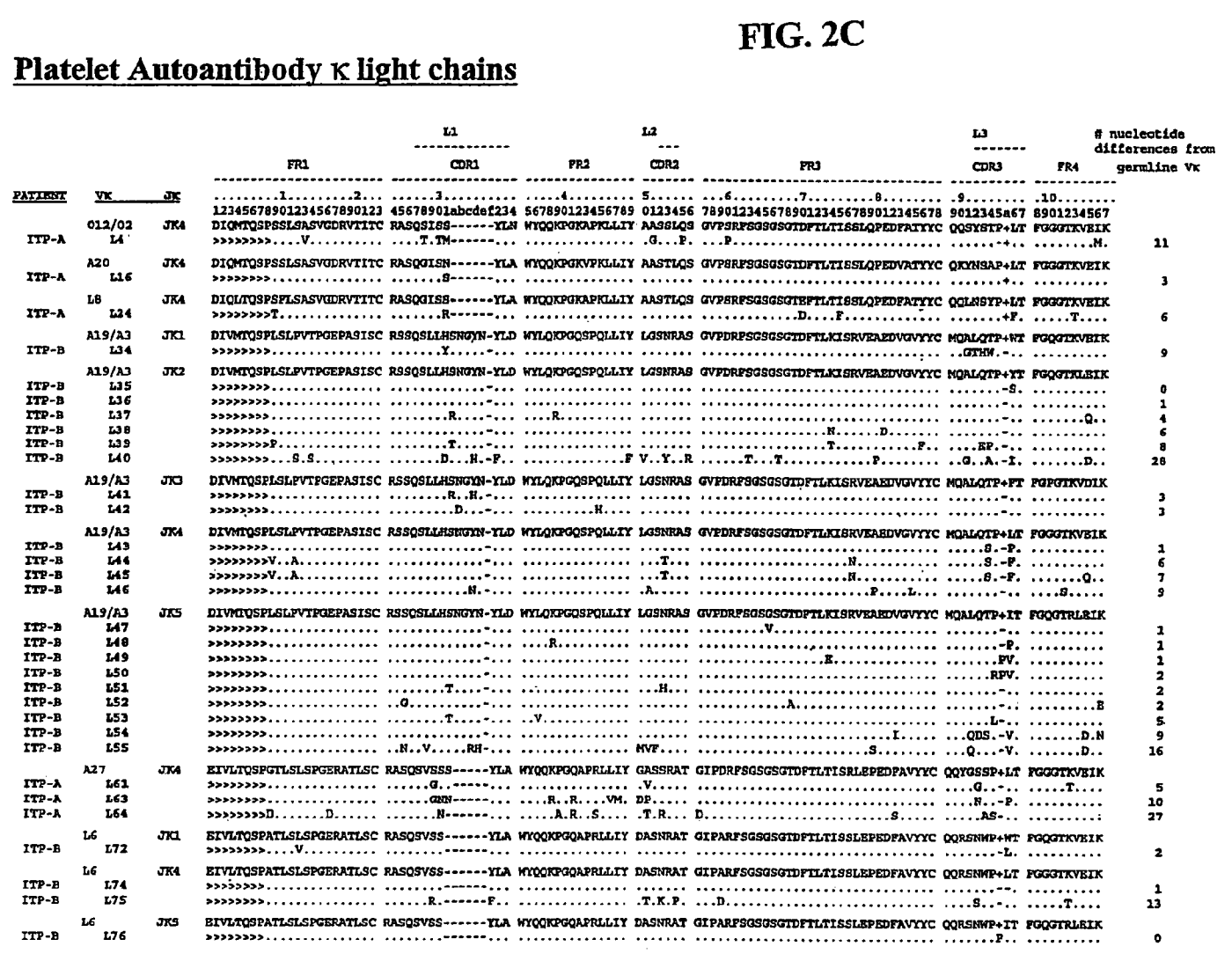

Several features of the platelet-reactive autoantibodies disclosed for the first time elsewhere herein indicate that they arose as part of an antigen-driven clonal expansion, rather than being the result of polyclonal B-cell activation triggered by nonspecific stimuli. First, most antibodies isolated from each patient shared a single heavy chain VHDJH rearrangement indicating their derivation from a single B cell (FIG. 2B). Second, somatic mutation with high R:S ratios was evident in heavy- and light-chain variable regions (FIGS. 2A-2D). Third, each of the platelet-reactive Fabs was derived from an IgG library, indicating that isotype switching had occurred, another hallmark of a T-cell-dependent, antigen-driven immune response. Finally, the requirement for precise heavy- and light-chain pairing to generate antigen specificity (FIGS. 5 and 6) also typifies antigen-driven immune responses (see, e.g., Hoet et al., 1999, J. Immunol. 163:3304-3312; Ohlin et al., 1996, Mol. Immunol. 33:47-56; Near et al., 1990, Mol. Immunol. 27:901-909; and Czerwinski et al., 1998, J. Immunol. 160:4406-4417).

Without wishing to be bound by any particular theory, it may be these characteristics that distinguish pathogenic antiplatelet autoantibodies from "benign" ones cloned from samples from unaffected donors. Such naturally occurring platelet-binding antibodies, in contradistinction to those disclosed elsewhere herein, are nearly always IgM, are often polyreactive, have little or no somatic mutation of their variable regions, or show a combination of these characteristics as described in Denomme et al. (1992, Brit. J. Haematol. 81:99-106), Denomme et al. (1994, J. Autoimmun. 7:521-535), and Escher et al. (1998, Brit. J. Haematol. 102:820-828). These differences are analogous to those used to distinguish pathogenic from benign autoantibodies in murine models of autoimmunity as described in Shlomchik et al. (1987, Nature 328:805-811) and Kunicki et al. (1991, J. Autoimmun. 4:415-431). Whether the B cells that produce benign anti-platelet autoantibodies are the clones that go on to lose self-tolerance, switch isotypes, somatically mutate their variable-region genes, and secrete pathogenic autoantibodies is not clear. In fact, it may be this clonally unrelated pool of natural, non-pathologic anti-platelet autoantibodies that normally functions to keep production of pathologic autoantibodies in check through a mechanism of competitive tolerance, as has been proposed for murine rheumatoid factors as in Stewart et al. (1997, J. Immunol. 159:1728-1738).

Clinical and Therapeutic Implications of VH Gene Restriction

Current treatments for chronic ITP are characterized by relatively nonspecific immune intervention. If restriction of platelet autoantibodies to the VH3-30 heavy-chain gene is confirmed by studies of additional immune repertoires, exploitation of this restriction can facilitate the design of more targeted forms of immunotherapy. For example, it is known that SpA has a B-cell superantigen site-distinct from its well-characterized Fc-binding domain—that is specific for the gene products of certain VH3-encoded Igs, notably VH3-30 (Silverman, 1998, Semin. Immunol. 10:43-55; and Graille et al., 2000, Proc. Natl. Acad. Sci. USA 97:5399-5404). Consistent with this activity, the data disclosed elsewhere herein demonstrate that panning of ITP patient A and B phage display libraries on platelets resulted in concomitant enrichment for both platelet and mod-SpA binders (FIG. 7). In studies in mice, targeted deletion of VH3-30 homologs by apoptotic cell death occurred on in vivo administration of recombinant mod-SpA superantigen (e.g., Silverman et al., 2000, J. Exp. Med. 192:87-98; and Goodyear et al., 2001, Arthritis Rheum. 44:S296), suggesting that infusion of small amounts of mod-SpA might likewise downregulate production of platelet autoantibodies in ITP. In this regard, and in light of recent studies demonstrating shedding of up to 200 μg SpA from SpA-silica columns during extracorporeal immunoabsorption procedures as described (Sasso et al., 2000, Arthritis Rheum. 43:1344), the long-term remissions may be a consequence of infused SpA and not the removal of antibody by the columns per se. Future studies testing the therapeutic effectiveness of this or other VH3-30-targeted reagents, such as anti-idiotypic antibodies derived from mice (Crowley et al., 1990, Mol. Immunol. 27:87-94; and Shokri et al., 1991, J. Immunol. 146:936-940) or humans (Fischer et al., 1999, Brit. J. Haematol. 105:626-640), may provide novel approaches for regulating immune-repertoire composition. Furthermore, development of reagents for rapid identification of the genetic origins of platelet autoantibodies can help predict responsiveness to such novel molecular therapies in individual patients.

Example 2

Peptide Inhibitors of a Human GPIIb/IIIa-Specific Platelet Autoantibody (H44L4)

Peptide phage display was used to define the epitope on platelet glycoprotein (GP)IIb/IIIa to which the human anti-GPIIb/IIIa monoclonal anti-platelet autoantibody termed "H44L4", disclosed elsewhere herein, binds. Small molecule "peptidomimetics", such as those which can be derived using peptide phage display technology, can assume the structure of conformational epitopes which would not only help map where on GPIIb/IIIa H44L4 binds, but can serve as leads for the development of infusible drugs that can inhibit the binding of such platelet autoantibodies in vivo.

Two different commercially-available peptide display libraries (commercially available from New England Biolabs, Beverly, Mass.) were used. These libraries, i.e., a "12-mer" linear peptide library and a "Cysteine-7-mer-Cysteine" (C7C) constrained peptide library, were used in sets of experiments in which H44L4 was the target. To aid in the panning protocol, antibody H44L4 was first converted from its current form as a Fab fragment (as isolated from the antibody phage display experiments described previously elsewhere herein and in Roark et al., 2002, Blood 100:1388-1398, incorporated by reference in its entirety herein) to a full-length IgG using the PIGG vector (Scripps Institute) as described in Rader et al., 2002 FASEB J., 16:2000-2002.

The panning experiments were conducted per the manufacturer's instructions provided with the display libraries (New England Biolabs). Briefly, H44L4 was incubated in solution with one of the peptide libraries, then antibody with bound phage was captured using Protein A-conjugated magnetic beads. Following washing steps, bound phage was eluted with acid and introduced into fresh E. coli cultures for propagation. A second round of panning was likewise performed except antibody and bound phage were captured with Protein G-conjugated magnetic beads. The purpose of alternating Protein A and Protein G was to avoid capture of phage-displayed peptides specific to either Protein A or G. Therefore, a third round of panning was performed with Protein A capture; a fourth round with Protein G.

Figure 8:
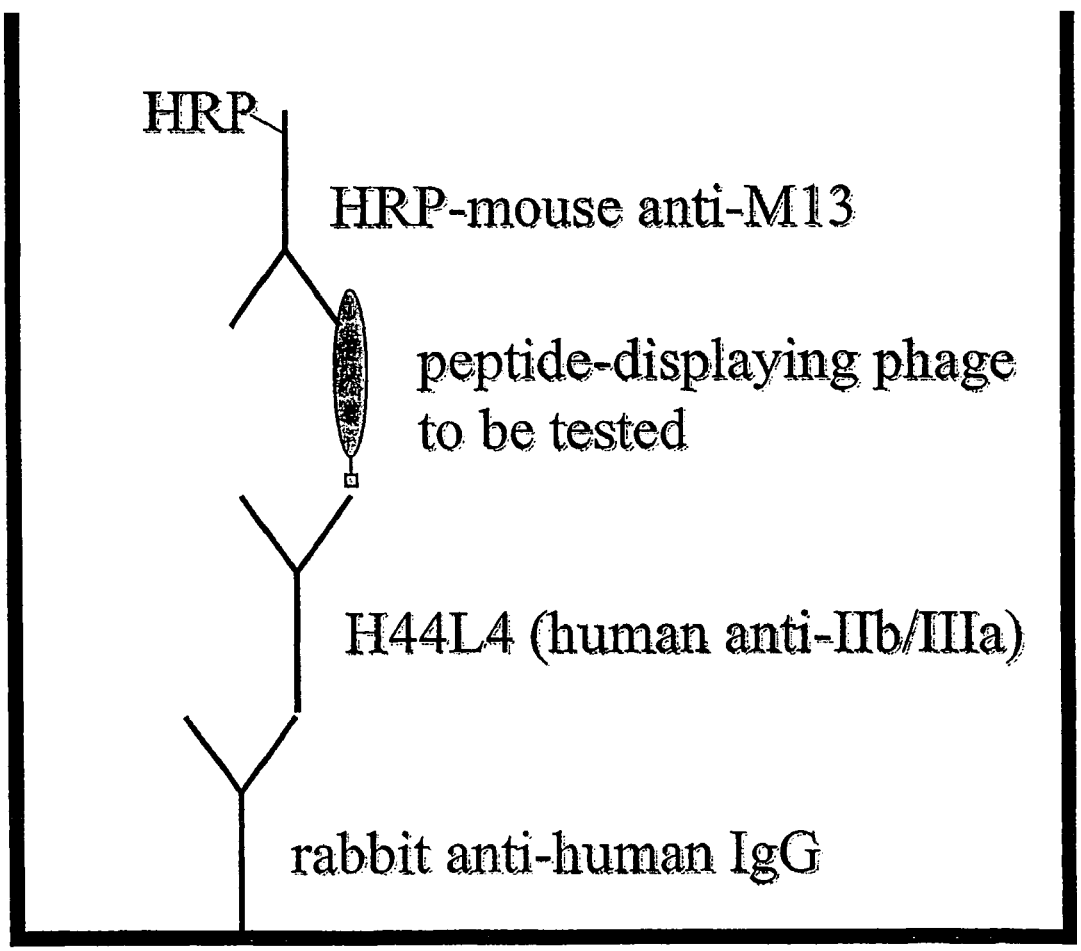
FIG. 8 is a schematic illustration of the ELISA scheme used to test the binding of peptidomimetics, such as those which can be derived using peptide phage display technology, to H44L4.
Figure 9A:
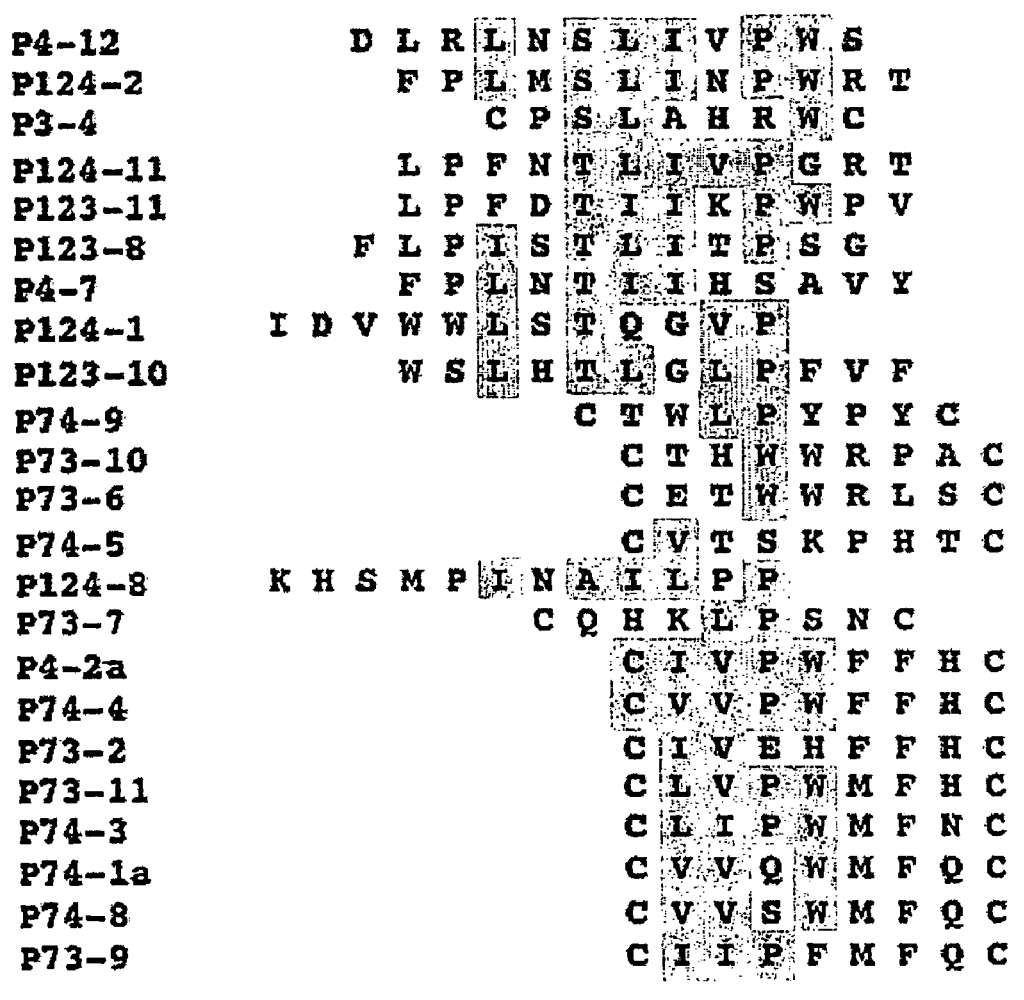

From both the 12-mer linear library and C7C constrained library, sets of related peptides were obtained that bound to H44L4 (FIG. 9), but not to any number of other control antibodies (e.g., an anti-red cell Rh antibody) using an ELISA scheme depicted in FIG. 8. The amino acid sequences of the peptides identified that bound with an anti-platelet autoantibody are set forth in FIG. 9A. Additionally, the nucleotide sequences of the nucleic acids encoding these peptides are set forth in FIG. 9B.

Figure 10:
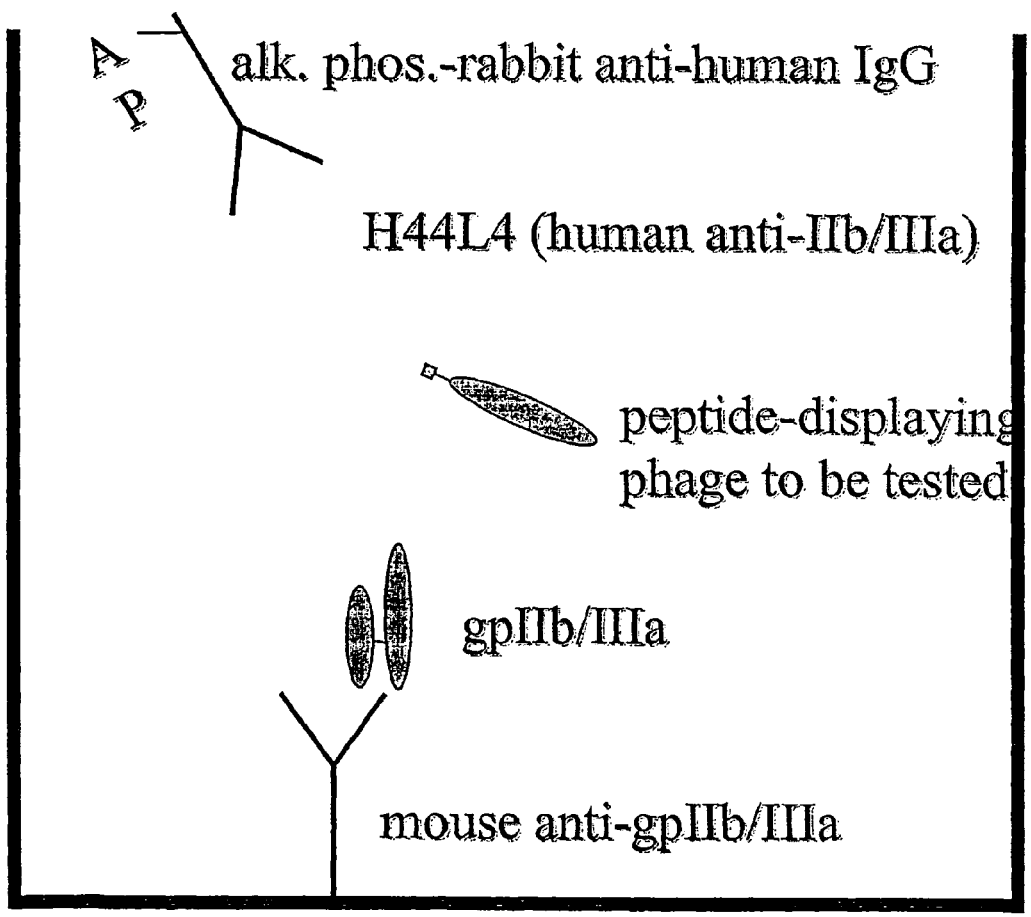
FIG. 10 depicts a schematic depiction of the ELISA scheme used to assay the activity of the peptidomimetics to inhibit H44L4 from binding to purified GPIIb/IIIa.
Figure 11:
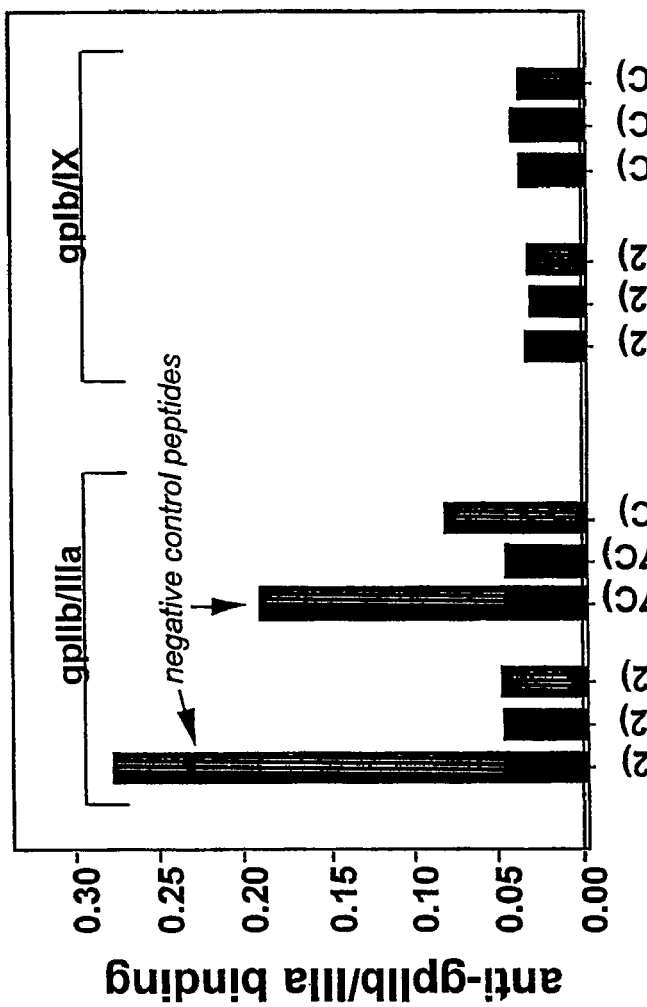
FIG. 11 depicts a graph depicting inhibition of anti-GPIIb/IIIa binding to GPIIb/IIIa by peptidomimetics.

Next, it was assessed whether the peptides actually block the binding of autoantibody H44L4 to GPIIb/IIIa. Two of the 12-mer peptides (P4-12 and P4-7) and two of the constrained 7-mer peptides (P3-4 and P4-2a), as well as several of non-binding 12-mer library and constrained 7-mer library peptides (P01 and P01-1) used as negative controls, were examined. The data disclosed herein demonstrate that P4-12, P4-7, P3-4, and P4-2a, but not the control peptides, specifically blocked the binding of autoanti-GPIIb/IIIa to purified GPIIb/IIIa by ELISA (FIG. 11), where FIG. 10 depicts the design of the ELISA assay employed. The data disclosed herein further demonstrate the specificity of H44L4 to GPIIb/IIIa as there was no detectable binding to GPIb/IX, another common platelet autoantigen often targeted by ITP autoantibodies (FIG. 11).

Figure 12:
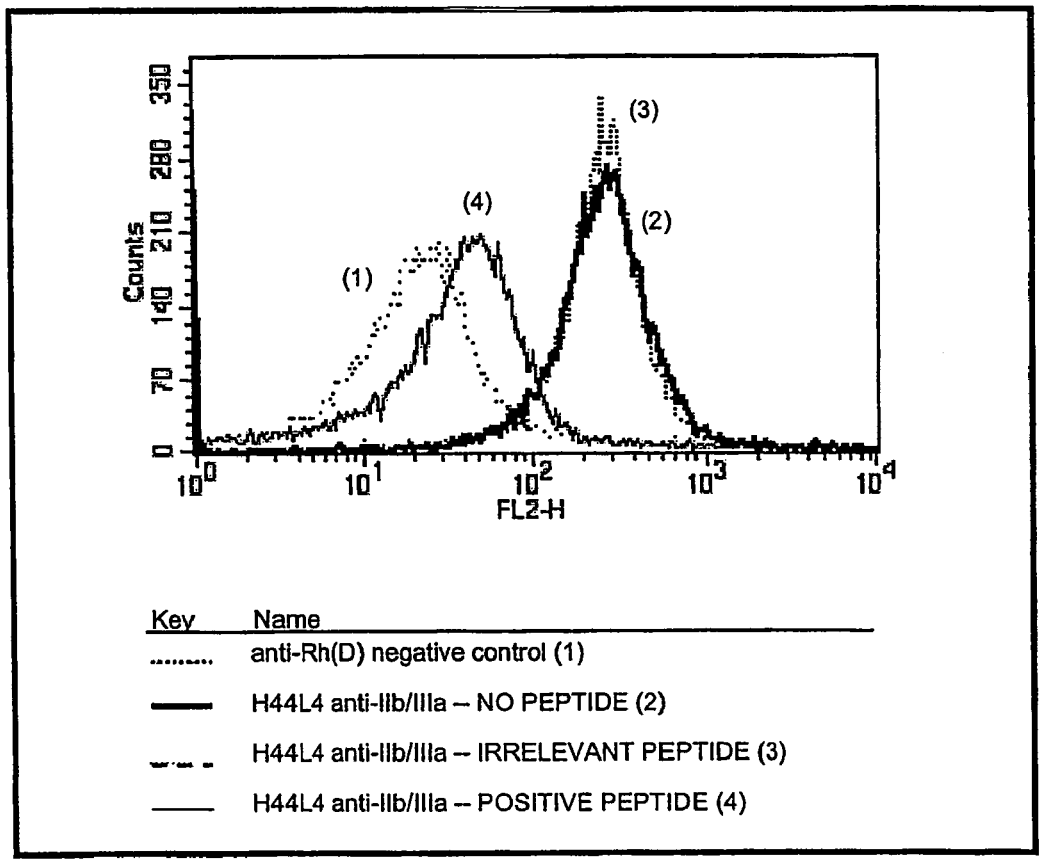
FIG. 12 depicts a graph showing inhibition of binding of H44L4 to intact platelets by the peptidomimetics as assessed by flow cytometry.
Figure 13A:
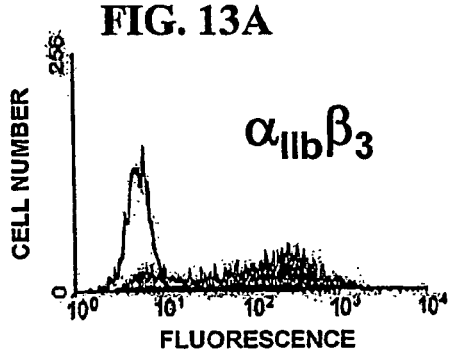
FIGS. 13A through 13F, depicts flow cytograms demonstrating the epitope mapping of the binding of H44L4 to platelet GPIIb/IIIa, as assessed by flow cytometry. H44L4 was incubated with a set of Chinese hamster ovary (CHO) cells expressing either $\alpha_{IIb}\beta_3$ or $(\alpha_{IIb}-\alpha_v)\beta_3$ chimeras in which a segment of $\alpha_{IIb}$ (either amino acids 1-459, 1-223, 223-459, or 447-1009 as indicated in each panel depicted herein, based on the amino acid sequence set forth in GenBank Accession No. P08514; SEQ ID NO: 153) was substituted for that portion of $\alpha_v$ ($\alpha_v\beta_3$, another integrin, also referred to as the vitronectin receptor). These experiments were performed using the cell lines and methods described by McMillan et al. (2002, Brit J of Haematol, 118:1132-1136), where the shaded and unshaded histograms represent incubation with transfected or untransfected CHO cells, respectively. The data show that H44L4 did not bind to any of the cell lines expressing chimeras comprising the N-terminal portion of $\alpha_{IIb}$ but required amino acids 447-1009 of $\alpha_{IIb}$ to bind. In addition, the data show that H44L4 did not bind to the vitronectin receptor ($\alpha_v\beta_3$), an integrin to which ReoPrO™ (infliximab), a chimeric human/murine anti-$\alpha_{IIb}\beta_3$, also binds.
Figure 13B:
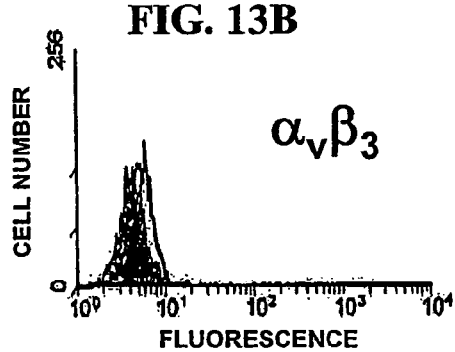
Figure 13C:
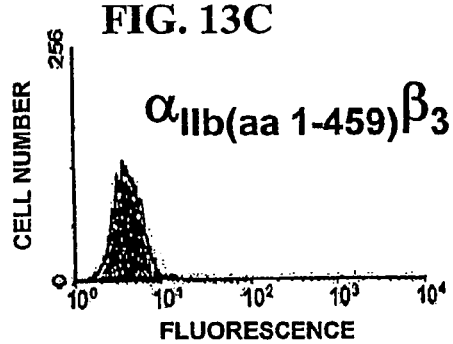
Figure 13D:
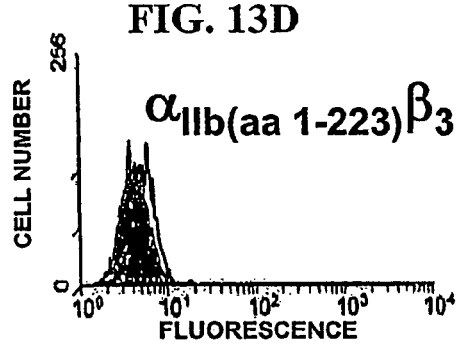
Figure 13E:
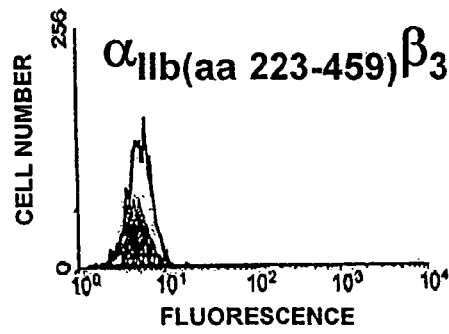
Figure 13F:
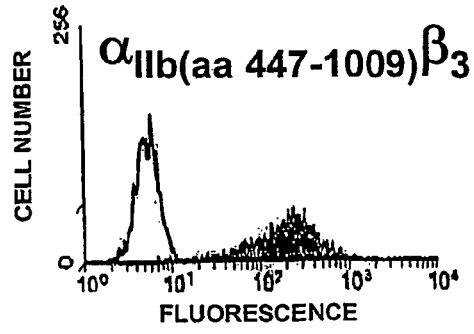

The ability of these peptides to likewise block the binding of H44L4 to intact platelets, as assessed by flow cytometry, was also assessed. The data disclosed herein demonstrate that H44L4 binds strongly to platelets in the absence of any peptide (FIG. 12, curve 2) or in the presence of an irrelevant peptide P01-12 (FIG. 12, curve 3), but bound significantly less when small amounts of phage-displayed peptide P4-12 were present (FIG. 12, curve 4).

Without wishing to be bound by any particular theory, the significance and potential utility of these inhibitory peptides are two-fold. First, if they inhibit anti-GPIIb/IIIa autoantibodies in the sera of other ITP patients, then the peptides are potential leads for the development of drugs that can block autoantibody binding in vivo and thus serve as a potential treatment for ITP.

The data disclosed elsewhere herein, i.e., epitope mapping studies, infra, suggest that H441A is a fairly unique anti-GPIIb/IIa antibody in terms of where it binds on GPIIb/IIIa and the fact that its binding to platelets appears to inhibit their function. These data suggest a novel therapeutic modality whereby, using H44L4 as a Fab fragment (i.e., without its Fc domain that could interact with splenic macrophages), H44L4 can serve as a therapeutically-useful platelet antagonist drug which, unlike prior art products such as, but not limited to, ReoPro™ ((infliximab; abciximab; Centocor Corp.), is full human and does not have other potential side effects. Further, the data disclosed herein demonstrate that yet another potential utility for the peptides disclosed herein is as "antidotes" to H44L4 when platelet function needs to be restored. That is, administration of the peptides, thereby inhibiting the binding of H44L4 with GPIIb/IIIa, would inhibit the ability of H44L4 to inhibit platelet aggregation. This provides a novel therapeutic for use where inhibition of platelet aggregation is desired, but where reversal of the inhibition is desired before the antibody, and/or its effect, has been cleared from an animal.

Example 3

Epitope Mapping Studies

To assess where H44L4 binds on the platelet GPIIb/IIIa molecule (GPIIb/IIIa, an integrin molecule, is also referred to as $\alpha_{IIb}\beta_3$), H44L4 was incubated with a set of Chinese hamster ovary (CHO) cells expressing either $\alpha_{IIb}\beta_3$ or $\alpha_{IIb}$-$\alpha_v\beta_3$ chimeras in which a segment of $\alpha_{IIb}$ (either amino acids 1-459, 1-223, 223-459, or amino acids 447-1009) was substituted for that portion of $\alpha_v$ ($\alpha_v\beta_3$ is also a member of the integrin family and is known as the "vitronectin receptor"). These epitope mapping assays, and the chimeras, were described previously by McMillan et al. (2000, Brit. J. Haematol. 118:1132-1136). In those studies, McMillan et al., tested polyclonal patient sera or platelet eluates (H44L4 is the first human monoclonal autoantibody to platelets ever identified). McMillan et al., suggest that nearly all of the patient-derived polyclonal antibody material required the N-terminal portion of $\alpha_{IIb}$ to bind.

For purposes of the epitope-mapping studies disclosed herein, the amino acid residues indicated are based on the amino acid sequence of $\alpha_{IIb}$ as disclosed in GenBank Accession No. P08514 (also referred to as integrin alpha-IIb precursor, platelet membrane glycoprotein IIb, GPalpha IIb, GPIIb, and CD41 antigen; SEQ ID NO:153).

Surprisingly, H44L4 did not bind to any of the chimeras expressing this N-terminal portion of $\alpha_{IIb}$; instead, H44L4 required amino acids 447-1009 of $\alpha_{IIb}$ to bind (FIG. 13, especially demonstrating that unshaded curves represent negative controls in which H44L4 was run against untransfected CHO cells). The data disclosed herein also demonstrate the novel finding that H44L4 did not bind to the vitronectin receptor ($\alpha_v\beta_3$) to which ReoPro™ binds. ReoPro also is known to bind to the N-terminal portion of $\alpha_{IIb}$ in the fibrinogen binding region, apparently unlike H44L4. Thus, H44L4 is an novel antibody that binds with GPIIb/IIIa, in a manner which is surprising based on previous studies.

Example 4

Effect of H44L4 on Platelet Function

The bleeding that is seen in ITP patients is generally attributed to a quantitative deficiency of platelets, i.e., the antiplatelet autoantibodies bind to a patient's platelets and cause them to be removed by phagocytosis by splenic macrophages. However, it has also been believed that some of the bleeding that can occur may be due to qualitative deficiencies, i.e., that the binding of platelet autoantibodies to platelets may interfere with their function and may affect whether or not the antibodies also induce platelet removal and destruction in the spleen.

The ability to clone such ITP-associated antibodies, as demonstrated for the first time herein, not only provides an endless source of material for studying the immunobiology of their effects on platelet function, but also provides a potentially clinically-useful drug that can be used to prevent unwanted platelet clotting, such as for the indications of the drug ReoPro™. By expressing the antibody (drug) as a Fab fragment (like ReoPro), the Fc-dependent binding of antibody-coated platelets to splenic macrophages can be avoided, thereby sparing platelet numbers, while preserving platelet functional inhibition. Given the apparent differences in binding properties between H44L4 and ReoPro™ (see epitope mapping results demonstrating that ReoPrO™ binds to the ligand binding region of GPIIb/IIIa, within residues 1-459 whereas H44L4 requires residues from about 447 to about 1009 to be present in the molecule, based on the amino acid sequence described in GenBank Accession No. P08514, which is also referred to as integrin alpha-IIb precursor, platelet membrane glycoprotein IIb, GPalpha IIb, GPIIb, and CD41 antigen (SEQ ID NO: 153), if H44L4 inhibited platelet function it may do so in a markedly different way, i.e., not by directly competing for fibrinogen binding to the N-terminal portion of activated GPIIb/IIIa.

To assess whether H44L4 inhibits platelet function, platelet aggregometry studies were performed according to the method of Born (1962, Nature 194:927-929). Briefly, fresh platelet-rich plasma was mixed with H44L4, with E1M2 (an irrelevant human anti-red blood cell Rh(D) monoclonal antibody), or with no antibody (control), and the plasma was incubated for 5 minutes at 37° C. (final antibody concentration, 50 µg/ml). Platelet suspensions were placed in the cuvette of an aggregometer, and ADP was added to a final concentration of 5 µM to induce platelet aggregation.

Figure 14:
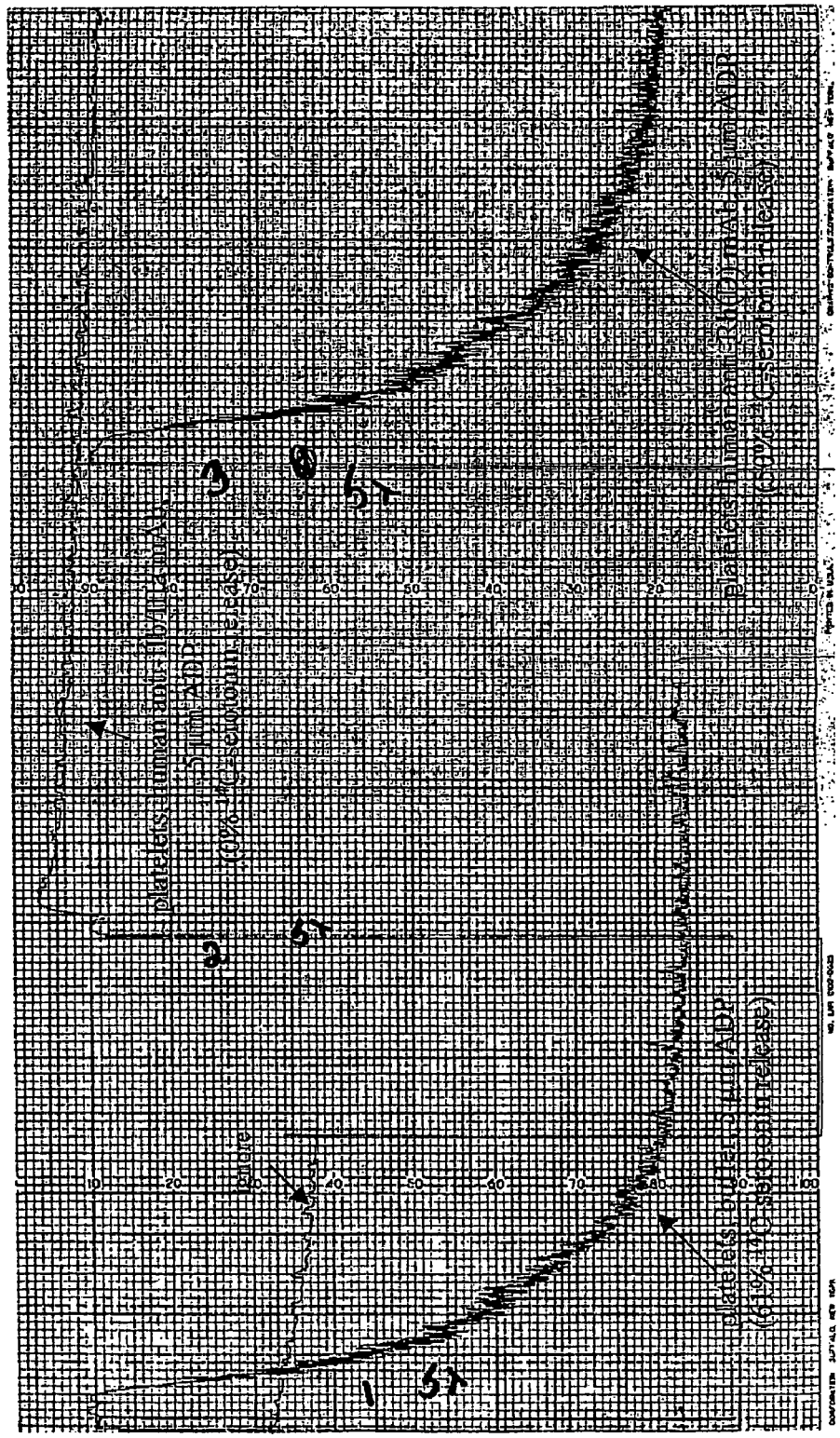
FIG. 14 depicts a graph showing the effect of H44L4 on platelet function. The data depicted demonstrate that H44L4 inhibited ADP-stimulated platelet aggregation, whereas an irrelevant human monoclonal antibody had no effects. In addition, H44L4 inhibited the release of serotonin, a hallmark of platelet activation, from intracellular stores.

The data disclosed herein demonstrate that H44L4 totally inhibited detectable platelet aggregation, whereas an irrelevant human monoclonal antibody had no effect (FIG. 14). Furthermore, since the platelets were preloaded with $^{14}$C-serotonin, measurement of serotonin release from intracellular platelet granules could be measured. The data disclosed herein (e.g., FIG. 14) demonstrate that H44L4 totally inhibited the release of serotonin, a hallmark of platelet activation, from intracellular stores.

Example 5

Inhibition of Fibrinogen Binding by H44L4

Upon platelet activation, GPIIb/IIIa (also referred to as $\alpha_{IIb}\beta_3$) goes from a low affinity state for the binding of fibrinogen to a high affinity state. The binding of fibrinogen then mediates platelet aggregation. Interfering with this process has been an approach used for developing platelet antagonists, e.g., the humanized murine monoclonal antibody ReoPro™ does this by competing with fibrinogen for the binding to GPIIb/IIIa. This competition is facilitated by the antibody having fibrinogen's important RGD sequence in its variable region.

Figure 15:
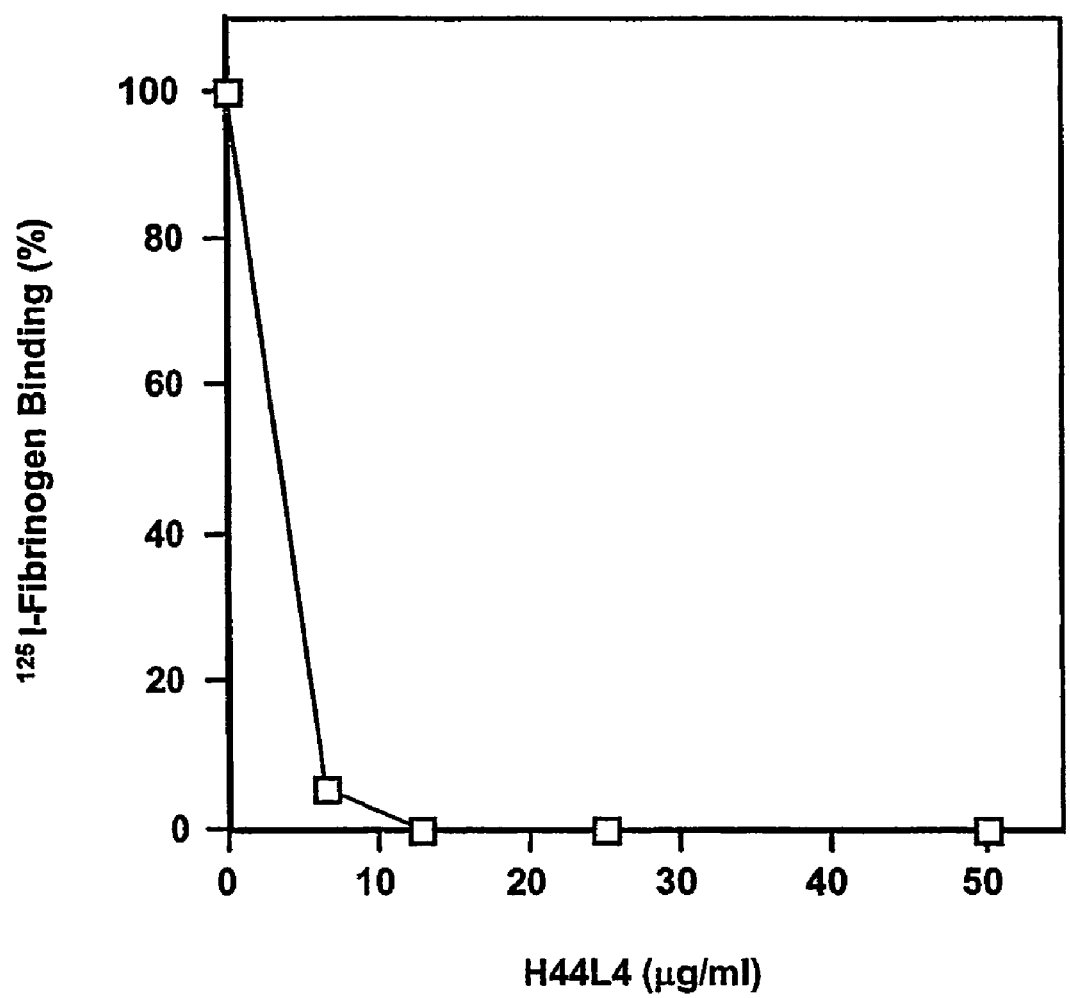
FIG. 15 depicts a dose response curve utilizing various concentrations of H44L4 with ADP-stimulated platelets and $^{125}$I-fibrinogen. At the lowest concentration of H44L4 tested, fibrinogen binding was reduced to only 5.4% of the control amount obtained in the absence of H44L4. At a concentration of 12 μg/ml and higher, detectable fibrinogen binding was totally eliminated.

Without wishing to be bound by any particular theory, the fact that H44L4 appears to inhibit platelet function (aggregation and serotonin release) and to require a portion of GPIIb remote from the fibrinogen binding region for binding, indicates that H44L4 can inhibit fibrinogen binding to platelets in a different manner than conventional platelet antagonists. To confirm that the effect of H44L4 on platelet function does result in the inhibition of fibrinogen binding, a dose response curve utilizing various concentrations of H44L4 with ADP-stimulated platelets and $^{125}$I-fibrinogen was generated using methods described previously in Bennett et al. (1983, Proc. Natl. Acad. Sci. USA 80:2417-2421). Briefly, gel-filtered platelets ($7.35 \times 10^7$ cells) were incubated with various concentrations of H44L4 in the presence of $^{125}$I-fibrinogen, CaCl$_2$, and ADP (final concentrations, 109 μg/ml, 0.5 mM, and 10 μM, respectively) for 3 minutes at 37° C. Platelet suspensions were then centrifuged through an oil interface to separate bound fibrinogen from free, and the amount of platelet-bound fibrinogen was measured by counting the $^{125}$I in the cell pellets. The data disclosed herein demonstrate that at the lowest concentration of H44L4 tested (6.4 μg/ml), fibrinogen binding was reduced to only 5.4% of the control amount obtained in the absence of H44L4 (FIG. 15). At a concentration of 12 μg/ml and higher, fibrinogen binding was totally eliminated (FIG. 15).

Thus, the data disclosed herein demonstrate that H44L4 can inhibit fibrinogen binding and platelet activation in a manner distinct from ReoPro™, and other similar platelet antagonists. Without wishing to be bound by any particular theory, it may be that H44L4 mediates its effect by binding to GPIIb/IIIa and preventing the molecule from undergoing a conformational change required for downstream activation events. This possibility is very important given that recently proposed models of the integrin molecule, such as, for instance, Takagi et al. (2002, Cell 110:599-611) and Beglova et al. (2002, Nature Struct. Biol. 9:282-287) suggest that in their unactivated state, integrins are bent over in a region referred to as the "genu" in between the "thigh" and "calf" domains. Upon activation, integrins may open like switchblades exposing or inducing high-affinity ligand-binding sites in their N-proximal regions. Given that H44L4 requires amino acids 447-1009 (a region of GPIIb that spans the thigh/genu/calf domains) for binding, H44L4 may stabilize the inactive state or otherwise inhibit the opening of the "switchblade" necessary for activation.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for inhibiting blood clotting in vivo, said method comprising administering to a human patient an effective amount of an antibody that inhibits platelet function in vivo, thereby inhibiting blood clotting in vivo, wherein said antibody is an unglycosylated H44L4 Fab [SEQ ID NO:64 (H44) and SEQ ID NO:70 (L4)].

2. A method of contacting an antibody with a glycoprotein IIb/IIIa on a platelet in vivo, comprising administering an effective amount of an antibody to a human patient, wherein said antibody is an unglycosylated H44L4 Fab [SEQ ID NO:64 (H44) and SEQ ID NO:70 (L4)], further wherein when said antibody is bound to said glycoprotein IIb/IIIa on a platelet, platelet function is inhibited.

* * * * *

SEQUENCE LISTING

```
<160> NUMBER OF SEQ ID NOS: 182

<210> SEQ ID NO 1
<211> LENGTH: 366
<212> TYPE: DNA
<213> ORGANISM: Homo sapiens
<220> FEATURE:
<221> NAME/KEY: misc_feature
<222> LOCATION: (74)..(74)
<223> OTHER INFORMATION: n is a, c, g, or t

<400> SEQUENCE: 1
caggtgcagc tggtgcagtc tggggctgag gtgaagaagc ctggggcctc agtgagggtc      60
tcctgtaagg cttntggata caagttcacc ggctcctata tacactgggt gcgacaggcc     120
cctggacaag ggcttgagtg gatgggccgg atcaacccta caatggtgt cacgaactat     180 gcgcagatct ttcaggacag ggtcaccatg accagggaca cgtccatcac cacggcctac     240
atggagttga gcagcctgag atcggacgac acggccgtat attactgtgc gagagatatg     300
atagtcgaca ctttcgcggt cggttgtgac tcctggggcc agggaacccc ggtcaccgtc     360
tcctca                                                                 366

<210> SEQ ID NO 2
<211> LENGTH: 354
<212> TYPE: DNA
<213> ORGANISM: Homo sapiens

<400> SEQUENCE: 2
caggtgcagc tggtgcagtc aggggctgag gtgaagaagc ctggggcctc agtgaaggtt      60
```

| | |
|---|---|
| tcctgcaagg catctggata cagcttcagc aattactata tgcactgggt gcgacaggcc | 120 |
| cctgagaaag ggcttgagtg gatgggaata atcaacccta aggtggtac cacaagctac | 180 |
| gcacagaagt tccagggcag agtcacgatt gccgcggaca gttcacgaa ctcggcctac | 240 |
| atggagccga gcagcctgag atatgaggac acggccgtgt attttgtgc gagagctaag | 300 |
| tttttcatggt cgcctgatat ctggggccaa gggacagtgg tcaccgtctc ttca | 354 |

<210> SEQ ID NO 3
<211> LENGTH: 369
<212> TYPE: DNA
<213> ORGANISM: Homo sapiens

<400> SEQUENCE: 3

| | |
|---|---|
| gaggtgcagc tggtggagtc tgggggaggc ctggtcaagc ctggggggtc cctgagactc | 60 |
| tcctgtgcag cctctggatt caccttcagt agctatagca tgaactgggt ccgccaggct | 120 |
| ccagggaagg ggctggagtg gtctcatcc attagtagta gtagtagtta catatactac | 180 |
| gcagactcag tgaagggccg attcaccatc tccagagaca acgccaagaa ctcactgtat | 240 |
| ctgcaaatga acagcctgag agccgaggac acggctgtgt attactgtgc gagagaccac | 300 |
| cctaattact atgatagtag tggtctcttt gactactggg gccagggaac cctggtcacc | 360 |
| gtctcctca | 369 |

<210> SEQ ID NO 4
<211> LENGTH: 351
<212> TYPE: DNA
<213> ORGANISM: Homo sapiens

<400> SEQUENCE: 4

| | |
|---|---|
| caggtgcagc tggtggagtc tgggggaggc gtggtccagc ctggggggtc cctgagactc | 60 |
| tcctgtgcag cctctggatt caccttcagt agctatgcta tgcactgggt ccgccaggct | 120 |
| ccaggcaagg ggctggagtg ggtggcagtt atatcatatg atggaagtaa taaatactac | 180 |
| gcagactccg tgaagggccg attcaccatc tccagagaca attccaagaa cacgctgtat | 240 |
| ctgcaaatga acagcctgag acctgaggac acggctgtgt attactgtgc gagaggtggg | 300 |
| gtagcagctt ttgactactg ggccaggga accctggtca ccgtctcctc a | 351 |

<210> SEQ ID NO 5
<211> LENGTH: 351
<212> TYPE: DNA
<213> ORGANISM: Homo sapiens

<400> SEQUENCE: 5

| | |
|---|---|
| caggtgcagc tggtggagtc tgggggaggc gtggtccagc ctggggggtc cctgagactc | 60 |
| tcctgtgcag cctctggatt caccttcagt aactatgcta tgcactgggt ccgccaggct | 120 |
| ccaggcaagg ggctggagtg ggtggcagtt atatcatatg atggaagtaa taaatactac | 180 |
| gcagactccg tgaagggccg attcaccatc tccagagaca attccaagaa cacgctgtat | 240 |
| ctgcaaatga acagcctgag acctgaggac acggctgtgt attactgtgc gagaggtggg | 300 |
| gtagcagctt ttgactactg ggccaggga accctggtca ccgtctcctc a | 351 |

<210> SEQ ID NO 6
<211> LENGTH: 351
<212> TYPE: DNA
<213> ORGANISM: Homo sapiens

<400> SEQUENCE: 6

```
caggtgcagc tggtggagtc tgggggaggc gtggtccagc ctgggaggtc cctgagactc      60
tcctgtgcag cctctggatt caccttcagt aactatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagcctgag acctgaggac acggctgtgt attactgtgc gagaggtggg     300
gtaggagctt ttgactactg gggccaggga accctggtca ccgtctcctc a              351
```

<210> SEQ ID NO 7
<211> LENGTH: 351
<212> TYPE: DNA
<213> ORGANISM: Homo sapiens

<400> SEQUENCE: 7

```
caggtgcagc tggtggagtc tgggggaggc gtggtccagc ctgggaggtc cctgagactc      60
tcctgtgcag cctctggatt caccttcagt aactatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagtctgag acctgaggac acggctgtgt attactgtgc gagaggtggg     300
gtagcagctt ttgactactg gggccaggga accctggtca ccgtctcctc a              351
```

<210> SEQ ID NO 8
<211> LENGTH: 351
<212> TYPE: DNA
<213> ORGANISM: Homo sapiens

<400> SEQUENCE: 8

```
caggtgcagc tggtggagtc tgggggaggc gtggtccagc ctgggaggtc cctgagactc      60
tcctgtgcag cctctacatt caccttcagt aactatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagcctgag acctgaggac acggctgtgt attactgtgc gagaggtggg     300
gtagcggctt ttgactactg gggccaggga accctggtca ccgtctcctc a              351
```

<210> SEQ ID NO 9
<211> LENGTH: 351
<212> TYPE: DNA
<213> ORGANISM: Homo sapiens

<400> SEQUENCE: 9

```
caggtgcagc tggtggagtc tgggggaggc gtggtccagc ctgggaggtc cctgagactc      60
tcctgtgcag cctctggatc caccttcagt tactatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagcctgag acctgaggac acggctgtgt attactgtgc gagaggtggg     300
gtagcagctt ttgactactg gggtcaggga accctggtca ccgtctcctc a              351
```

<210> SEQ ID NO 10
<211> LENGTH: 351
<212> TYPE: DNA
<213> ORGANISM: Homo sapiens

<400> SEQUENCE: 10

```
caggtgcagc tggtggagtc tgggggagcc atggtccagc ctggaggtc cctgagactc      60 tcctgtgcgg cctctggatt cccccttcagt aactatgcta tgcactgggt ccgccaggct   120
ccaggcaagg ggctggagtg ggtggcagtt atatcatatg atggaagtaa taaatactac   180
gcagactccg tgaagggccg attcaccatc tccagagaca attccaagaa cacgctgtat   240
ctgcaaatga acagcctgag acctgaggac acggctgtgt attactgtgc gagaggtggg   300
gtagcagctt ttgactactg gggccaggga accctggtca ccgtctcctc a            351

<210> SEQ ID NO 11
<211> LENGTH: 336
<212> TYPE: DNA
<213> ORGANISM: Homo sapiens

<400> SEQUENCE: 11
caggtgcagc tggtggagtc tgggggaggc gtggtccagc ctgggaggtc cctgagactc     60
tcctgtgcag cctctggatt caccttcagt tactatgcta tggtctgggt ccgccaggct   120
ccaggcaagg ggctagagtg ggtggcagtt atatcaaatg atggtaggaa taaatactac   180
gcagactccg tgaagggccg attcaccatc tccagagaca cgccaagaa cacgctctat    240 ttgcaaatga acagtctgag agtcgaggac acggctgtgt attactgtgc aaggttgggc   300
tactggggcc cgggaaccct ggtcaccgtc tcctca                            336

<210> SEQ ID NO 12
<211> LENGTH: 345
<212> TYPE: DNA
<213> ORGANISM: Homo sapiens

<400> SEQUENCE: 12
caggtgcagc tggtggagtc tgggggaggc gtggtccagc ctggaaggtc cctgagactc     60
tcctgtgcag cctctggatt caccttcagt aactttaata tgcactgggt ccgccaggct   120
ccaggcaagg ggctggagtg ggtggcactt atatcatatg atggaagtag taaatactat   180
acagactccg tgaagggccg attcaccatc tccagagaca attccaagaa cacgctgtat   240
ctgcaaatga acagcctgag acctgaggac acggctgtat attactgtat ggtagtggga   300
gcctttgact actggggcca gggaaccctg gtcaccgtct cctca                   345

<210> SEQ ID NO 13
<211> LENGTH: 345
<212> TYPE: DNA
<213> ORGANISM: Homo sapiens

<400> SEQUENCE: 13
caggtgcagc tggtggagtc tgggggaggc gtggtccagc ctgggaggtc cctgagactc     60
tcctgtgcag cctctggatt caccttcagt aactttaata tgcactgggt ccgccaggct   120
ccaggcaagg ggctggagtg ggtggcacta atatcatatg atggaagtaa taaaaattat   180
gcagactccg tgaagggccg attcaccatc tccagagaca actccaagaa cacgctgttt   240
ctgcaaatga acagcctgag agctgaggac acggctgtgt attattgtat ggtagtggga   300
gcctttgact actggggcca gggtaccctg gtcaccgtct cctca                   345

<210> SEQ ID NO 14
<211> LENGTH: 345
<212> TYPE: DNA
<213> ORGANISM: Homo sapiens

<400> SEQUENCE: 14
```

```
caggtgcagc tggtggagtc tgggggaggc gtggtccagc ctggagggtc cctgagactc    60
tcctgtgcaa cctctggatt caccttcagt aactttaata tgcactgggt ccgccaggct   120
ccaggcaagg ggctggagtg ggtggcacta atatcatatg atggaagtaa taaaaactat   180
gcaaactccg tgaagggccg attcaccatc tccagagaca actccaagaa cacgctgttt   240
ctgcaaatga acagcctgag agttgaagac acggctgtat attattgtat ggtagtggga   300
gcctttgact actggggcca gggtaccctg gtcaccgtct cctca                   345
```

<210> SEQ ID NO 15
<211> LENGTH: 345
<212> TYPE: DNA
<213> ORGANISM: Homo sapiens

<400> SEQUENCE: 15

```
caggtgcagc tggtggagtc tgggggaggc gtggtccagc ctggagggtc cctgagactc    60
tcctgtgcag cctctggatt caccatcagt aattatcaca tacactgggt ccgccaggct   120
ccaggcaagg ggctggagtg ggtggcattt atatcatatg atggaagtaa taaatactat   180
gcagactccg tgaagggccg attcaccatc tccagagaca attccaagaa cacgttgttt   240
ctgcaaatga acagcctgac aactgaggac acggctgtgt attactgtgc gatagtggga   300 cccttttgact accggggcca gggaaccctg gtcaccgtct cttca                  345
```

<210> SEQ ID NO 16
<211> LENGTH: 357
<212> TYPE: DNA
<213> ORGANISM: Homo sapiens

<400> SEQUENCE: 16

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagta cattgggtat atctattaca gtgggagcac cgactacaac   180
ccctccctca agagtcgagt caccatatca gtagacacgt ccgagaacca gttctccctg   240
aagctgagct ctgtgaccgc cgcagacacg gccgtctatt actgtgcgag aagcccacct   300
gttattcggc cgctatgga cgtctggggc caagggacca cggtcaccgt ctcctca       357
```

<210> SEQ ID NO 17
<211> LENGTH: 318
<212> TYPE: DNA
<213> ORGANISM: Homo sapiens

<400> SEQUENCE: 17

```
gacatccaga tgacccagtc tccatcctcc ctgtctgtat ctgtaggaga cagagtcacc    60
atcacttgcc gggcaagtca gaccattact atgtatttaa attggtatca gcagaaacca   120
gggaaagccc ctaagctcct gatctatgct ggatccagtt tgccaagtgg agtcccacca   180
aggttcagtg gcagtggatc tgggacagat ttcacactca ccatcagcag tctgcaacct   240
gaagattttg caacttacta ctgtcaacag agttacagta ccctcacttt cggcggaggg   300
accaaggtgg agatgaaa                                                 318
```

<210> SEQ ID NO 18
<211> LENGTH: 321
<212> TYPE: DNA
<213> ORGANISM: Homo sapiens

<400> SEQUENCE: 18

```
gacatccaga tgacccagtc tccatcctcc ctgtctgcat ctgtaggaga cagagtcacc    60
atcacttgcc gggcgagtca gggcattagc agttatttag cctggtatca gcagaaacca   120
gggaaagttc ctaaactcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataacagtg ccccccctca ctttggcgga   300
gggaccaagg tggagatcaa a                                             321

<210> SEQ ID NO 19
<211> LENGTH: 321
<212> TYPE: DNA
<213> ORGANISM: Homo sapiens

<400> SEQUENCE: 19
gacatccagt tgacccagtc tccaaccttc ctgtctgcat ctgtagggga cagagtcacc    60
atcacttgcc gggccagtca gggcattagt cgttatttag cctggtatca gcaaaaacca   120
gggaaagccc ctaagctcct gatctatgct gcatccactt tgcaaagtgg ggtcccatca   180
aggttcagcg gcagtggatc tgggacagac ttcactctca cattcagcag cctgcagcct   240
gaagattttg caacttatta ctgtcaacag cttaatagtt acccgttcac tttggcgga   300 gggaccacgg tggagatcaa a                                             321

<210> SEQ ID NO 20
<211> LENGTH: 336
<212> TYPE: DNA
<213> ORGANISM: Homo sapiens

<400> SEQUENCE: 20
gatattgtga tgactcagtc tccactctcc ctgcccgtca cccctggaga gccggcctcc    60
atctcctgca ggtctagtca gagcctcctg tatagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc   240 agcagagtgg aggctgagga tgttggggtt tattactgca tgcaaggtac acactggcct   300
tggacgttcg gccaagggac caaggtggaa atcaaa                             336

<210> SEQ ID NO 21
<211> LENGTH: 336
<212> TYPE: DNA
<213> ORGANISM: Homo sapiens

<400> SEQUENCE: 21
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc   240 agcagagtgg aggctgagga tgttggggtt tattactgca tgcaagctct acaaactccg   300
agcacttttg gccaggggac caagctggag atcaaa                             336

<210> SEQ ID NO 22
<211> LENGTH: 336
<212> TYPE: DNA
<213> ORGANISM: Homo sapiens

<400> SEQUENCE: 22
```

```
gatattgtga tgactcagtc tccactctcc ctgcccgtca ccctggaga gccggcctcc      60 atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccc    300
tacacttttg gccaggggac caagctggag atcaaa                              336

<210> SEQ ID NO 23
<211> LENGTH: 336
<212> TYPE: DNA
<213> ORGANISM: Homo sapiens

<400> SEQUENCE: 23
gatattgtga tgactcagtc tccactctcc ctgcccgtca ccctggaga gccggcctcc      60 atctcctgca ggtctagtca gagcctcctg cataggaatg gatacaacta tttggattgg    120
tacctgcaga ggccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct gcagactccg    300
tacactttcg gccaggggac caagctgcag atcaaa                              336

<210> SEQ ID NO 24
<211> LENGTH: 336
<212> TYPE: DNA
<213> ORGANISM: Homo sapiens

<400> SEQUENCE: 24
gatattgtga tgactcagtc tccactctcc ctgcccgtca ccctggaga gccggcctcc      60 atctcctgca ggtctagtca gagcctcctg catagtaatg gatacaacta tttagattgg    120
tacctgcaga agccagggca gtctccacag ctcctgatct atttgggttc taatcgggcc    180
tccggggtcc ctgacaggtt cagtggcagt ggatcgggca cagattttac actgaacatc    240
agcagagtgg aggctgacga tgttggggtt tattactgca tgcaggctct acaaaccccg    300
tacacttttg gccaggggac caagcttgag atcaaa                              336

<210> SEQ ID NO 25
<211> LENGTH: 336
<212> TYPE: DNA
<213> ORGANISM: Homo sapiens

<400> SEQUENCE: 25
gatattgtga tgactcagtc tccaccctcc ctgcccgtca ccctggaga gccggcctcc      60 atctcctgca ggtctagtca gagcctcctg catactaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgacaatc    240
agtagagtgg aggctgagga tgttggggtt ttttactgca tgcaagctct agaacctccg    300
tacacttttg gccaggggac caagctggag atcaaa                              336

<210> SEQ ID NO 26
<211> LENGTH: 336
<212> TYPE: DNA
<213> ORGANISM: Homo sapiens

<400> SEQUENCE: 26
```

```
gatattgtga tgactcagtc tccactctcg ctgtccgtca gtcctggaga gccggcctcc      60
atctcctgca ggtctagtca gagcctccta gattctaatg dacacaactt tttggattgg     120
tacctgcaga agccagggca gtctccacaa ctcctaatat tgtgggggtc ttatcgggcc     180
ttgggtgtcc ctgacaggtt cactggcagt gggacaggca cagattttac actgaaaatc     240
agcagagtgg agcctgagga tgttggggtt tactactgca tgcaaggtct gcaagctcct     300
atcacttttg gccaggggac caagctggac atcaaa                               336

<210> SEQ ID NO 27
<211> LENGTH: 336
<212> TYPE: DNA
<213> ORGANISM: Homo sapiens

<400> SEQUENCE: 27
gatattgtga tgactcagtc tccactctcc ctgcccgtca ccctggaga gccggcctcc       60 atctcctgca ggtctagtca gagcctcctg catcgtaatg dacacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggcgtt tattactgca tgcaagctct acaaactcct    300
ttcactttcg ccctgggac caaagtggat atcaaa                                336

<210> SEQ ID NO 28
<211> LENGTH: 336
<212> TYPE: DNA
<213> ORGANISM: Homo sapiens

<400> SEQUENCE: 28
gatattgtga tgactcagtc tccactctcc ctgcccgtca ccctggaga gccggcctcc       60 atctcctgca ggtctagtca gagcctcctg catagtgatg gatacaacta tttggattgg    120
tacctgcaga agccagggca gtctccacat ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaacgcca    300
ttcactttcg ccctgggac caaagtggat atcaaa                                336

<210> SEQ ID NO 29
<211> LENGTH: 336
<212> TYPE: DNA
<213> ORGANISM: Homo sapiens

<400> SEQUENCE: 29
gatattgtga tgactcagtc tccactctcc ctgcccgtca ccctggaga gccggcctcc       60 atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaagtcct    300
cccactttcg gcggagggac caaggtggag atcaaa                               336

<210> SEQ ID NO 30
<211> LENGTH: 336
<212> TYPE: DNA
<213> ORGANISM: Homo sapiens

<400> SEQUENCE: 30
```

```
gatattgtga tgactcagtc tccagtctcc ctggccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc tactcgggcc   180
tccggggtcc ctgacaggtt cagtggcagt ggatcaggca cagattttac actgaaaatc   240
aacagagtgg aggctgagga tgttggggta tattactgca tgcaagctct acaatctcct   300
ttcactttcg gcggagggac caaggtggag atcaaa                             336

<210> SEQ ID NO 31
<211> LENGTH: 336
<212> TYPE: DNA
<213> ORGANISM: Homo sapiens

<400> SEQUENCE: 31
gatattgtga tgactcagtc tccagtctcc ctggccgtca cccctggaga gccggcctcc    60
atctcctgca ggtctagtca gagcctcctg catagtaatg gatacaacta tctggattgg   120
tacctgcaga agccagggca gtctccacag ctcctgatct atttgggttc tactcgggcc   180
tccggggtcc ctgacaggtt cagtggcagt ggatcaggca cagattttac actgaaaatc   240
aacagagtgg aggctgagga tgttggggtg tattactgca tgcaagctct acaatctcct   300
ttcactttcg gcggagggac caaggtgcag atcaaa                             336

<210> SEQ ID NO 32
<211> LENGTH: 336
<212> TYPE: DNA
<213> ORGANISM: Homo sapiens

<400> SEQUENCE: 32
gatattgtga tgactcagtc tccactctcc ctgcccgtca cccctggaga gccggcctcc    60
atctcctgca ggtctagtca gagcctcctg cacagtaatg gaaacaatta tttggattgg   120
tacctgcaga agccagggca gtctccacag ctcctgatct acttggcttc taatcgggcc   180
tccggggtcc ctgacaggtt cagtggcagt ggatcaggca cggattttac actgaaaatc   240
agcagagtgg agcctgagga tgttggactt tattactgca tgcaagctct acaaactccg   300
ctcactttcg gcggagggag caaggtggag atcaaa                             336

<210> SEQ ID NO 33
<211> LENGTH: 336
<212> TYPE: DNA
<213> ORGANISM: Homo sapiens

<400> SEQUENCE: 33
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt gtatcaggca cagattttac actgaaaatc   240
agcagagtgg aggctgagga tgttggggtt tattactgca tgcaagctct acaaactccg   300
atcaccttcg gccaagggac acgactggag attaaa                             336

<210> SEQ ID NO 34
<211> LENGTH: 336
<212> TYPE: DNA
<213> ORGANISM: Homo sapiens

<400> SEQUENCE: 34
```

```
gatattgtga tgactcagtc tccactctcc ctgcccgtca ccctggaga gccggcctcc      60 atctcctgca ggtctagtca gagcctcctg catagtaatg gatacaacta tttggattgg    120
tacctgcaga ggccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cccaccttcg gccaagggac acgactggag attaaa                              336
```

<210> SEQ ID NO 35
<211> LENGTH: 339
<212> TYPE: DNA
<213> ORGANISM: Homo sapiens

<400> SEQUENCE: 35

```
gatattgtga tgactcagtc tccactctcc ctgcccgtca ccctggaga gccggcctcc      60 atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
ccggtcacct tcggccaagg gacacgactg gagattaaa                           339
```

<210> SEQ ID NO 36
<211> LENGTH: 339
<212> TYPE: DNA
<213> ORGANISM: Homo sapiens

<400> SEQUENCE: 36

```
gatattgtga tgactcagtc tccactctcc ctgcccgtca ccctggaga gccggcctcc      60 atctcctgca ggtctagtca gagcctcctg catagtaatg gatacaacta tttggattgg    120
tacctgcaga agccagggca gtctccacaa ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcgt    300
ccggtcacct tcggccaagg gacacgactg gagattaaa                           339
```

<210> SEQ ID NO 37
<211> LENGTH: 336
<212> TYPE: DNA
<213> ORGANISM: Homo sapiens

<400> SEQUENCE: 37

```
gatattgtga tgactcagtc tccactctcc ctgcccgtca ccctggaga gccggcctcc      60 atctcctgca ggtctagtca gagcctcctg catactaatg gatacaacta tttggattgg    120
tacctgcaga agccagggca gtctccacag ctcctgatct atttgggttc tcatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccg    300
atcaccttcg gccaagggac acgactggaa attaaa                              336
```

<210> SEQ ID NO 38
<211> LENGTH: 336
<212> TYPE: DNA
<213> ORGANISM: Homo sapiens

<400> SEQUENCE: 38

```
gatattgtga tgactcagtc tccactctcc ctgcccgtca ccctggaga gccggcctcc      60 atctcctgca ggtctggtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggcg cagattttac actgaaaatc    240
agcagagtgg aggctgagga tgttggggtt tattactgca tgcaagctct acaaactccg    300
atcaccttcg gccaagggac acgactggag attgaa                              336

<210> SEQ ID NO 39
<211> LENGTH: 336
<212> TYPE: DNA
<213> ORGANISM: Homo sapiens

<400> SEQUENCE: 39
gatattgtga tgactcagtc tccactctcc ctgcccgtca ccctggaga gccggcctcc      60 atctcctgca ggtccagtca gagcctcctc catactaatg gatacaacta tttggattgg    120
tatgtgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactttg    300
atcaccttcg gccaagggac acgactggag attaaa                              336

<210> SEQ ID NO 40
<211> LENGTH: 336
<212> TYPE: DNA
<213> ORGANISM: Homo sapiens

<400> SEQUENCE: 40
gatattgtga tgactcagtc tccactctcc ctgcccgtca ccctggaga gccggcctcc      60 atctcctgca ggtctagtca gagcctcctg cacagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaagatc    240
agcagagtgg aggctgaaga tattggggtt tattactgca tgcaagcgca agactctccg    300
gtcaccttcg gccaagggac acggctagac attaac                              336

<210> SEQ ID NO 41
<211> LENGTH: 336
<212> TYPE: DNA
<213> ORGANISM: Homo sapiens

<400> SEQUENCE: 41
gatattgtga tgactcagtc tccactctcc ctgcccgtca ccctggaga gccggcctcc      60 atctcctgta ggtctaatca gagcgtcctg catagtaatg gacggcacta tttggattgg    120
tatttgcaga agccagggca gtctccacag ctcctgatct acatggtttt taatcgggcc    180
tccggggtcc ctgacaggtt cagtggcagt ggatcaggca cagattttac actgaaaatc    240
agcagagtgg agtctgagga tgtaggggtt tattactgca tgcaagctca acaaactccg    300
gtcaccttcg gccaagggac acgactggac attaag                              336

<210> SEQ ID NO 42
<211> LENGTH: 324
<212> TYPE: DNA
<213> ORGANISM: Homo sapiens

<400> SEQUENCE: 42
```

```
gaaattgtgt tgacacagtc tccaggcacc ctgtctttgt ctccagggga aagagccacc      60
ctctcctgca gggccagtca gagtgttggc agcagctact tagcctggta ccagcagaaa     120
cctggccagg ctcccaggct cctcatctat ggtgtatcca gcagggccac tggcatccca     180
gacaggttca gtggcagtgg gtctgggaca gacttcactc tcaccatcag caggctggag     240
cctgaagatt ttgcagtgta ttactgtcag cagtatggtg gctcacctct cactttcggc     300
ggagggacca cggtggagat caaa                                            324

<210> SEQ ID NO 43
<211> LENGTH: 324
<212> TYPE: DNA
<213> ORGANISM: Homo sapiens

<400> SEQUENCE: 43
gaaattgtgt tgacgcagtc tccaggcacc ctgtctttgt ctccagggga aagagccacc      60
ctctcctgca gggccagtca gagtgttggc aacaactact tagcctggta ccagcagaga     120
cctggccggg ctcccaggct cgtcatgtat gatccatcca gcagggccac tggcatccca     180
gacaggttca gtggcagtgg gtctgggaca gacttcactc tcaccatcag cagactggag     240
cctgaagatt ttgcggttta ttactgtcag cagtatggta actcacctcc cactttcggc     300
ggagggacca aggtggagat caaa                                            324

<210> SEQ ID NO 44
<211> LENGTH: 321
<212> TYPE: DNA
<213> ORGANISM: Homo sapiens

<400> SEQUENCE: 44
gaaattgtgt tgacgcagtc tccagacacc ctgtctttgt ctccagggga cagggccacc      60
ctctcctgca gggccagtca gagtgttagt aactacttag cctggtacca gcagaaagct     120
ggccgggctc ccagtctcct catctatggg acatccagga gggccactga catcccagac     180
aggttcagtg gcagtgggtc tgggacagac ttcactctca ccatcagcag actggaacct     240
gaagattctg cagtatatta ctgtcagcag tatggtagcg catcgctcac tttcggcgga     300
gggaccaagg tagagatcaa a                                               321

<210> SEQ ID NO 45
<211> LENGTH: 321
<212> TYPE: DNA
<213> ORGANISM: Homo sapiens

<400> SEQUENCE: 45
gaaattgtgt tgacacagtc tccagccacc ctgtctgtgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctgac gttcggccaa     300
gggaccaagg tggaaatcaa a                                               321

<210> SEQ ID NO 46
<211> LENGTH: 318
<212> TYPE: DNA
<213> ORGANISM: Homo sapiens

<400> SEQUENCE: 46
```

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcccacttt cggcggaggg     300
accaaggtgg agatcaaa                                                   318

<210> SEQ ID NO 47
<211> LENGTH: 321
<212> TYPE: DNA
<213> ORGANISM: Homo sapiens

<400> SEQUENCE: 47
gaaattgtgt tgacacagtc tccagccacc ctgtcgttgt ctccagggga aagagccacc      60
ctctcctgca gggccagtca gagtgttagg agcttcttag cctggtacca acagaagcct     120
ggccaggctc ccaggctcct catttatgat acatccaaga ggccactgg catcccagac      180 aggttcagtg gcagtgggtc tgggacagac ttcactctca ccatcagcag cctagaacct     240
gaagattttg cagtgtatta ctgtcagcag cgtagcagct ggccgctcac tttcggcgga     300
gggaccacgg tggagatcaa a                                               321

<210> SEQ ID NO 48
<211> LENGTH: 324
<212> TYPE: DNA
<213> ORGANISM: Homo sapiens

<400> SEQUENCE: 48
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgat caccttcggc     300
caagggacac gactggagat taaa                                            324

<210> SEQ ID NO 49
<211> LENGTH: 318
<212> TYPE: DNA
<213> ORGANISM: Homo sapiens

<400> SEQUENCE: 49
gacatccaga tgacccagtc tccatccttc ctgtctgcat ctgtaggaga cagagtcacc      60
atctcttgcc gggcaagtca gagcattgac agctatataa attggtatca gcagaaacca     120
gggaaagccc ctaagctcct gatctatgct gcatccagtt tgcaacgtgg ggtcccatca     180
aggttcagtg gcagtggatc tgggacagat ttcactctca ccatcagcag tctacaacct     240
gaagattttg caacttacta ctgtcaacag acttacagca ccctcacttt cggcggaggg     300
accaaggtgg agatcaaa                                                   318

<210> SEQ ID NO 50
<211> LENGTH: 330
<212> TYPE: DNA
<213> ORGANISM: Homo sapiens

<400> SEQUENCE: 50
```

```
cagtctgccc tgactcagcc tgcctccgtg tctgggtctc ctggacagtc gatcaccatc    60
tcctgcactg gaaccagcag tgacgttggt ggttataagt atgtctcctg gtaccaacag   120
cacccaggca aagcccccaa actcataatt tatgatgtca ccaatcggcc ctcaggggtt   180
tctaagcgct tctctggctc caagtctggc aacacggcct ccctgaccat ctctgggctc   240
caggctgagg acgaggctga ttattactgc agttcatata agcaggag cactcccgtc     300 ttcggcggag ggaccaaggt gaccgtccta                                     330

<210> SEQ ID NO 51
<211> LENGTH: 324
<212> TYPE: DNA
<213> ORGANISM: Homo sapiens

<400> SEQUENCE: 51
tcttctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa aactaccggc cctcagggat cccagaccga   180
ttctctggct ccagctcagg aaacacagct tccttgacca tcactgggc tcaggcggaa   240 gatgaggctg actattactg taactcccgg gacagcagtg gtaaccattg ggtgttcggc   300
ggagggacca agctgaccgt ccta                                           324

<210> SEQ ID NO 52
<211> LENGTH: 330
<212> TYPE: DNA
<213> ORGANISM: Homo sapiens

<400> SEQUENCE: 52
cagcttgtgc tgactcaatc gccccctgcc tctgcctccc tgggagcctc ggtcaagctc    60
acctgcactc tgagcagtgg gcacagcagt tacgccatcg catggcatca gcaacagcca   120
gagaagggcc ctcggtactt gatgaacctt aatagtgatg cagccacag caaggggac    180 ggggtccctg atcgcttctc aggctccagc tctgggctg agcgctacct caccatctcc   240
agcctccagt ctgaggatga ggctgactat tactgtcagt cttgggacac tgcgaggtg   300 ttcggcgggg ggaccaagtt gaccgtcctg                                     330

<210> SEQ ID NO 53
<211> LENGTH: 327
<212> TYPE: DNA
<213> ORGANISM: Homo sapiens

<400> SEQUENCE: 53
caggctgtgg tgactcagga gccctcactg actgtgtccc caggagggac agtcactctc    60
acctgtgact ccagcactgg agctgtcacc agtggtcatt atccctactg gctccagcag   120
aagcctggcc aagcccccag gacactcatt tatgatacac ataacaaaca ctcctggaca   180
cctggccggt tctcaggctc cctccttggg ggcaaagctg ccctgaccct tcgggtgcg   240 cagcctgagg atgaggctga gtattactgc tcgctctcgt atagtgctgt ttgggtgttc   300
ggcggaggga ccaagctgac cgtccta                                        327

<210> SEQ ID NO 54
<211> LENGTH: 122
<212> TYPE: PRT
<213> ORGANISM: Homo sapiens
<220> FEATURE:
<221> NAME/KEY: misc_feature
<222> LOCATION: (25)..(25)
```

<223> OTHER INFORMATION: Xaa can be any naturally occurring amino acid

<400> SEQUENCE: 54

Gln Val Gln Leu Val Gln Ser Gly Ala Glu Val Lys Lys Pro Gly Ala
1               5                   10                  15

Ser Val Arg Val Ser Cys Lys Ala Xaa Gly Tyr Lys Phe Thr Gly Ser
            20                  25                  30

Tyr Ile His Trp Val Arg Gln Ala Pro Gly Gln Gly Leu Glu Trp Met
        35                  40                  45

Gly Arg Ile Asn Pro Asn Asn Gly Val Thr Asn Tyr Ala Gln Ile Phe
    50                  55                  60

Gln Asp Arg Val Thr Met Thr Arg Asp Thr Ser Ile Thr Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Met Ile Val Asp Thr Phe Ala Val Gly Cys Asp Ser Trp
            100                 105                 110

Gly Gln Gly Thr Pro Val Thr Val Ser Ser
        115                 120

<210> SEQ ID NO 55
<211> LENGTH: 118
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Asn Tyr
            20                  25                  30

Tyr Met His Trp Val Arg Gln Ala Pro Gly Glu Gly Leu Glu Trp Met
        35                  40                  45

Gly Ile Ile Asn Pro Lys Gly Gly Thr Thr Ser Tyr Ala Gln Lys Phe
    50                  55                  60

Gln Gly Arg Val Thr Ile Ala Ala Asp Lys Phe Thr Asn Ser Ala Tyr
65                  70                  75                  80

Met Glu Pro Ser Ser Leu Arg Tyr Glu Asp Thr Ala Val Tyr Phe Cys
                85                  90                  95

Ala Arg Ala Lys Phe Ser Trp Ser Pro Asp Ile Trp Gly Gln Gly Thr
            100                 105                 110

Val Val Thr Val Ser Ser
        115

<210> SEQ ID NO 56
<211> LENGTH: 123
<212> TYPE: PRT
<213> ORGANISM: Homo sapiens

<400> SEQUENCE: 56

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Pro Asn Tyr Tyr Asp Ser Gly Leu Phe Asp Tyr
            100                 105                 110

Trp Gly Gln Gly Thr Leu Val Thr Val Ser Ser
            115                 120

<210> SEQ ID NO 57
<211> LENGTH: 117
<212> TYPE: PRT
<213> ORGANISM: Homo sapiens

<400> SEQUENCE: 57

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Gly Gly Val Ala Ala Phe Asp Tyr Trp Gly Gln Gly Thr Leu
            100                 105                 110

Val Thr Val Ser Ser
            115

<210> SEQ ID NO 58
<211> LENGTH: 117
<212> TYPE: PRT
<213> ORGANISM: Homo sapiens

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Gly Gly Val Ala Ala Phe Asp Tyr Trp Gly Gln Gly Thr Leu
            100                 105                 110

Val Thr Val Ser Ser
            115

<210> SEQ ID NO 59
<211> LENGTH: 117
<212> TYPE: PRT

<213> ORGANISM: Homo sapiens

<400> SEQUENCE: 59

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Gly Gly Val Gly Ala Phe Asp Tyr Trp Gly Gln Gly Thr Leu
            100                 105                 110

Val Thr Val Ser Ser
        115
```

<210> SEQ ID NO 60
<211> LENGTH: 115
<212> TYPE: PRT
<213> ORGANISM: Homo sapiens

<400> SEQUENCE: 60

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Gly Gly Val Ala Ala Phe Asp Tyr Trp Gly Gln Gly Thr Leu
            100                 105                 110

Val Thr Val
        115
```

<210> SEQ ID NO 61
<211> LENGTH: 117
<212> TYPE: PRT
<213> ORGANISM: Homo sapiens

<400> SEQUENCE: 61

```
Gln Val Gln Leu Val Glu Ser Gly Gly Gly Val Val Gln Pro Gly Arg
1               5                   10                  15

Ser Leu Arg Leu Ser Cys Ala Ala Ser Thr Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Gly Gly Val Ala Ala Phe Asp Tyr Trp Gly Gln Gly Thr Leu
            100                 105                 110

Val Thr Val Ser Ser
            115

<210> SEQ ID NO 62
<211> LENGTH: 117
<212> TYPE: PRT
<213> ORGANISM: Homo sapiens

<400> SEQUENCE: 62

Gln Val Gln Leu Val Glu Ser Gly Gly Val Val Gln Pro Gly Arg
 1               5                  10                  15

Ser Leu Arg Leu Ser Cys Ala Ala Ser Gly Ser Thr Phe Ser Tyr Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Gly Gly Val Ala Ala Phe Asp Tyr Trp Gly Gln Gly Thr Leu
            100                 105                 110

Val Thr Val Ser Ser
            115

<210> SEQ ID NO 63
<211> LENGTH: 117
<212> TYPE: PRT
<213> ORGANISM: Homo sapiens

<400> SEQUENCE: 63

Gln Val Gln Leu Val Glu Ser Gly Gly Ala Met Val Gln Pro Gly Arg
 1               5                  10                  15

Ser Leu Arg Leu Ser Cys Ala Ala Ser Gly Phe Pro Phe Ser Asn Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Gly Gly Val Ala Ala Phe Asp Tyr Trp Gly Gln Gly Thr Leu
            100                 105                 110

Val Thr Val Ser Ser
            115

<210> SEQ ID NO 64
<211> LENGTH: 112
<212> TYPE: PRT
```

-continued

<213> ORGANISM: Homo sapiens

<400> SEQUENCE: 64

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Ala Met Val Trp Val Arg Gln Ala Pro Gly Lys Gly Leu Glu Trp Val
        35                  40                  45

Ala Val Ile Ser Asn Asp Gly Arg Asn Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Leu Gly Tyr Trp Gly Pro Gly Thr Leu Val Thr Val Ser Ser
            100                 105                 110

<210> SEQ ID NO 65
<211> LENGTH: 115
<212> TYPE: PRT
<213> ORGANISM: Homo sapiens

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Asn Met His Trp Val Arg Gln Ala Pro Gly Lys Gly Leu Glu Trp Val
        35                  40                  45

Ala Leu Ile Ser Tyr Asp Gly Ser Ser Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Met Val Val Gly Ala Phe Asp Tyr Trp Gly Gln Gly Thr Leu Val Thr
            100                 105                 110

Val Ser Ser
        115

<210> SEQ ID NO 66
<211> LENGTH: 115
<212> TYPE: PRT
<213> ORGANISM: Homo sapiens

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Asn Met His Trp Val Arg Gln Ala Pro Gly Lys Gly Leu Glu Trp Val
        35                  40                  45

Ala Leu Ile Ser Tyr Asp Gly Ser Asn Lys Asn Tyr Ala Asp Ser Val
    50                  55                  60

Lys Gly Arg Phe Thr Ile Ser Arg Asp Asn Ser Lys Asn Thr Leu Phe
65                  70                  75                  80

```
Leu Gln Met Asn Ser Leu Arg Ala Glu Asp Thr Ala Val Tyr Tyr Cys
                85                  90                  95

Met Val Val Gly Ala Phe Asp Tyr Trp Gly Gln Gly Thr Leu Val Thr
            100                 105                 110

Val Ser Ser
        115

<210> SEQ ID NO 67
<211> LENGTH: 115
<212> TYPE: PRT
<213> ORGANISM: Homo sapiens

<400> SEQUENCE: 67

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Asn Phe
            20                  25                  30

Asn Met His Trp Val Arg Gln Ala Pro Gly Lys Gly Leu Glu Trp Val
        35                  40                  45

Ala Leu Ile Ser Tyr Asp Gly Ser Asn Lys Asn Tyr Ala Asn Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Val Glu Asp Thr Ala Val Tyr Tyr Cys
                85                  90                  95

Met Val Val Gly Ala Phe Asp Tyr Trp Gly Gln Gly Thr Leu Val Thr
            100                 105                 110

Val Ser Ser
        115

<210> SEQ ID NO 68
<211> LENGTH: 115
<212> TYPE: PRT
<213> ORGANISM: Homo sapiens

<400> SEQUENCE: 68

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Ile Ser Asn Tyr
            20                  25                  30

His Ile His Trp Val Arg Gln Ala Pro Gly Lys Gly Leu Glu Trp Val
        35                  40                  45

Ala Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Thr Thr Glu Asp Thr Ala Val Tyr Tyr Cys
                85                  90                  95

Ala Ile Val Gly Pro Phe Asp Tyr Arg Gly Gln Gly Thr Leu Val Thr
            100                 105                 110

Val Ser Ser
        115

<210> SEQ ID NO 69
<211> LENGTH: 119
<212> TYPE: PRT
<213> ORGANISM: Homo sapiens

<400> SEQUENCE: 69
```

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Tyr Ile
         35                  40                  45

Gly Tyr Ile Tyr Tyr Ser Gly Ser Thr Asp Tyr Asn Pro Ser Leu Lys
 50                  55                  60

Ser Arg Val Thr Ile Ser Val Asp Thr Ser Glu Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ser Pro Pro Val Ile Arg Pro Ala Met Asp Val Trp Gly Gln Gly
             100                 105                 110

Thr Thr Val Thr Val Ser Ser
            115

<210> SEQ ID NO 70
<211> LENGTH: 106
<212> TYPE: PRT
<213> ORGANISM: Homo sapiens

<400> SEQUENCE: 70

Asp Ile Gln Met Thr Gln Ser Pro Ser Ser Leu Ser Val Ser Val Gly
  1               5                  10                  15

Asp Arg Val Thr Ile Thr Cys Arg Ala Ser Gln Thr Ile Thr Met Tyr
             20                  25                  30

Leu Asn Trp Tyr Gln Gln Lys Pro Gly Lys Ala Pro Lys Leu Leu Ile
         35                  40                  45

Tyr Ala Gly Ser Ser Leu Pro Ser Gly Val Pro Pro Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Leu Thr
                 85                  90                  95

Phe Gly Gly Gly Thr Lys Val Glu Met Lys
            100                 105

<210> SEQ ID NO 71
<211> LENGTH: 107
<212> TYPE: PRT
<213> ORGANISM: Homo sapiens

<400> SEQUENCE: 71

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Val Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Leu
                 85                  90                  95
```

```
Thr Phe Gly Gly Gly Thr Lys Val Glu Ile Lys
            100                 105
```

<210> SEQ ID NO 72
<211> LENGTH: 107
<212> TYPE: PRT
<213> ORGANISM: Homo sapiens

<400> SEQUENCE: 72

```
Asp Ile Gln Leu Thr Gln Ser Pro Thr Phe Leu Ser Ala Ser Val Gly
1               5                   10                  15

Asp Arg Val Thr Ile Thr Cys Arg Ala Ser Gln Gly Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Phe Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Gly Gly Thr Thr Val Glu Ile Lys
            100                 105
```

<210> SEQ ID NO 73
<211> LENGTH: 112
<212> TYPE: PRT
<213> ORGANISM: Homo sapiens

<400> SEQUENCE: 73

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110
```

<210> SEQ ID NO 74
<211> LENGTH: 112
<212> TYPE: PRT
<213> ORGANISM: Homo sapiens

<400> SEQUENCE: 74

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Ser Thr Phe Gly Gln Gly Thr Lys Leu Glu Ile Lys
                100                 105                 110
```

<210> SEQ ID NO 75
<211> LENGTH: 112
<212> TYPE: PRT
<213> ORGANISM: Homo sapiens

<400> SEQUENCE: 75

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Tyr Thr Phe Gly Gln Gly Thr Lys Leu Glu Ile Lys
                100                 105                 110
```

<210> SEQ ID NO 76
<211> LENGTH: 112
<212> TYPE: PRT
<213> ORGANISM: Homo sapiens

<400> SEQUENCE: 76

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Arg
                 20                  25                  30

Asn Gly Tyr Asn Tyr Leu Asp Trp Tyr Leu Gln Arg Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Tyr Thr Phe Gly Gln Gly Thr Lys Leu Gln Ile Lys
                100                 105                 110
```

<210> SEQ ID NO 77
<211> LENGTH: 112
<212> TYPE: PRT
<213> ORGANISM: Homo sapiens

<400> SEQUENCE: 77

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
```

```
                20                  25                  30
Asn Gly Tyr Asn Tyr Leu Asp Trp Tyr Leu Gln Lys Pro Gly Gln Ser
            35                  40                  45
Pro Gln Leu Leu Ile Tyr Leu Gly Ser Asn Arg Ala Ser Gly Val Pro
        50                  55                  60
Asp Arg Phe Ser Gly Ser Gly Ser Gly Thr Asp Phe Thr Leu Asn Ile
65                  70                  75                  80
Ser Arg Val Glu Ala Asp Asp Val Gly Val Tyr Tyr Cys Met Gln Ala
                85                  90                  95
Leu Gln Thr Pro Tyr Thr Phe Gly Gln Gly Thr Lys Leu Glu Ile Lys
                100                 105                 110

<210> SEQ ID NO 78
<211> LENGTH: 112
<212> TYPE: PRT
<213> ORGANISM: Homo sapiens

<400> SEQUENCE: 78

Asp Ile Val Met Thr Gln Ser Pro Pro Ser Leu Pro Val Thr Pro Gly
1               5                   10                  15
Glu Pro Ala Ser Ile Ser Cys Arg Ser Ser Gln Ser Leu Leu His Thr
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Thr Ile
65                  70                  75                  80
Ser Arg Val Glu Ala Glu Asp Val Gly Val Phe Tyr Cys Met Gln Ala
                85                  90                  95
Leu Glu Pro Pro Tyr Thr Phe Gly Gln Gly Thr Lys Leu Glu Ile Lys
                100                 105                 110

<210> SEQ ID NO 79
<211> LENGTH: 112
<212> TYPE: PRT
<213> ORGANISM: Homo sapiens

<400> SEQUENCE: 79

Asp Ile Val Met Thr Gln Ser Pro Leu Ser Leu Ser Val Ser Pro Gly
1               5                   10                  15
Glu Pro Ala Ser Ile Ser Cys Arg Ser Ser Gln Ser Leu Leu Asp Ser
            20                  25                  30
Asn Gly His Asn Phe Leu Asp Trp Tyr Leu Gln Lys Pro Gly Gln Ser
        35                  40                  45
Pro Gln Leu Leu Ile Phe Val Gly Ser Tyr Arg Ala Leu Gly Val Pro
    50                  55                  60
Asp Arg Phe Thr Gly Ser Gly Thr Gly Thr Asp Phe Thr Leu Lys Ile
65                  70                  75                  80
Ser Arg Val Glu Pro Glu Asp Val Gly Val Tyr Tyr Cys Met Gln Gly
                85                  90                  95
Leu Gln Ala Pro Ile Thr Phe Gly Gln Gly Thr Lys Leu Asp Ile Lys
                100                 105                 110

<210> SEQ ID NO 80
<211> LENGTH: 112
<212> TYPE: PRT
<213> ORGANISM: Homo sapiens
```

<400> SEQUENCE: 80

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly His Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 81
<211> LENGTH: 112
<212> TYPE: PRT
<213> ORGANISM: Homo sapiens

<400> SEQUENCE: 81

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Tyr Leu Asp Trp Tyr Leu Gln Lys Pro Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 82
<211> LENGTH: 112
<212> TYPE: PRT
<213> ORGANISM: Homo sapiens

<400> SEQUENCE: 82

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Pro Pro Thr Phe Gly Gly Gly Thr Lys Val Glu Ile Lys

<210> SEQ ID NO 83
<211> LENGTH: 112
<212> TYPE: PRT
<213> ORGANISM: Homo sapiens

<400> SEQUENCE: 83

Asp Ile Val Met Thr Gln Ser Pro Val Ser Leu Ala Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Val Gly Val Tyr Tyr Cys Met Gln Ala
                85                  90                  95

Leu Gln Ser Pro Phe Thr Phe Gly Gly Gly Thr Lys Val Glu Ile Lys
            100                 105                 110

<210> SEQ ID NO 84
<211> LENGTH: 112
<212> TYPE: PRT
<213> ORGANISM: Homo sapiens

<400> SEQUENCE: 84

Asp Ile Val Met Thr Gln Ser Pro Val Ser Leu Ala Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Val Gly Val Tyr Tyr Cys Met Gln Ala
                85                  90                  95

Leu Gln Ser Pro Phe Thr Phe Gly Gly Gly Thr Lys Val Glu Ile Lys
            100                 105                 110

<210> SEQ ID NO 85
<211> LENGTH: 112
<212> TYPE: PRT
<213> ORGANISM: Homo sapiens

<400> SEQUENCE: 85

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Ala Ser Asn Arg Ala Ser Gly Val Pro
    50                  55                  60

```
Asp Arg Phe Ser Gly Ser Gly Ser Gly Thr Asp Phe Thr Leu Lys Ile
65                  70                  75                  80

Ser Arg Val Glu Pro Glu Asp Val Gly Leu Tyr Tyr Cys Met Gln Ala
                85                  90                  95

Leu Gln Thr Pro Leu Thr Phe Gly Gly Gly Ser Lys Val Glu Ile Lys
            100                 105                 110
```

<210> SEQ ID NO 86
<211> LENGTH: 112
<212> TYPE: PRT
<213> ORGANISM: Homo sapiens

<400> SEQUENCE: 86

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Val Ser Gly Thr Asp Phe Thr Leu Lys Ile
65                  70                  75                  80

Ser Arg Val Glu Ala Gly Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110
```

<210> SEQ ID NO 87
<211> LENGTH: 112
<212> TYPE: PRT
<213> ORGANISM: Homo sapiens

<400> SEQUENCE: 87

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Arg Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Gly Asp Val Gly Val Tyr Tyr Cys Met Gln Ala
                85                  90                  95

Leu Gln Thr Pro Pro Thr Phe Gly Gln Gly Thr Arg Leu Glu Ile Lys
            100                 105                 110
```

<210> SEQ ID NO 88
<211> LENGTH: 113
<212> TYPE: PRT
<213> ORGANISM: Homo sapiens

<400> SEQUENCE: 88

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Glu Ile
 65                  70                  75                  80

Ser Arg Val Glu Ala Glu Asp Val Gly Val Tyr Tyr Cys Met Gln Ala
                85                  90                  95

Leu Gln Thr Pro Pro Val Thr Phe Gly Gln Gly Thr Arg Leu Glu Ile
            100                 105                 110

Lys
```

<210> SEQ ID NO 89
<211> LENGTH: 113
<212> TYPE: PRT
<213> ORGANISM: Homo sapiens

<400> SEQUENCE: 89

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Arg Pro Val Thr Phe Gly Gln Gly Thr Arg Leu Glu Ile
            100                 105                 110

Lys
```

<210> SEQ ID NO 90
<211> LENGTH: 112
<212> TYPE: PRT
<213> ORGANISM: Homo sapiens

<400> SEQUENCE: 90

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Thr
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser His Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110
```

<210> SEQ ID NO 91

```
<211> LENGTH: 112
<212> TYPE: PRT
<213> ORGANISM: Homo sapiens

<400> SEQUENCE: 91

Asp Ile Val Met Thr Gln Ser Pro Leu Ser Leu Pro Val Thr Pro Gly
1               5                   10                  15

Glu Pro Ala Ser Ile Ser Cys Arg Ser Gly Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Glu
            100                 105                 110

<210> SEQ ID NO 92
<211> LENGTH: 112
<212> TYPE: PRT
<213> ORGANISM: Homo sapiens

<400> SEQUENCE: 92

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Val Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Leu Ile Thr Phe Gly Gln Gly Thr Arg Leu Glu Ile Lys
            100                 105                 110

<210> SEQ ID NO 93
<211> LENGTH: 112
<212> TYPE: PRT
<213> ORGANISM: Homo sapiens

<400> SEQUENCE: 93

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ile Gly Val Tyr Tyr Cys Met Gln Ala
```

-continued

```
                85                  90                  95

Gln Asp Ser Pro Val Thr Phe Gly Gln Gly Thr Arg Leu Asp Ile Asn
                100                 105                 110

<210> SEQ ID NO 94
<211> LENGTH: 112
<212> TYPE: PRT
<213> ORGANISM: Homo sapiens

<400> SEQUENCE: 94

Asp Ile Val Met Thr Gln Ser Pro Leu Ser Leu Pro Val Thr Pro Gly
1               5                   10                  15

Glu Pro Ala Ser Ile Ser Cys Arg Ser Asn Gln Ser Val Leu His Ser
                20                  25                  30

Asn Gly Arg His Tyr Leu Asp Trp Tyr Leu Gln Lys Pro Gly Gln Ser
            35                  40                  45

Pro Gln Leu Leu Ile Tyr Met Val Phe Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ser Glu Asp Val Gly Val Tyr Tyr Cys Met Gln Ala
                85                  90                  95

Gln Gln Thr Pro Val Thr Phe Gly Gln Gly Thr Arg Leu Asp Ile Lys
                100                 105                 110

<210> SEQ ID NO 95
<211> LENGTH: 108
<212> TYPE: PRT
<213> ORGANISM: Homo sapiens

<400> SEQUENCE: 95

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Val Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gly Ser Pro
                85                  90                  95

Leu Thr Phe Gly Gly Gly Thr Lys Val Glu Ile Lys
                100                 105

<210> SEQ ID NO 96
<211> LENGTH: 108
<212> TYPE: PRT
<213> ORGANISM: Homo sapiens

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asn Asn
                20                  25                  30

Tyr Leu Ala Trp Tyr Gln Gln Arg Pro Gly Arg Ala Pro Arg Leu Val
            35                  40                  45
```

```
Met Tyr Asp Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Pro Thr Phe Gly Gly Gly Thr Lys Val Glu Ile Lys
                100                 105
```

<210> SEQ ID NO 97
<211> LENGTH: 107
<212> TYPE: PRT
<213> ORGANISM: Homo sapiens

<400> SEQUENCE: 97

```
Glu Ile Val Leu Thr Gln Ser Pro Asp Thr Leu Ser Leu Ser Pro Gly
1               5                   10                  15

Asp Arg Ala Thr Leu Ser Cys Arg Ala Ser Gln Ser Val Ser Asn Tyr
                20                  25                  30

Leu Ala Trp Tyr Gln Gln Lys Ala Gly Arg Ala Pro Ser Leu Leu Ile
            35                  40                  45

Tyr Gly Thr Ser Arg Arg Ala Thr Asp Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Ser Ala Val Tyr Tyr Cys Gln Gln Tyr Gly Ser Ala Ser Leu
                85                  90                  95

Thr Phe Gly Gly Gly Thr Lys Val Glu Ile Lys
                100                 105
```

<210> SEQ ID NO 98
<211> LENGTH: 107
<212> TYPE: PRT
<213> ORGANISM: Homo sapiens

<400> SEQUENCE: 98

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
                100                 105
```

<210> SEQ ID NO 99
<211> LENGTH: 106
<212> TYPE: PRT
<213> ORGANISM: Homo sapiens

<400> SEQUENCE: 99

```
Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                85                  90                  95

Phe Gly Gly Gly Thr Lys Val Glu Ile Lys
            100                 105

<210> SEQ ID NO 100
<211> LENGTH: 107
<212> TYPE: PRT
<213> ORGANISM: Homo sapiens

<400> SEQUENCE: 100

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Phe
            20                  25                  30

Leu Ala Trp Tyr Gln Gln Lys Pro Gly Gln Ala Pro Arg Leu Leu Ile
        35                  40                  45

Tyr Asp Thr Ser Lys Arg Pro Thr Gly Ile Pro Asp Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Ser Trp Pro Leu
                85                  90                  95

Thr Phe Gly Gly Gly Thr Thr Val Glu Ile Lys
            100                 105

<210> SEQ ID NO 101
<211> LENGTH: 108
<212> TYPE: PRT
<213> ORGANISM: Homo sapiens

<400> SEQUENCE: 101

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                85                  90                  95

Ile Thr Phe Gly Gln Gly Thr Arg Leu Glu Ile Lys
            100                 105

<210> SEQ ID NO 102
<211> LENGTH: 106

```
<212> TYPE: PRT
<213> ORGANISM: Homo sapiens

<400> SEQUENCE: 102

Asp Ile Gln Met Thr Gln Ser Pro Ser Phe Leu Ser Ala Ser Val Gly
1               5                   10                  15

Asp Arg Val Thr Ile Ser Cys Arg Ala Ser Gln Ser Ile Asp Ser Tyr
            20                  25                  30

Ile Asn Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Leu Thr
                85                  90                  95

Phe Gly Gly Gly Thr Lys Val Glu Ile Lys
            100                 105

<210> SEQ ID NO 103
<211> LENGTH: 110
<212> TYPE: PRT
<213> ORGANISM: Homo sapiens

<400> SEQUENCE: 103

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu
        35                  40                  45

Ile Ile Tyr Asp Val Thr Asn Arg Pro Ser Gly Val Ser Lys Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Arg
                85                  90                  95

Ser Thr Pro Val Phe Gly Gly Gly Thr Lys Val Thr Val Leu
            100                 105                 110

<210> SEQ ID NO 104
<211> LENGTH: 108
<212> TYPE: PRT
<213> ORGANISM: Homo sapiens

<400> SEQUENCE: 104

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Tyr Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95
```

-continued

```
Trp Val Phe Gly Gly Gly Thr Lys Leu Thr Val Leu
            100                 105
```

<210> SEQ ID NO 105
<211> LENGTH: 110
<212> TYPE: PRT
<213> ORGANISM: Homo sapiens

<400> SEQUENCE: 105

```
Gln Leu Val Leu Thr Gln Ser Pro Pro Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Asn Leu Asn Ser Asp Gly Ser His Ser Lys Gly Asp Gly Val Pro Asp
    50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gln Ser Trp Asp
                85                  90                  95

Thr Gly Glu Val Phe Gly Gly Gly Thr Lys Leu Thr Val Leu
            100                 105                 110
```

<210> SEQ ID NO 106
<211> LENGTH: 109
<212> TYPE: PRT
<213> ORGANISM: Homo sapiens

<400> SEQUENCE: 106

```
Gln Ala Val Val Thr Gln Glu Pro Ser Leu Thr Val Ser Pro Gly Gly
1               5                   10                  15

Thr Val Thr Leu Thr Cys Asp Ser Ser Thr Gly Ala Val Thr Ser Gly
            20                  25                  30

His Tyr Pro Tyr Trp Leu Gln Gln Lys Pro Gly Gln Ala Pro Arg Thr
        35                  40                  45

Leu Ile Tyr Asp Thr His Asn Lys His Ser Trp Thr Pro Gly Arg Phe
    50                  55                  60

Ser Gly Ser Leu Leu Gly Lys Ala Ala Leu Thr Leu Ser Gly Ala
65                  70                  75                  80

Gln Pro Glu Asp Glu Ala Glu Tyr Tyr Cys Ser Leu Ser Tyr Ser Ala
                85                  90                  95

Val Trp Val Phe Gly Gly Gly Thr Lys Leu Thr Val Leu
            100                 105
```

<210> SEQ ID NO 107
<211> LENGTH: 36
<212> TYPE: DNA
<213> ORGANISM: Homo sapiens

<400> SEQUENCE: 107
gatctgcggc tgaatagtct tattgtgccg tggagt        36

<210> SEQ ID NO 108
<211> LENGTH: 27
<212> TYPE: DNA
<213> ORGANISM: Homo sapiens

<400> SEQUENCE: 108

-continued

```
tgtcctagtc tggcgcatcg ttggtgc                                           27
```

<210> SEQ ID NO 109
<211> LENGTH: 36
<212> TYPE: DNA
<213> ORGANISM: Homo sapiens

<400> SEQUENCE: 109

```
tttcctctga atacgattat tcatagtgcg gtttat                                 36
```

<210> SEQ ID NO 110
<211> LENGTH: 27
<212> TYPE: DNA
<213> ORGANISM: Homo sapiens

<400> SEQUENCE: 110

```
tgtattgttc cttggttttt tcattgc                                           27
```

<210> SEQ ID NO 111
<211> LENGTH: 12
<212> TYPE: PRT
<213> ORGANISM: Homo sapiens

<400> SEQUENCE: 111

Asp Leu Arg Leu Asn Ser Leu Ile Val Pro Trp Ser
1               5                   10

<210> SEQ ID NO 112
<211> LENGTH: 9
<212> TYPE: PRT
<213> ORGANISM: Homo sapiens

<400> SEQUENCE: 112

Cys Pro Ser Leu Ala His Arg Trp Cys
1               5

<210> SEQ ID NO 113
<211> LENGTH: 12
<212> TYPE: PRT
<213> ORGANISM: Homo sapiens

<400> SEQUENCE: 113

Phe Pro Leu Asn Thr Ile Ile His Ser Ala Val Tyr
1               5                   10

<210> SEQ ID NO 114
<211> LENGTH: 9
<212> TYPE: PRT
<213> ORGANISM: Homo sapiens

<400> SEQUENCE: 114

Cys Ile Val Pro Trp Phe Phe His Cys
1               5

<210> SEQ ID NO 115
<211> LENGTH: 27
<212> TYPE: DNA
<213> ORGANISM: Homo sapiens

<400> SEQUENCE: 115

```
tgtctggttc cgtggatgtt tcattgc                                           27
```

<210> SEQ ID NO 116
<211> LENGTH: 9
<212> TYPE: PRT

```
<213> ORGANISM: Homo sapiens

<400> SEQUENCE: 116

Cys Leu Val Pro Trp Met Phe His Cys
1               5

<210> SEQ ID NO 117
<211> LENGTH: 36
<212> TYPE: DNA
<213> ORGANISM: Homo sapiens

<400> SEQUENCE: 117
tggtctttgc atactcttgg tctgcctttt gttttt                            36

<210> SEQ ID NO 118
<211> LENGTH: 12
<212> TYPE: PRT
<213> ORGANISM: Homo sapiens

<400> SEQUENCE: 118

Trp Ser Leu His Thr Leu Gly Leu Pro Phe Val Phe
1               5                   10

<210> SEQ ID NO 119
<211> LENGTH: 27
<212> TYPE: DNA
<213> ORGANISM: Homo sapiens

<400> SEQUENCE: 119
tgtgtggtgc cgtggttttt tcattgc                                      27

<210> SEQ ID NO 120
<211> LENGTH: 9
<212> TYPE: PRT
<213> ORGANISM: Homo sapiens

<400> SEQUENCE: 120

Cys Val Val Pro Trp Phe Phe His Cys
1               5

<210> SEQ ID NO 121
<211> LENGTH: 27
<212> TYPE: DNA
<213> ORGANISM: Homo sapiens

<400> SEQUENCE: 121
tgtactcatt ggtggcgtcc ggcttgc                                      27

<210> SEQ ID NO 122
<211> LENGTH: 9
<212> TYPE: PRT
<213> ORGANISM: Homo sapiens

<400> SEQUENCE: 122

Cys Thr His Trp Trp Arg Pro Ala Cys
1               5

<210> SEQ ID NO 123
<211> LENGTH: 27
<212> TYPE: DNA
<213> ORGANISM: Homo sapiens

<400> SEQUENCE: 123
tgtctgattc cgtggatgtt taattgc                                      27
```

```
<210> SEQ ID NO 124
<211> LENGTH: 9
<212> TYPE: PRT
<213> ORGANISM: Homo sapiens

<400> SEQUENCE: 124

Cys Leu Ile Pro Trp Met Phe Asn Cys
1               5

<210> SEQ ID NO 125
<211> LENGTH: 27
<212> TYPE: DNA
<213> ORGANISM: Homo sapiens

<400> SEQUENCE: 125
tgtacgtggc tgccttatcc gtattgc                                          27

<210> SEQ ID NO 126
<211> LENGTH: 9
<212> TYPE: PRT
<213> ORGANISM: Homo sapiens

<400> SEQUENCE: 126

Cys Thr Trp Leu Pro Tyr Pro Tyr Cys
1               5

<210> SEQ ID NO 127
<211> LENGTH: 27
<212> TYPE: DNA
<213> ORGANISM: Homo sapiens

<400> SEQUENCE: 127
tgtgttacgt cgaagccgca tacgtgc                                          27

<210> SEQ ID NO 128
<211> LENGTH: 9
<212> TYPE: PRT
<213> ORGANISM: Homo sapiens

<400> SEQUENCE: 128

Cys Val Thr Ser Lys Pro His Thr Cys
1               5

<210> SEQ ID NO 129
<211> LENGTH: 27
<212> TYPE: DNA
<213> ORGANISM: Homo sapiens

<400> SEQUENCE: 129
tgtattattc cgtttatgtt tcagtgc                                          27

<210> SEQ ID NO 130
<211> LENGTH: 9
<212> TYPE: PRT
<213> ORGANISM: Homo sapiens

<400> SEQUENCE: 130

Cys Ile Ile Pro Phe Met Phe Gln Cys
1               5

<210> SEQ ID NO 131
<211> LENGTH: 36
<212> TYPE: DNA
<213> ORGANISM: Homo sapiens
```

```
<400> SEQUENCE: 131
aagcatagta tgccgattaa tgctattctt cctcct                              36

<210> SEQ ID NO 132
<211> LENGTH: 12
<212> TYPE: PRT
<213> ORGANISM: Homo sapiens

<400> SEQUENCE: 132

Lys His Ser Met Pro Ile Asn Ala Ile Leu Pro Pro
1               5                   10

<210> SEQ ID NO 133
<211> LENGTH: 36
<212> TYPE: DNA
<213> ORGANISM: Homo sapiens

<400> SEQUENCE: 133
cttccgtttg atacgattat taagccctgg cctgtg                              36

<210> SEQ ID NO 134
<211> LENGTH: 12
<212> TYPE: PRT
<213> ORGANISM: Homo sapiens

<400> SEQUENCE: 134

Leu Pro Phe Asp Thr Ile Ile Lys Pro Trp Pro Val
1               5                   10

<210> SEQ ID NO 135
<211> LENGTH: 36
<212> TYPE: DNA
<213> ORGANISM: Homo sapiens

<400> SEQUENCE: 135
attgatgtgt ggtggcttag tacgtagggt gttccg                              36

<210> SEQ ID NO 136
<211> LENGTH: 12
<212> TYPE: PRT
<213> ORGANISM: Homo sapiens

<400> SEQUENCE: 136

Ile Asp Val Trp Trp Leu Ser Thr Gln Gly Val Pro
1               5                   10

<210> SEQ ID NO 137
<211> LENGTH: 27
<212> TYPE: DNA
<213> ORGANISM: Homo sapiens

<400> SEQUENCE: 137
tgtattgtgg agcatttttt tcattgc                                        27

<210> SEQ ID NO 138
<211> LENGTH: 9
<212> TYPE: PRT
<213> ORGANISM: Homo sapiens

<400> SEQUENCE: 138

Cys Ile Val Glu His Phe Phe His Cys
1               5

<210> SEQ ID NO 139
```

```
<211> LENGTH: 27
<212> TYPE: DNA
<213> ORGANISM: Homo sapiens

<400> SEQUENCE: 139
tgtgagactt ggtggcggct ttcgtgc                                          27

<210> SEQ ID NO 140
<211> LENGTH: 9
<212> TYPE: PRT
<213> ORGANISM: Homo sapiens

<400> SEQUENCE: 140

Cys Glu Thr Trp Trp Arg Leu Ser Cys
1               5

<210> SEQ ID NO 141
<211> LENGTH: 36
<212> TYPE: DNA
<213> ORGANISM: Homo sapiens

<400> SEQUENCE: 141
ttgccgttta atactttgat tgttcctggg cggact                                 36

<210> SEQ ID NO 142
<211> LENGTH: 12
<212> TYPE: PRT
<213> ORGANISM: Homo sapiens

<400> SEQUENCE: 142

Leu Pro Phe Asn Thr Leu Ile Val Pro Gly Arg Thr
1               5                   10

<210> SEQ ID NO 143
<211> LENGTH: 36
<212> TYPE: DNA
<213> ORGANISM: Homo sapiens

<400> SEQUENCE: 143
tttccgctta tgagtctgat taatccgtgg cgtacg                                 36

<210> SEQ ID NO 144
<211> LENGTH: 12
<212> TYPE: PRT
<213> ORGANISM: Homo sapiens

<400> SEQUENCE: 144

Phe Pro Leu Met Ser Leu Ile Asn Pro Trp Arg Thr
1               5                   10

<210> SEQ ID NO 145
<211> LENGTH: 27
<212> TYPE: DNA
<213> ORGANISM: Homo sapiens

<400> SEQUENCE: 145
tgtcagcata agctgccttc taattgc                                          27

<210> SEQ ID NO 146
<211> LENGTH: 9
<212> TYPE: PRT
<213> ORGANISM: Homo sapiens

<400> SEQUENCE: 146

Cys Gln His Lys Leu Pro Ser Asn Cys
```

<210> SEQ ID NO 147
<211> LENGTH: 27
<212> TYPE: DNA
<213> ORGANISM: Homo sapiens

<400> SEQUENCE: 147
tgtgtggttc agtggatgtt tcagtgc                                          27

<210> SEQ ID NO 148
<211> LENGTH: 9
<212> TYPE: PRT
<213> ORGANISM: Homo sapiens

<400> SEQUENCE: 148

Cys Val Val Gln Trp Met Phe Gln Cys
1               5

<210> SEQ ID NO 149
<211> LENGTH: 36
<212> TYPE: DNA
<213> ORGANISM: Homo sapiens

<400> SEQUENCE: 149
tttctgccga tttctacgct gattactccg tctggt                                36

<210> SEQ ID NO 150
<211> LENGTH: 12
<212> TYPE: PRT
<213> ORGANISM: Homo sapiens

<400> SEQUENCE: 150

Phe Leu Pro Ile Ser Thr Leu Ile Thr Pro Ser Gly
1               5                   10

<210> SEQ ID NO 151
<211> LENGTH: 27
<212> TYPE: DNA
<213> ORGANISM: Homo sapiens

<400> SEQUENCE: 151
tgtgttgtgt cgtggatgtt tcagtgc                                          27

<210> SEQ ID NO 152
<211> LENGTH: 9
<212> TYPE: PRT
<213> ORGANISM: Homo sapiens

<400> SEQUENCE: 152

Cys Val Val Ser Trp Met Phe Gln Cys
1               5

<210> SEQ ID NO 153
<211> LENGTH: 113
<212> TYPE: PRT
<213> ORGANISM: Homo sapiens

<400> SEQUENCE: 153

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met

```
                35                  40                  45
Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Tyr Phe Asp Tyr Trp Gly Gln Gly Thr Leu Val Thr Val Ser
                100                 105                 110

Ser
```

<210> SEQ ID NO 154
<211> LENGTH: 120
<212> TYPE: PRT
<213> ORGANISM: Homo sapiens

<400> SEQUENCE: 154

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
                35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Asp Thr Ala Met Val Asp Ala Phe Asp Ile Trp Gly Gln
                100                 105                 110

Gly Thr Met Val Thr Val Ser Ser
                115                 120
```

<210> SEQ ID NO 155
<211> LENGTH: 123
<212> TYPE: PRT
<213> ORGANISM: Homo sapiens

<400> SEQUENCE: 155

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
                35                  40                  45

Ser Ser Ile Ser Ser Ser Ser Ser Tyr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Pro Tyr Tyr Asp Ser Ser Gly Tyr Tyr Tyr Phe Asp Tyr
                100                 105                 110

Trp Gly Gln Gly Thr Leu Val Thr Val Ser Ser
                115                 120
```

<210> SEQ ID NO 156
<211> LENGTH: 118
<212> TYPE: PRT
<213> ORGANISM: Homo sapiens

<400> SEQUENCE: 156

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ala Ala Ala Tyr Phe Asp Tyr Trp Gly Gln Gly Thr
            100                 105                 110

Leu Val Thr Val Ser Ser
        115

<210> SEQ ID NO 157
<211> LENGTH: 117
<212> TYPE: PRT
<213> ORGANISM: Homo sapiens

<400> SEQUENCE: 157

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ala Thr Tyr Phe Asp Tyr Trp Gly Gln Gly Thr Leu
            100                 105                 110

Val Thr Val Ser Ser
        115

<210> SEQ ID NO 158
<211> LENGTH: 117
<212> TYPE: PRT
<213> ORGANISM: Homo sapiens

<400> SEQUENCE: 158

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

-continued

```
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Gly Ala Thr Tyr Phe Asp Tyr Trp Gly Gln Gly Thr Leu
            100                 105                 110
Val Thr Val Ser Ser
            115

<210> SEQ ID NO 159
<211> LENGTH: 117
<212> TYPE: PRT
<213> ORGANISM: Homo sapiens

<400> SEQUENCE: 159

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
                20                  25                  30
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Tyr Tyr Tyr Tyr Gly Met Asp Tyr Trp Gly Gln Gly Thr Thr
            100                 105                 110
Val Thr Val Ser Ser
            115

<210> SEQ ID NO 160
<211> LENGTH: 107
<212> TYPE: PRT
<213> ORGANISM: Homo sapiens

<400> SEQUENCE: 160

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Leu
                85                  90                  95
Thr Phe Gly Gly Gly Thr Lys Val Glu Ile Lys
            100                 105

<210> SEQ ID NO 161
<211> LENGTH: 107
```

```
-continued
```

```
<212> TYPE: PRT
<213> ORGANISM: Homo sapiens

<400> SEQUENCE: 161

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 162
<211> LENGTH: 107
<212> TYPE: PRT
<213> ORGANISM: Homo sapiens

<400> SEQUENCE: 162

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 163
<211> LENGTH: 112
<212> TYPE: PRT
<213> ORGANISM: Homo sapiens

<400> SEQUENCE: 163

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

```
Leu Gln Thr Pro Trp Thr Phe Gly Gln Gly Thr Lys Val Glu Ile Lys
            100                 105                 110
```

<210> SEQ ID NO 164
<211> LENGTH: 112
<212> TYPE: PRT
<213> ORGANISM: Homo sapiens

<400> SEQUENCE: 164

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 165
<211> LENGTH: 112
<212> TYPE: PRT
<213> ORGANISM: Homo sapiens

<400> SEQUENCE: 165

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110
```

<210> SEQ ID NO 166
<211> LENGTH: 112
<212> TYPE: PRT
<213> ORGANISM: Homo sapiens

<400> SEQUENCE: 166

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Leu Thr Phe Gly Gly Gly Thr Lys Val Glu Ile Lys
                100                 105                 110

<210> SEQ ID NO 167
<211> LENGTH: 112
<212> TYPE: PRT
<213> ORGANISM: Homo sapiens

<400> SEQUENCE: 167

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Ile Thr Phe Gly Gln Gly Thr Arg Leu Glu Ile Lys
                100                 105                 110

<210> SEQ ID NO 168
<211> LENGTH: 108
<212> TYPE: PRT
<213> ORGANISM: Homo sapiens

<400> SEQUENCE: 168

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                     85                  90                  95

Leu Thr Phe Gly Gly Gly Thr Lys Val Glu Ile Lys
                100                 105

<210> SEQ ID NO 169
<211> LENGTH: 107
<212> TYPE: PRT
<213> ORGANISM: Homo sapiens

<400> SEQUENCE: 169

Glu Ile Val Leu Thr Gln Ser Pro Ala Thr Leu Ser Leu Ser Pro Gly
 1               5                  10                  15
```

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 170
<211> LENGTH: 107
<212> TYPE: PRT
<213> ORGANISM: Homo sapiens

<400> SEQUENCE: 170

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 171
<211> LENGTH: 107
<212> TYPE: PRT
<213> ORGANISM: Homo sapiens

<400> SEQUENCE: 171

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 172
<211> LENGTH: 111
<212> TYPE: PRT

```
<213> ORGANISM: Homo sapiens

<400> SEQUENCE: 172

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
            100                 105                 110

<210> SEQ ID NO 173
<211> LENGTH: 108
<212> TYPE: PRT
<213> ORGANISM: Homo sapiens

<400> SEQUENCE: 173

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Trp Val Phe Gly Gly Gly Thr Lys Leu Thr Val Leu
            100                 105

<210> SEQ ID NO 174
<211> LENGTH: 111
<212> TYPE: PRT
<213> ORGANISM: Homo sapiens

<400> SEQUENCE: 174

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
                20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95
```

-continued

Thr Gly Ile Val Val Phe Gly Gly Gly Thr Lys Leu Thr Val Leu
              100                 105                 110

<210> SEQ ID NO 175
<211> LENGTH: 110
<212> TYPE: PRT
<213> ORGANISM: Homo sapiens

<400> SEQUENCE: 175

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg Trp Val Phe Gly Gly Gly Thr Lys Leu Thr Val Leu
            100                 105                 110

<210> SEQ ID NO 176
<211> LENGTH: 106
<212> TYPE: PRT
<213> ORGANISM: Homo sapiens

<400> SEQUENCE: 176

Asp Ile Gln Met Thr Gln Ser Pro Ser Phe Leu Ser Ala Ser Val Gly
1               5                   10                  15

Asp Arg Val Thr Ile Ser Cys Arg Ala Ser Gln Ser Ile Asp Ser Tyr
            20                  25                  30

Ile Asn Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Leu Thr
                85                  90                  95

Phe Gly Gly Gly Thr Lys Val Glu Ile Lys
            100                 105

<210> SEQ ID NO 177
<211> LENGTH: 107
<212> TYPE: PRT
<213> ORGANISM: Homo sapiens

<400> SEQUENCE: 177

Asp Ile Gln Met Thr Gln Ser Pro Ser Ser Leu Ser Ala Ser Val Gly
1               5                   10                  15

Asp Arg Val Ile Val Thr Cys Arg Ala Ser Gln Ser Ile Ser Ser Tyr
            20                  25                  30

Val Ser Trp Tyr Gln Gln Lys Pro Gly Lys Ala Pro Lys Leu Leu Ile
        35                  40                  45

Ser Thr Thr Ser Thr Leu Gln Ser Gly Val Pro Ser Arg Phe Ser Gly
    50                  55                  60

```
Ser Ala Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Arg Pro Leu
             85                  90                  95

Thr Phe Gly Gln Gly Thr Lys Val Glu Ile Lys
            100                 105
```

<210> SEQ ID NO 178
<211> LENGTH: 107
<212> TYPE: PRT
<213> ORGANISM: Homo sapiens

<400> SEQUENCE: 178

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Thr Ile Thr Ser Phe
             20                  25                  30

Leu Asn Trp Tyr Gln Gln Lys Arg Gly Lys Ala Pro Lys Leu Leu Ile
             35                  40                  45

Tyr Gly Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Thr Tyr Ser Gln Pro Leu
             85                  90                  95

Thr Phe Gly Gln Gly Thr Lys Val Glu Ile Lys
            100                 105
```

<210> SEQ ID NO 179
<211> LENGTH: 107
<212> TYPE: PRT
<213> ORGANISM: Homo sapiens

<400> SEQUENCE: 179

```
Asp Ile Gln Met Thr Gln Ser Pro Ser Ser Leu Ser Ala Phe Val Gly
  1               5                  10                  15

Asp Arg Val Thr Ile Thr Cys Arg Ala Ser Gln Ser Ile Thr Ser Tyr
             20                  25                  30

Leu Asn Trp Tyr Gln Gln Lys Pro Gly Lys Ala Pro Asn Leu Leu Ile
             35                  40                  45

Tyr Ala Ala Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Tyr Ala Thr Tyr Tyr Cys Gln Gln Arg Tyr Ser Tyr Ile Leu
             85                  90                  95

Thr Phe Gly Gln Gly Thr Lys Val Glu Ile Lys
            100                 105
```

<210> SEQ ID NO 180
<211> LENGTH: 115
<212> TYPE: PRT
<213> ORGANISM: Homo sapiens

<400> SEQUENCE: 180

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
```

-continued

```
                    20                  25                  30
Asp Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Val Gly Ala Phe Asp Tyr Trp Gly Gln Gly Thr Leu Val Thr
            100                 105                 110
Val Ser Ser
        115

<210> SEQ ID NO 181
<211> LENGTH: 115
<212> TYPE: PRT
<213> ORGANISM: Homo sapiens

<400> SEQUENCE: 181

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Phe
            20                  25                  30
Asn Met His Trp Val Arg Gln Ala Pro Gly Lys Gly Leu Glu Trp Val
        35                  40                  45
Ala Leu Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Met Val Val Gly Ala Phe Asp Tyr Trp Gly Gln Gly Thr Leu Val Thr
            100                 105                 110
Val Ser Ser
        115

<210> SEQ ID NO 182
<211> LENGTH: 115
<212> TYPE: PRT
<213> ORGANISM: Homo sapiens

<400> SEQUENCE: 182

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Phe
            20                  25                  30
Asn Met His Trp Val Arg Gln Ala Pro Gly Lys Gly Leu Glu Trp Val
        35                  40                  45
Ala Leu Ile Ser Tyr Asp Gly Ser Asn Lys Asn Tyr Ala Asp Ser Val
    50                  55                  60
Lys Gly Arg Phe Thr Ile Ser Arg Asp Asn Ser Lys Asn Thr Leu Phe
65                  70                  75                  80
Leu Gln Met Asn Ser Leu Arg Ala Glu Asp Thr Ala Val Tyr Tyr Cys
                85                  90                  95
Met Val Val Gly Ala Phe Asp Tyr Trp Gly Gln Gly Thr Leu Val Thr
            100                 105                 110
```

```
Val Ser Ser
        115
```